United States Patent
Chen et al.

(10) Patent No.: US 11,332,476 B2
(45) Date of Patent: May 17, 2022

(54) FMS-LIKE TYROSINE KINASE INHIBITORS

(71) Applicant: 3SM BIOTRON INC., Taipei (TW)

(72) Inventors: Jung-Hsiang Chen, Taipei (TW); Tsung-Chih Chen, Nantou Country (TW); Tai Wei Ly, San Diego, CA (US); I-Chun Chen, Taipei (TW); Jiunn-Yuan Hsu, Taipei (TW)

(73) Assignee: 3SM BIOTRON INC., Taipei (TW)

( * ) Notice: Subject to any disclaimer, the term of this patent is extended or adjusted under 35 U.S.C. 154(b) by 104 days.

(21) Appl. No.: 16/630,150

(22) PCT Filed: Apr. 3, 2018

(86) PCT No.: PCT/CN2018/081730
§ 371 (c)(1),
(2) Date: Jan. 10, 2020

(87) PCT Pub. No.: WO2019/191896
PCT Pub. Date: Oct. 10, 2019

(65) Prior Publication Data
US 2020/0131194 A1    Apr. 30, 2020

(51) Int. Cl.
*C07D 495/04* (2006.01)
(52) U.S. Cl.
CPC ................... *C07D 495/04* (2013.01)

(58) Field of Classification Search
CPC ................ C07D 495/04; A61P 35/02
See application file for complete search history.

(56) References Cited

U.S. PATENT DOCUMENTS 8,927,717 B1 *   1/2015   Huang ............... C07D 495/04
                                                              546/62
2019/0111987 A1 *   4/2019   VanDamia .............. B62H 1/00

OTHER PUBLICATIONS

Krause. The New England Journal of Medicine, 2005, 353:2, 172-187 (Year: 2005).*
"Prevention-Prostate Cancer Foundation (PCF)", http://www.pcf.Org/site/c.leJRIROrEpH/b.5802029/k.31EA/Prevention.htm, accessed Apr. 18, 2016 (Year: 2016).*
Tseng. Journal of Medicinal Chemistry, 2011, 54, 3103-3107 (Year: 2011).*
Tseng. Bioorganic and Medicinal Chemistry, 2012, 20, 4397-4404 (Year: 2012).*
Zawilska. Pharmacological Reports, 2013, 65, 1-14 (Year: 2013).*

* cited by examiner

*Primary Examiner* — Noble E Jarrell
(74) *Attorney, Agent, or Firm* — WPAT, PC

(57) ABSTRACT

The present invention relates to Fms-like tyrosine kinase (FLT3) inhibitors. The present invention provides novel 4-quinolinone derivatives used as FLT3 inhibitors and for treatment and/or prevention of tumors.

9 Claims, No Drawings

FMS-LIKE TYROSINE KINASE INHIBITORS

FIELD OF THE INVENTION

The present invention relates to Fms-like tyrosine kinase (FLT3) inhibitors. The present invention provides novel 4-quinolinone derivatives used as FLT3 inhibitors and for treatment and/or prevention of tumors.

BACKGROUND OF THE INVENTION

FLT3 is a class III receptor tyrosine kinase (RTK) structurally related to the receptors for platelet derived growth factor (PDGF), colony stimulating factor 1 (CSF1), and KIT ligand (KL); these RTK contain five immunoglobulin-like domains in the extracellular region and an intracellular tyrosine kinase domain split in two by a specific hydrophilic insertion (kinase insert). FLT3 plays a key role in hematopoiesis. Members of a subset of this family include FLT3, platelet-derived growth factor receptors. (PDGFR-alpha. and PDGFR-beta) and are characterized by an extracellular domain consisting of five immunoglobulin-like (Ig-like) domains, a single transmembrane region, a cytoplasmic juxtamembrane domain (JM) and a cytoplasmic tyrosine kinase domain interrupted by a kinase insert domain (KID). Two groups independently reported the cloning of the FLT3 gene. FLT3 is also found in placenta, gonads and brain and is expressed in high levels in a wide range of hematopoietic malignancies including 70-100% of acute myelogenous leukemia (AML), acute lymphoblastic leukemia (ALL) and chronic myelogenous leukemia.

Several FLT3 inhibitors, such as PKC412 (N-benzoyl staurosporine) (Blood. 2006 Jan. 1; 107(1):293-300. Epub 2005 September) and SU5614 (Haematologica. 2005 November; 90(11):1577-8) have been shown to have antitumor activity. However, an ongoing need exists in the art to develop antitumor drug.

DETAILED DESCRIPTION OF THE INVENTION

The present invention pertains to substituted 4-quinolinone derivatives used as FLT3 inhibitors and for treatment and/or prevention of tumors.

Unless otherwise defined, all technical and scientific terms used herein have the same meaning as commonly understood by one of ordinary skill in the art to which this invention belongs applying that term in context to its use in describing the present invention. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The terms "halo" and "halogen," as used herein, refer to an atom selected from fluorine, chlorine, bromine and iodine.

The term "alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless specifically stated otherwise in the specification, an alkyl group is optionally substituted by one or more of substituents. The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkoxy" refers to a radical bonded through an oxygen atom of the formula —O-alkyl, where alkyl is an alkyl chain as defined above.

The term "alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless specifically stated otherwise in the specification, an alkenyl group is optionally substituted by one or more of substituents.

The term "cycloalkyl," as used herein, denotes a monovalent group derived from a monocyclic or polycyclic saturated or partially unsaturated carbocyclic ring compound. Examples of $C_3$-$C_8$-cycloalkyl include, but not limited to, cyclopropyl, cyclobutyl, cyclopentyl, cyclohexyl, cyclopentyl and cyclooctyl.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, indenyl and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one of the ring atoms is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heterocycloalkyl," as used herein, refers to a non-aromatic 3-, 4-, 5-, 6- or 7-membered ring or a bi- or tri-cyclic group fused of non-fused system, where (i) at least one ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formate, fumarate, gluceptate, glucoheptanoate, gluconate, glutamate, glycerophosphate, glycollylarsanilate, hemisulfate, heptanoate, hexanoate, hexylresorcinate, hydrabamate, bromide, chloride, 2-hydroxyethanesulfonate, hydroxynaphthoate, iodide, isonicotinate, isothionate, lactate, lactobionate, laurate, malate, maleate, mandelate, mesylate, methylnitrate, methylsulfate, methanesulfonate, mucate, 2-naphthalenesulfonate, napsylate, nicotinate, nitrate, oleate, oxalate, pamoate (embonate), palmitate, pantothenate, pectinate, persulfate, phosphate/diphosphate, pimelate, phenylpropanoate, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups that may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The term "subject" includes living organisms such as humans, monkeys, cows, sheep, horses, pigs, cattle, goats, dogs, cats, mice, rats, cultured cells, and transgenic species thereof. In a preferred embodiment, the subject is a human.

The term "administering" includes routes of administration which allow the active ingredient of the invention to perform their intended function.

The term "treat" or "treatment" refers to a method of reducing the effects of a disease or condition. Treatment can also refer to a method of reducing the underlying cause of the disease or condition itself rather than just the symptoms. The treatment can be any reduction from native levels and can be, but is not limited to, the complete ablation of the disease, condition, or the symptoms of the disease or condition.

The term "prevent," "prevention" or "preventing" means inhibition or averting of symptoms associated with the target disease.

The phrase "therapeutically effective amount" refers to that amount of a compound, material, or composition comprising a compound of the present invention which is effective for producing a desired therapeutic effect, at a reasonable benefit/risk ratio applicable to any medical treatment.

In one aspect, the present invention provides a compound having the following Formula (I-1), (I-2), (I-3) or (I-4),

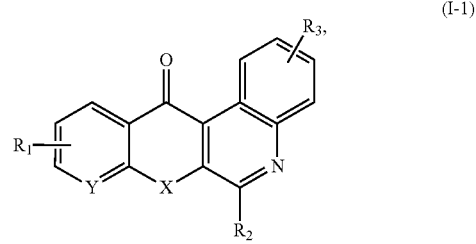

-continued

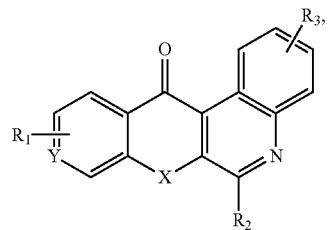
(I-2)

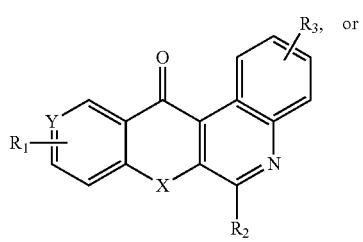
(I-3)

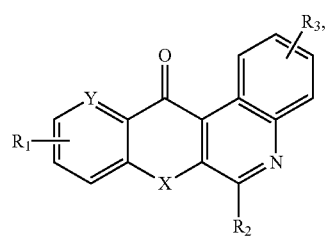
(I-4)

wherein
Y is [P]n, wherein P is —CH—, —N— or —O—;
X is [Q]n, wherein Q is —CH$_2$—. —NH—, —O—, —S—, —SO$_2$— or —N-alkyl;
n is 0 or 1;
R$_1$ represents mono-, di-, tri- or tetra-substitution and is selected from, halogen, —OH, —NH$_2$, —NO$_2$, —CN, alkyl, alkenyl, haloalkyl, —NHR$_a$, N(R$_b$)$_2$, —OR$_a$, 3-,4-,5-,6- membered cycloalkyl, 3-,4-,5-,6-heterocycloalkyl containing one or two heteroatom selected from N, O and S, aryl or heteroaryl;
  R$_a$ is H, alkyl, alkenyl, halogen, hydroxyalkyl, —OH, —NO$_2$ or phenyl;
  R$_b$ is alkyl, alkenyl or halogen;
R$_2$ is —NR$_d$R$_e$—, —O-alkyl, —C(═O)— 5- or 6-membered aryl or —C(═O)— 5- or 6-membered heteroaryl;
  R$_d$ is OH, alkyl, alkenyl, aryl, heteroaryl, heteroalkenyl, -alkylene-NR$_d$R$_e$, -alkylene-N(R$_b$)$_2$, -alkylene-OR$_c$, -alkylene-5- or 6-membered aryl, -alkylene-5- or 6-membered heteroaryl, or 5- or 6-membered heterocycloalkyl or heteroaryl containing at least one N;
  R$_e$ is H, alkyl, alkenyl or aryl; or
  R$_d$R$_e$ together with N forms a 3-8 membered heterocycloalkyl or heteroaryl ring, optionally substituted or N-substituted with C$_1$-C$_3$ alkyl, C$_1$-C$_3$ alkylene-phenyl, tert-butyloxycarbonyl,
  R$_c$ is H, alkyl, alkenyl, halogen, or phenyl;
R$_3$ is H, alkyl, alkenyl, halogen or CN, NH$_2$ or NO$_2$.
wherein the alkyl or alkenyl is unbranched or branched, unsubstituted or substituted by halogen, hydroxyl, amino or nitro; and
wherein the cycloalkyl or heterocycloalkyl is unsubstituted or substituted by halogen, —OH, —NH$_2$, —NO$_2$, —CN, alkyl, alkenyl, —NHR$_a$, N(R$_b$)$_2$ or —OR$_a$; provided that when P is —CH— and n is 1, R$_1$ at the 8 position is not Cl;

or a solvate, prodrug, stereoisomer, enantiomer, or pharmaceutically acceptable salt thereof.

In one embodiment, Q is —S— and n is 1.

In one embodiment, P is —C— or —N— and n is 1.

In one embodiment, R$_1$ is CN, F, Cl, —OC$_{1-4}$alkyl, C$_{1-4}$alkyl or haloC$_{1-4}$alkyl. In a further embodiment, Cl bonds to C11, C10, C9 or 8 when P is —C—; and —OC$_{1-4}$alkyl, F, CN, —OC$_{1-4}$alkyl, C$_{1-4}$alkyl or haloC$_{1-4}$alkyl bonds to C10 when P is —C—.

In one embodiment, R$_2$ is —NH—C$_{1-3}$alkylene-NHR$_a$, —NH—C$_{1-3}$alkylene-NH$_2$, —NH—C$_{1-3}$alkylene-OH, —NH—C$_{1-3}$alkylene-NHC$_{1-4}$alkylOH, —C$_{1-3}$alkylene-5- or 6-membered aryl, —C$_{1-3}$alkylene-5- or 6-membered heteroaryl. In a further embodiment, R$_a$ is H; Rc is hydroxyC$_{1-4}$alkyl.

In one embodiment, R$_3$ is H.

In some embodiments, the compound of the present invention is selected from the group consisting of:

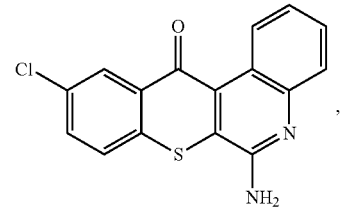
,

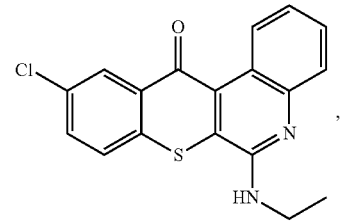
,

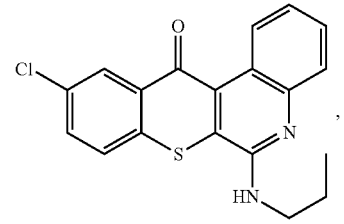
,

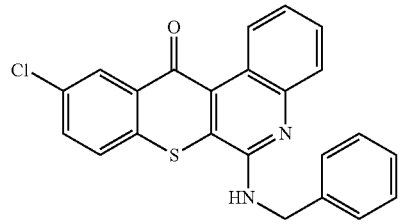
,

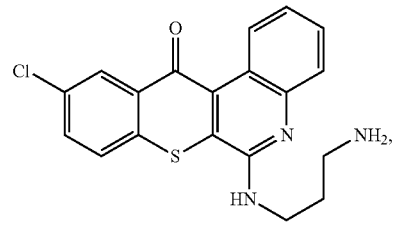
,

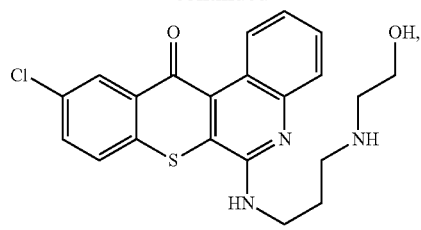
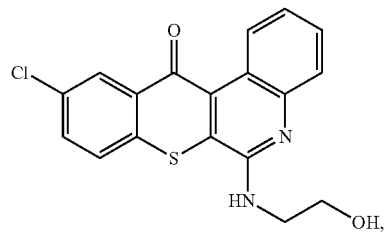
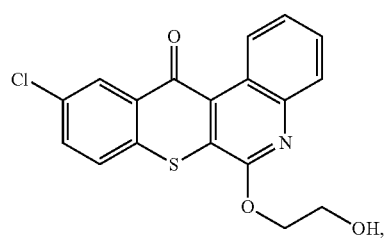
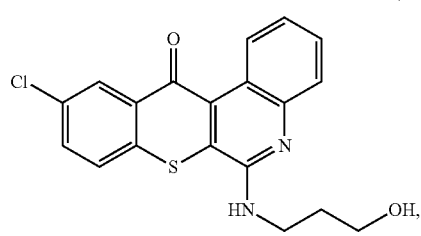
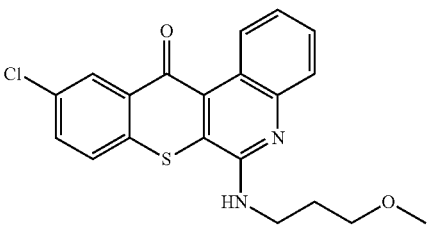
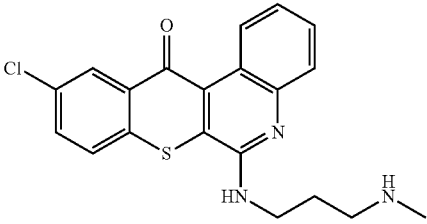
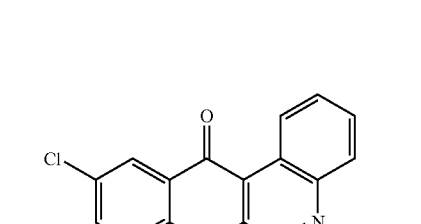
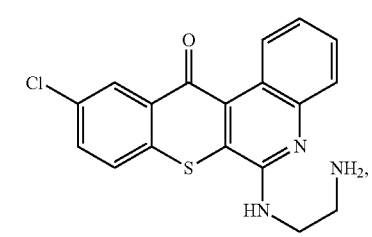
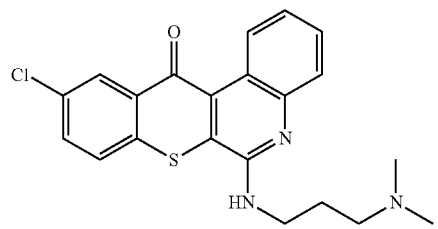
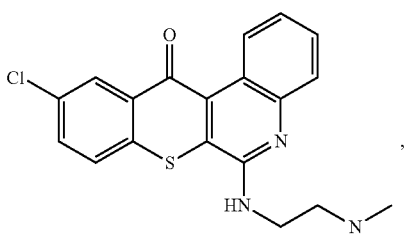
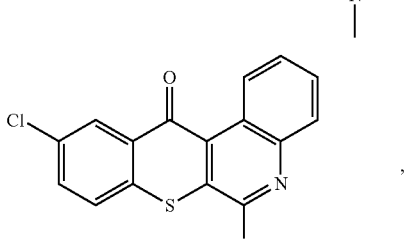
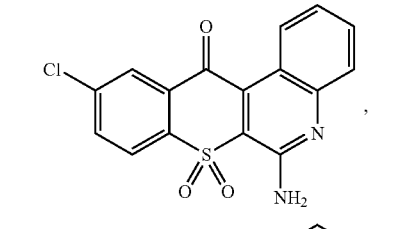
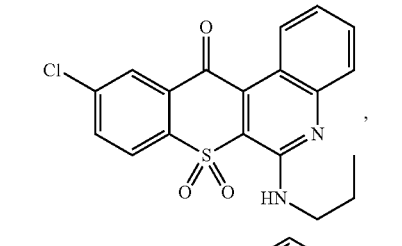
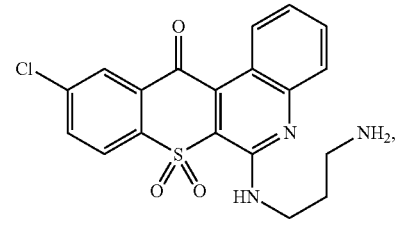
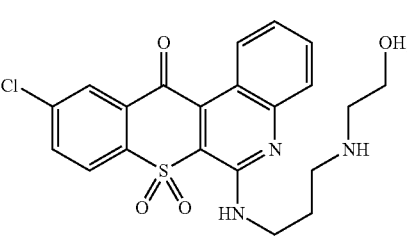

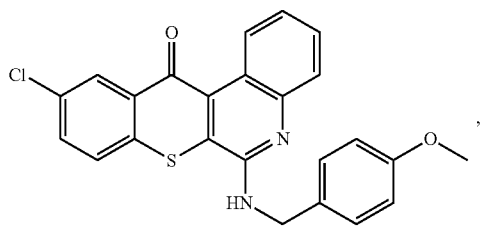
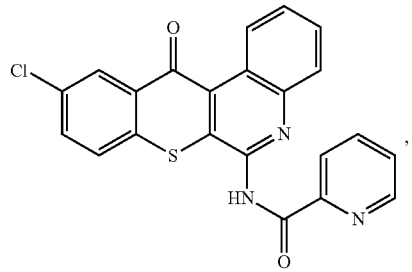
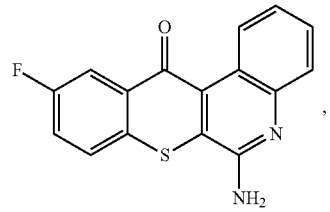
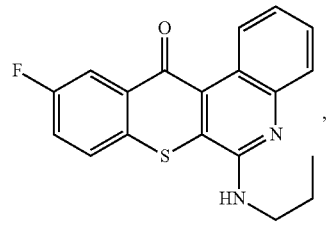
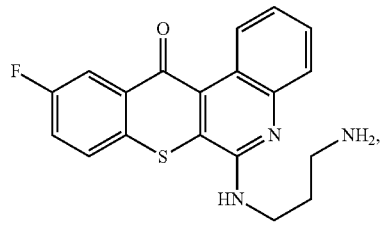
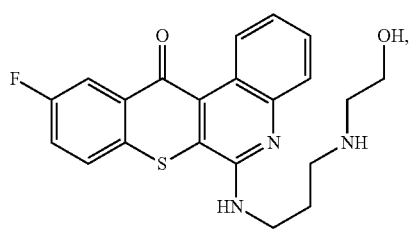
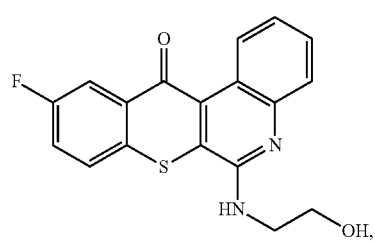
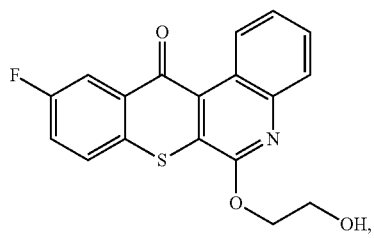
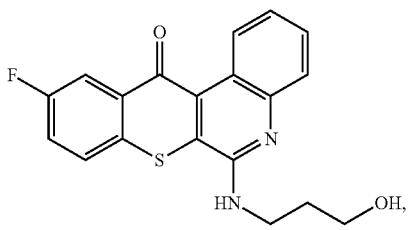
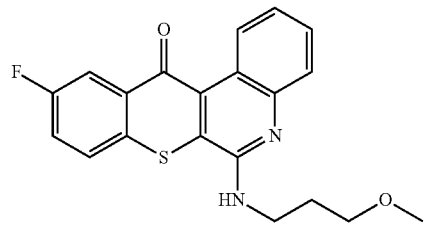
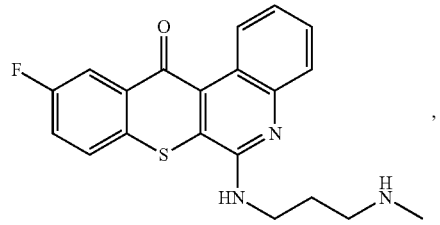
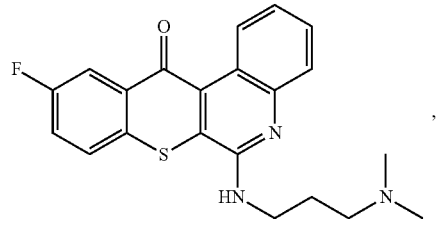
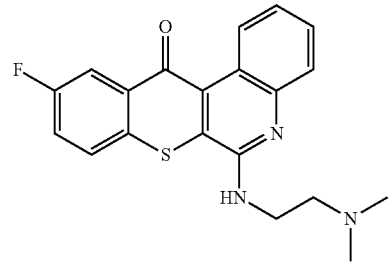

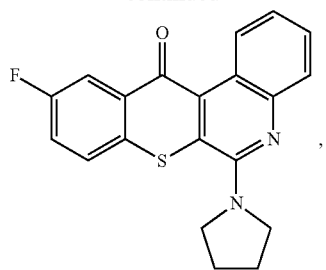,
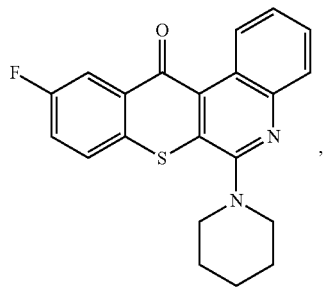,
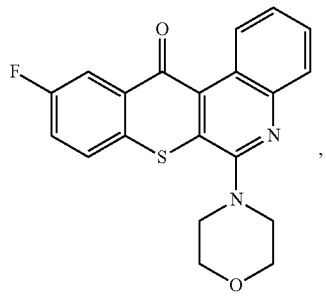,
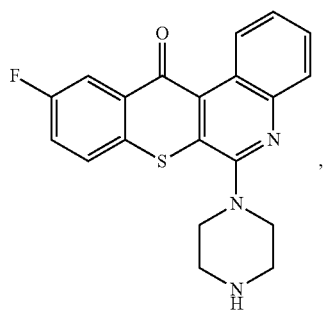,
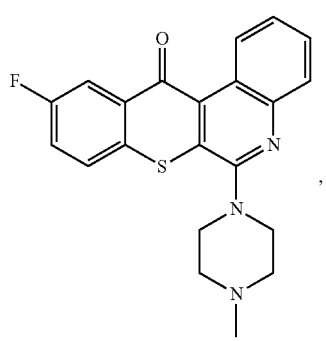,
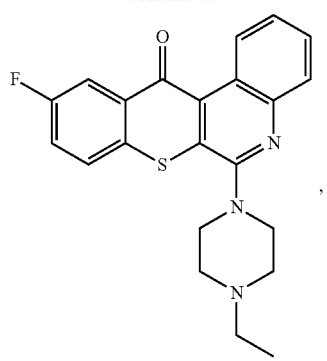,
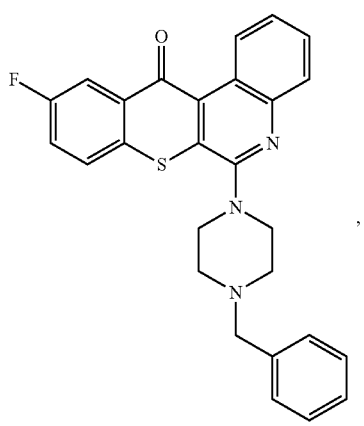,
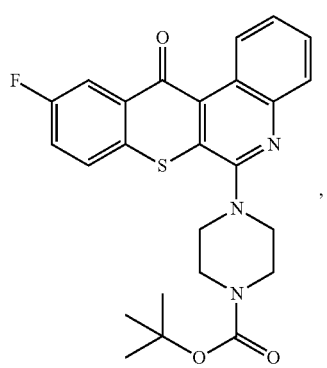,
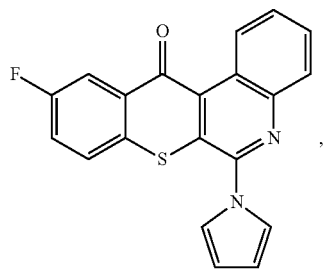,
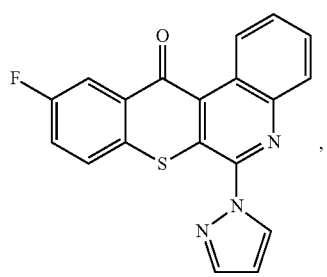,

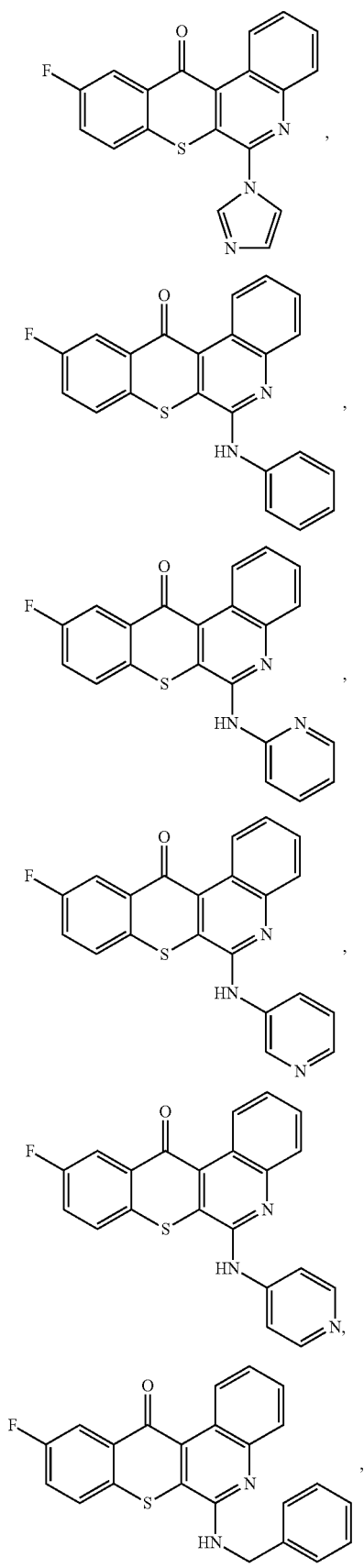
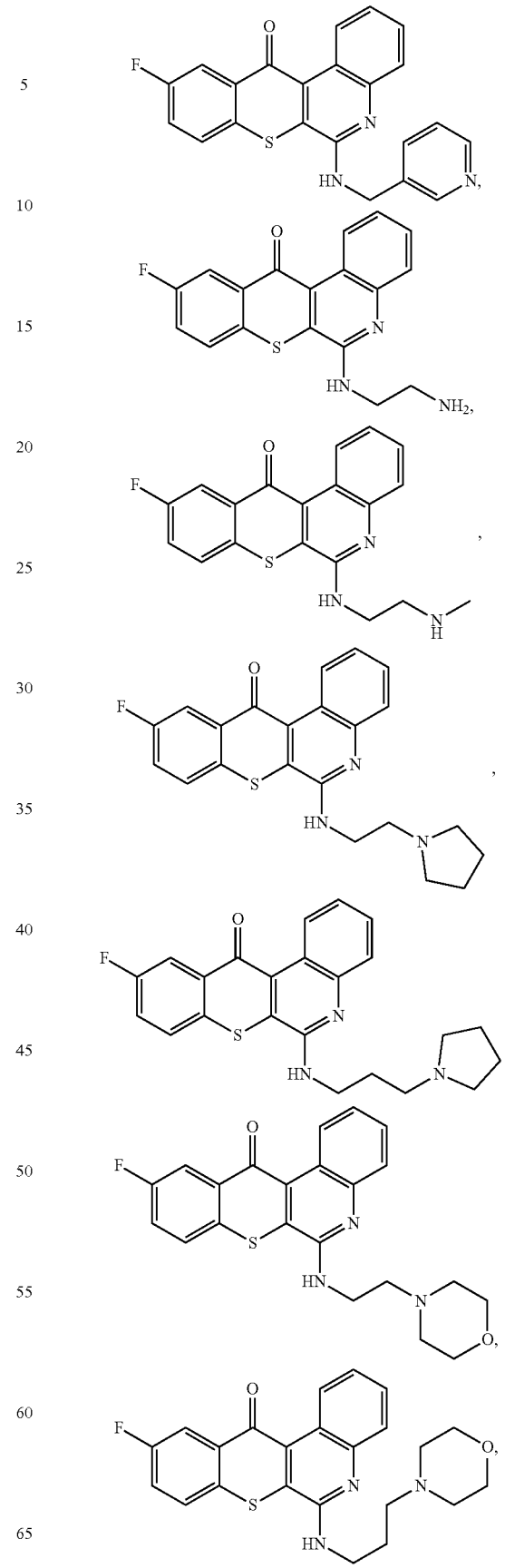

-continued
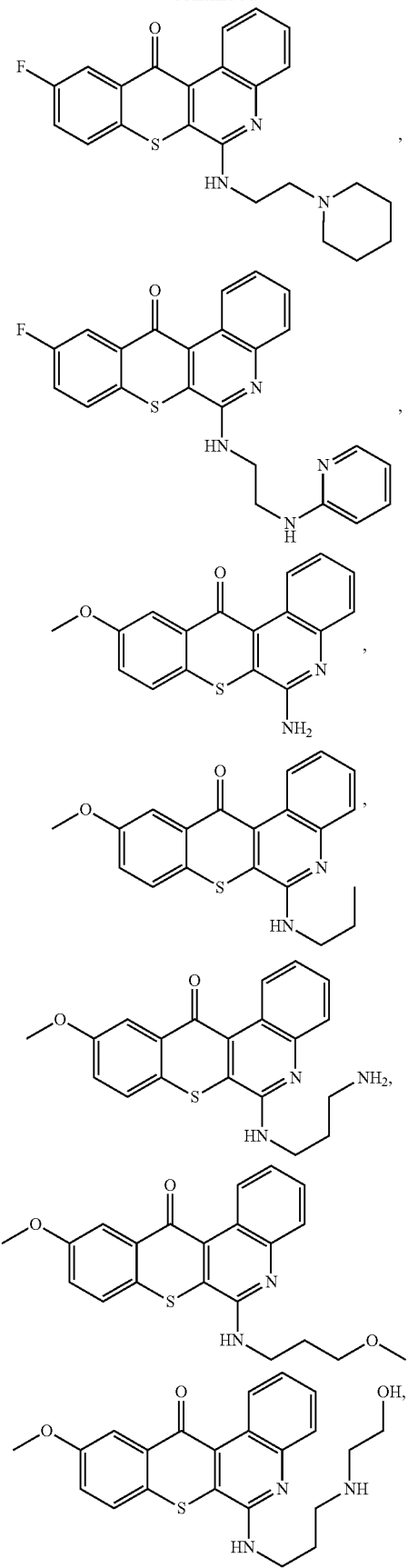
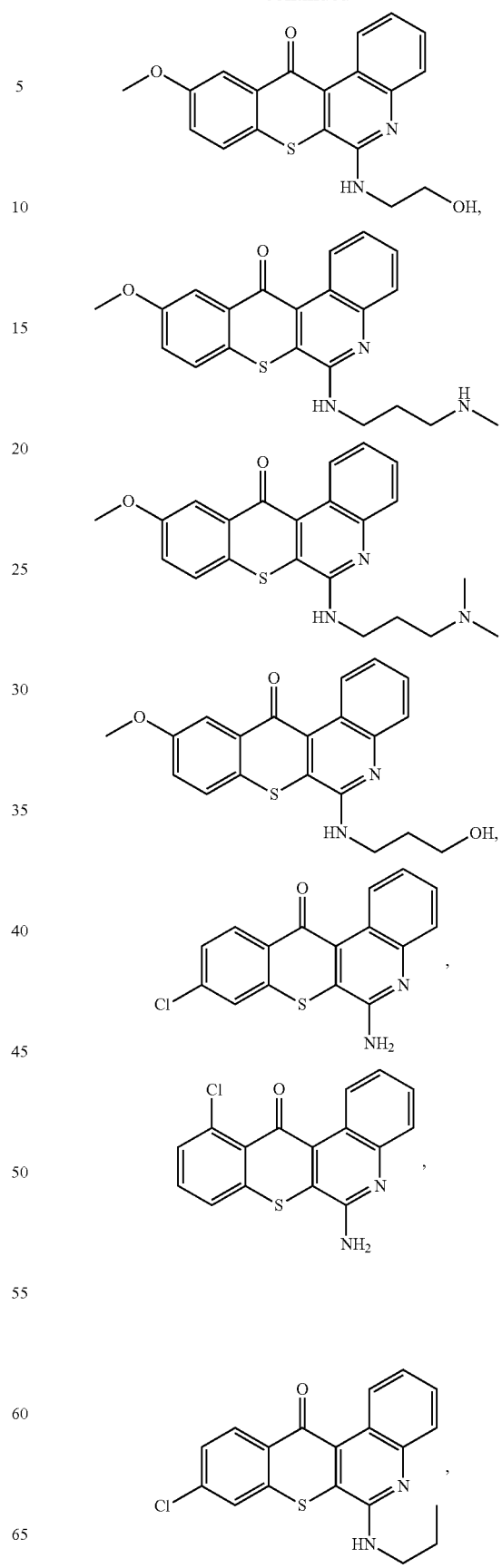

-continued
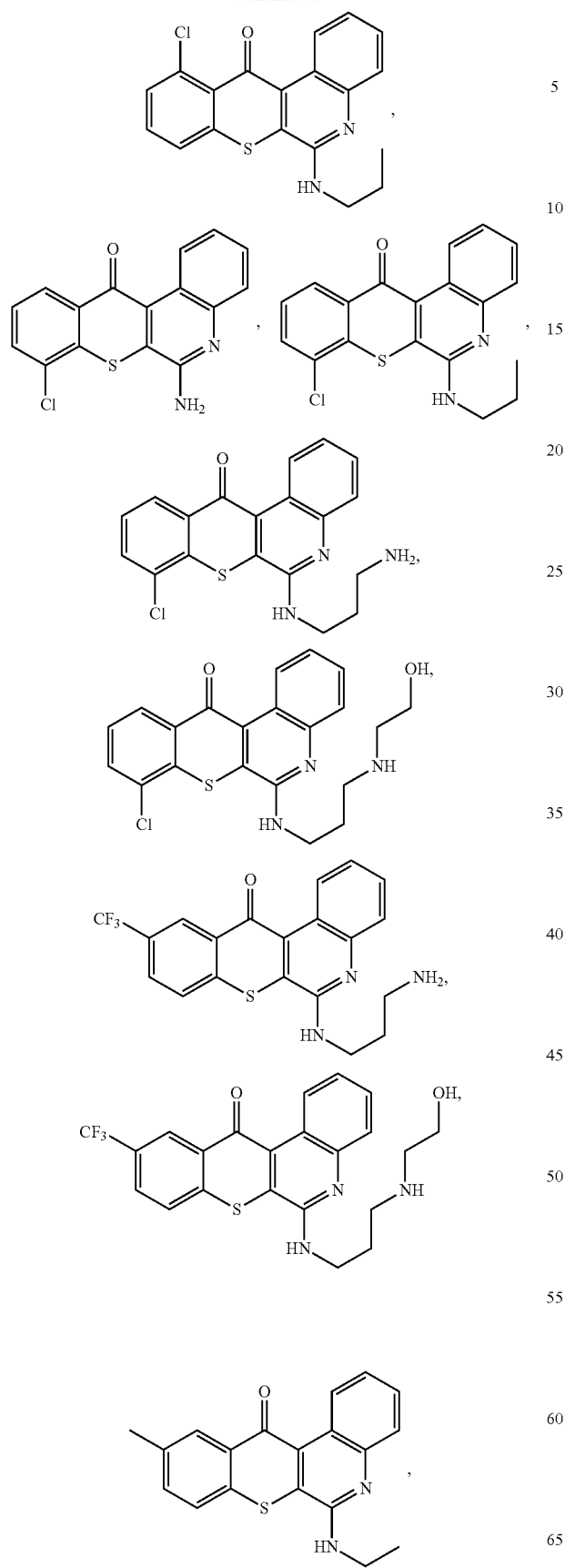
-continued
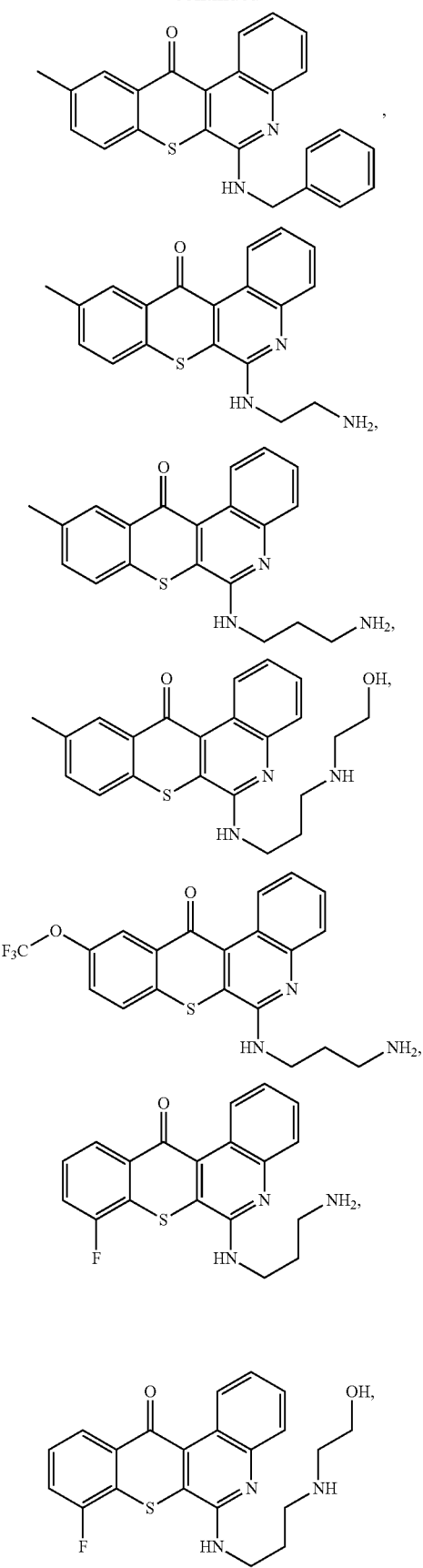

-continued
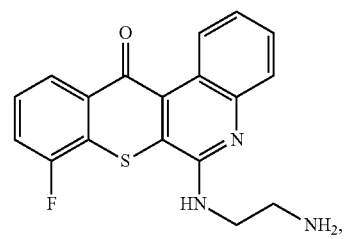
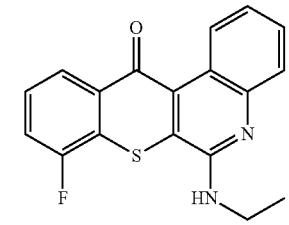
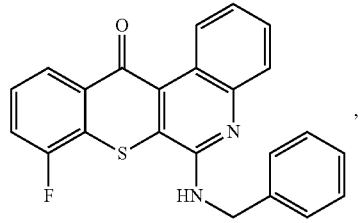
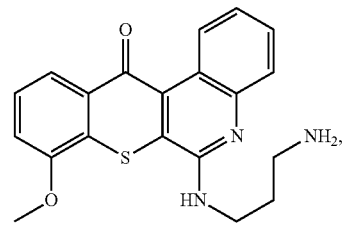
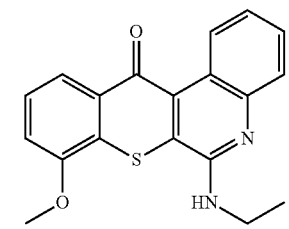
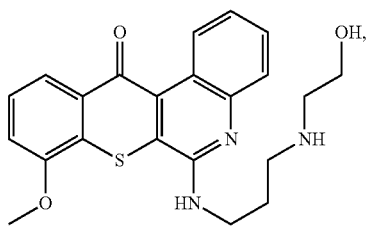
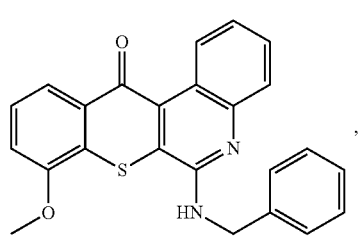
-continued
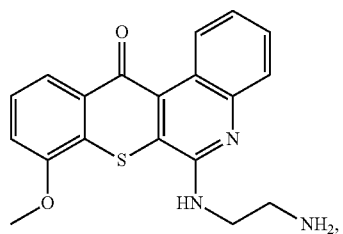
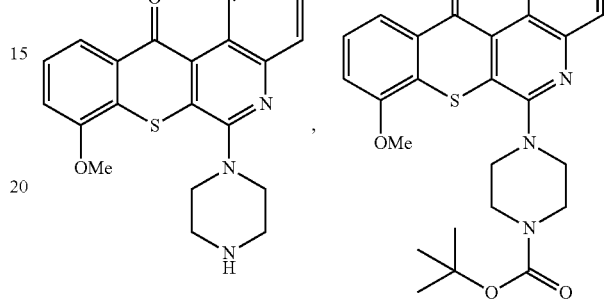
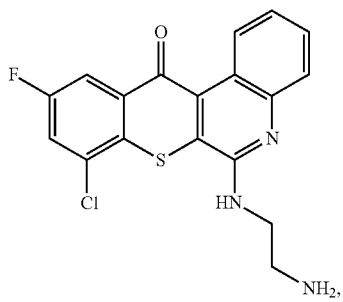
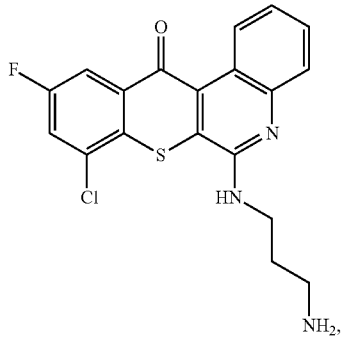
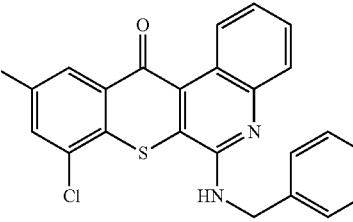
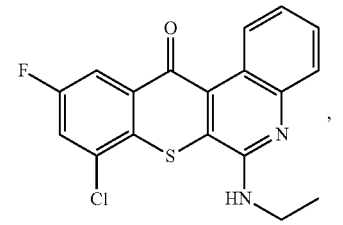

-continued
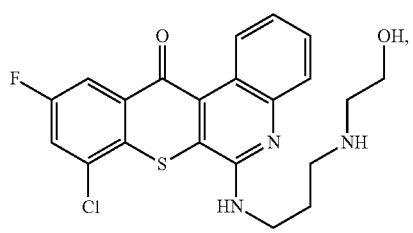
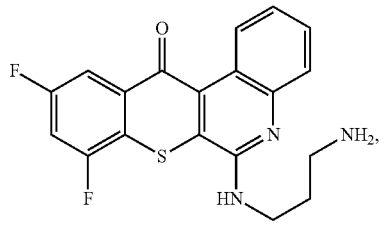
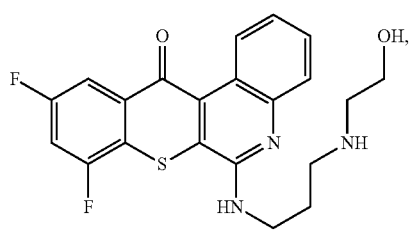
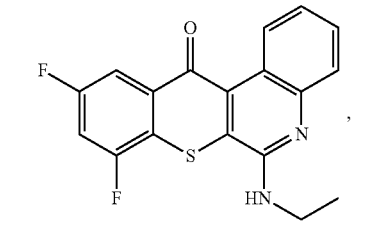
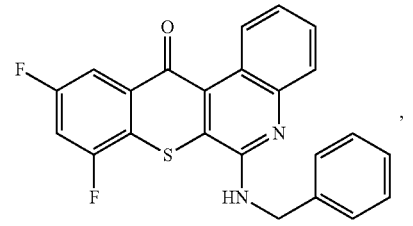
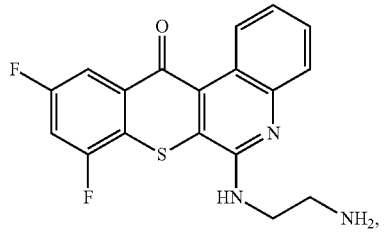
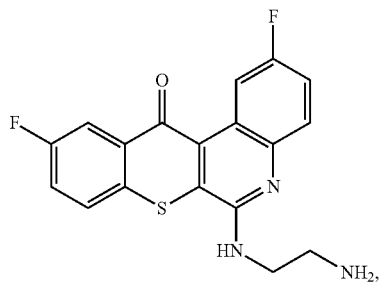
-continued
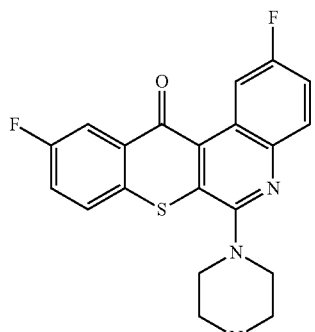
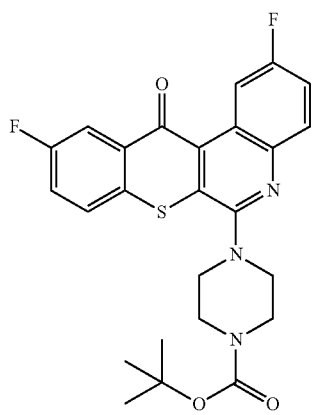
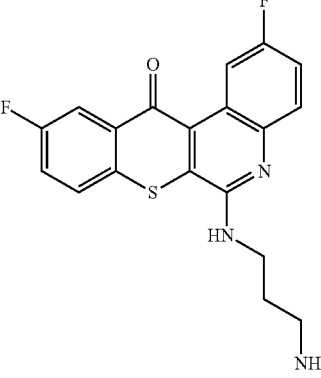
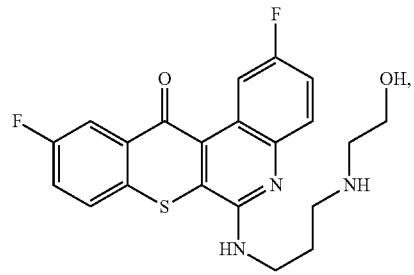
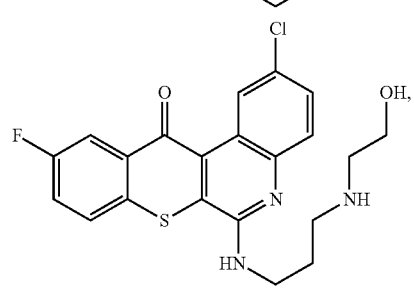

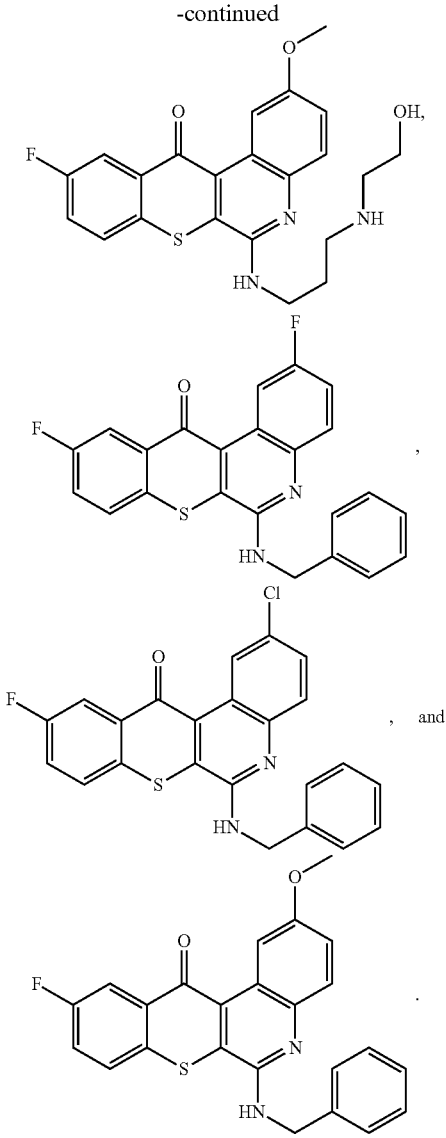

The present invention encompasses all stereoisomeric forms of the compounds of Formulae (I-1), (I-2), (I-3) and (I-4). Centers of asymmetry that are present in the compounds of Formulae (I-1), (I-2), (I-3) and (I-4) can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. When a particular configuration is depicted, that enantiomer (either (R) or (S), at that center) is intended. Similarly, when a compound name is recited without a chiral designation for a chiral carbon, it is understood that both the (R) and (S) configurations of the chiral carbon, and hence individual enantiomers and mixtures thereof, are embraced by the name.

The invention includes all possible enantiomers, regioisomers, and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formulae (I-1), (I-2), (I-3) and (I-4) or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL (microliters); mM (millimolar); M (micromolar); Hz (Hertz); MHz (megahertz); mmol (millimoles); hr or hrs (hours); min (minutes); MS (mass spectrometry); ESI (electrospray ionization); TLC (thin layer chromatography); and HPLC (high pressure liquid chromatography). For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

The compounds of Formulae (I-1), (I-2), (I-3) and (I-4) of the present invention are prepared according to general chemical synthetic procedures. The preparation of the embodiments of the compounds of the present invention is illustrated below. Suitable syntheses for compounds of the invention can be found in the Examples below.

In another aspect, the invention provides a pharmaceutical composition comprising a compound of any of formulae I-I to I-4, or a pharmaceutically acceptable ester, salt, or prodrug thereof, together with a pharmaceutically acceptable carrier.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gel caps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Tablets and capsules for oral administration are normally presented in unit dose form and contain conventional excipients such as binders, fillers (including cellulose, mannitol, lactose), diluents, tableting agents, lubricants (including magnesium stearate), detergents, disintegrants (e.g. polyvinylpyrrolidone and starch derivatives such as sodium glycolate starch), coloring agents, flavoring agents, and wetting agents (for example sodium lauryl sulfate).

The oral solid compositions can be prepared by conventional methods of blending, filling or tableting. The blending operation can be repeated to distribute the active principle throughout compositions containing large quantities of fillers. Such operations are conventional.

For parenteral administration fluid unit dosages can be prepared, containing the compound and a sterile vehicle. The compound can be either suspended or dissolved, depending on the vehicle and concentration. The parenteral solutions are normally prepared by dissolving the compound in a vehicle, sterilizing by filtration, filling suitable vials and sealing. Advantageously, adjuvants such as local anaesthetics, preservatives and buffering agents can also be dissolved in the vehicle. To increase the stability, the composition can be frozen after having filled the vials and removed the water under vacuum. Parenteral suspensions are prepared in substantially the same manner, except that the compound can be suspended in the vehicle instead of being dissolved, and sterilized by exposure to ethylene oxide before suspending in the sterile vehicle. Advantageously, a surfactant or wetting agent can be included in the composition to facilitate uniform distribution of the compound of the application.

Pharmaceutical preparation for administration by inhalation can be delivered from an insufflator or a nebulizer pressurized pack.

In another aspect, the present invention provides a method of inhibiting FLT3, comprising contacting a cell with a compound of the present invention.

In another aspect, the present invention provides a method of treating or preventing the disease associated with FLT3 inhibition in a subject, which comprises administrating an effective amount of a compound of the present invention.

The compounds of the invention are useful for treating or preventing any disease and/or condition, wherein FLT3 inhibition is desired. Inhibition of the enzyme can lead to attenuation of tumor growth. Thus, the invention provides methods for the treatment or prevention of tumors or cancers. Examples of cancer which can be treated in accordance with the present teachings include, but are not limited to invasive breast carcinoma, adenocarcinoma, lung cancer (non-small cell, squamous cell carcinoma, adenocarcinoma, and large cell lung cancer), liver cancer, colorectal cancer, brain, head and neck cancer (e.g., neuro/glioblastoma), breast cancer, ovarian cancer, transitional cell carcinoma of the bladder, prostate cancer, oral squamous cell carcinoma, bone sarcoma, adrenocortical cancer, gastrointestinal tumors including colorectal cancer, biliary tract cancer such as gallbladder carcinoma (GBC), bladder cancer, esophageal cancer, gastric cancer, cervical cancer, salivary gland cancer, diarrhea benign neoplasm, ductal carcinoma in situ, paronychia, cholangiocarcinoma, kidney cancer, pancreatic cancer, medulloblastoma, glioblastoma, luminal, HER2-positive and triple negative mammary tumors, hematologic malignancies and leukemia (acute myelogenous leukemia (AML), B-precursor cell acute lymphoblastic leukemia (ALL), a fraction of T-cell ALL, and chronic myelogenous leukemia (CML)).

The compounds, or pharmaceutically acceptable salts thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

The invention having now been described by way of written description, those of skill in the art will recognize that the invention can be practiced in a variety of embodiments and that the foregoing description and examples below are for purposes of illustration and not limitation of the claims that follow.

Examples

All the key raw materials were purchased from various commercial sources and used without further purification. Some of the key raw materials and reagents were available in-house. $^1$H NMR spectra were recorded on 400 MHz NMR spectrometer using DMSO-$d_6$, CDCl$_3$ or TFA-$d_1$ as deuterated solvent. LC-MS analysis of the compounds was conducted as per one of the following methods A-K.

Method A.

Column: Symmetry—C18 4.6×75 mm, 3.5 am; wavelength: 254 nm; flow: 0.8 mL/min; run time: 12 min; Time & mobile phase-gradient (time in min/B): 0/50, 3/95, 9/95, 10/50, 12/50 [B: Acetonitrile; A: Ammonium formate (20 millimolar in water)]; LC—Agilent technologies—1260 Infinity II Series; MASS: Agilent technologies—6120 Quadrupole LC/MS-API-ESI.

Method B.

Column: Symmetry—C18 4.6×75 mm, 3.5 am; wavelength: 254 nm; flow: 0.8 mL/min; run time: 10 min; Time & mobile phase-gradient (time in min/B): 0/5, 2/95, 7/95, 7.1/5, 10/5 [B: Acetonitrile; A: 0.1% formic acid in water]; LC—Agilent technologies—1260 Infinity II Series; MASS: Agilent technologies—6120 Quadrupole LC/MS-API-ESI.

Method C.

Column: Symmetry—C18 4.6×75 mm, 3.5 am; wavelength: 254 nm; flow: 0.8 mL/min; run time: 12 min; Time & mobile phase-gradient (time in min/B): 0/50, 3/95, 9/95, 10/50, 12/50 [B: Acetonitrile; A: Ammonium formate (10 millimolar in water)]; LC—Agilent technologies—1260 Infinity II Series; MASS: Agilent technologies—6120 Quadrupole LC/MS-API-ESI.

Method D.

Column: Agilent poroshell 120 EC—C18 3.0×50 mm, 2.7 am; wavelength: 254 nm; flow: 0.8 mL/min; run time: 12 min; Time & mobile phase-gradient (time in min/B): 0/50, 3/95, 9/95, 10/50, 12/50 [B: Acetonitrile; A: Ammonium formate (20 mmol in water)]; LC—Agilent technologies—1260 Infinity II Series; MASS: Agilent technologies—6120 Quadrupole LC/MS-API-ESI.

Method E.

Column:—Agilent poroshell 120 EC—C18 4.6×100 mm, 2.7 m; wavelength: 254 nm; flow: 0.8 mL/min; run time: 12 min; Time & mobile phase-gradient (time in min/B): 0/50, 3/95, 9/95, 10/50, 12/50 [B: Acetonitrile; A: Ammonium formate (20 millimolar in water)]; LC—Agilent technologies—1260 Infinity II Series; MASS: Agilent technologies—6120 Quadrupole LC/MS-API-ESI.

Method F.

Agilent poroshell 120 EC—C18 4.6×100 mm, 2.7 m; wavelength: 254 nm; flow: 0.8 mL/min; run time: 10 min; Time & mobile phase-gradient (time in min/B): 0/10, 3/80 7/80, 7.01/10, 10/10 [B: Acetonitrile; A: Ammonium formate (20 millimolar in water)]; LC—Agilent technologies—1260 Infinity II Series; MASS: Agilent technologies—6120 Quadrupole LC/MS-API-ESI.

Method G.

Agilent poroshell 120 EC—C18 4.6×100 mm, 2.7 m; wavelength: 254 nm; flow: 0.8 mL/min; run time: 12 min; Time & mobile phase-gradient (time in min/B): 0/20, 3/90 10/90, 10.1/20, 12/20 [B: Acetonitrile; A: Ammonium formate (20 millimolar in water)]; LC—Agilent technologies—1260 Infinity II Series; MASS: Agilent technologies—6120 Quadrupole LC/MS-API-ESI.

Method H.

Agilent poroshell 120 EC—C18 4.6×100 mm, 2.7 m; wavelength: 254 nm; flow: 0.8 mL/min; run time: 10 min; Time & mobile phase-gradient (time in min/B): 0/5, 2/95, 7/95, 7.1/5, 10/5 [B: Acetonitrile; A: 0.1% formic acid in water]; LC—Agilent technologies—1260 Infinity II Series; MASS: Agilent technologies—6120 Quadrupole LC/MS-API-ESI.

Method I.

Agilent poroshell 120 EC—C18 4.6×100 mm, 2.7 m; wavelength: 254 nm; flow: 0.8 mL/min; run time: 8 min; Time & mobile phase-gradient (time in min/B): 0/20, 2/90 6/90, 6.5/20, 8/20 [B: Acetonitrile; A: Ammonium formate (20 millimolar in water)]; LC—Agilent technologies—1260 Infinity II Series; MASS: Agilent technologies—6120 Quadrupole LC/MS-API-ESI.

Method J.

Column:—Agilent poroshell 120 EC—C18 4.6×100 mm, 2.7 μm; wavelength: 254 nm; flow: 0.8 mL/min; run time: 12 min; Time & mobile phase-gradient (time in min/B): 0/50, 3/95, 9/95, 10/50, 12/50 [B: Acetonitrile; A: Ammonium formate (20 millimolar in water)]; LC—Agilent technologies—1260 Infinity II Series; MASS: Agilent technologies—6120 Quadrupole LC/MS-API-ESI.

Method K:

Column:—Symmetry—C18, 4.6×75 mm, 3.5 m; wavelength: 254 nm; flow: 0.8 mL/min; run time: 12 min; Time & mobile phase-gradient (time in min/B): 0/50, 3/95, 9/95, 10/50, 12/50 [B: Acetonitrile; A: Ammonium formate (20 millimolar in water)]; LC—Agilent technologies—1260 Infinity II Series; MASS: Agilent technologies—6120 Quadrupole LC/MS-API-ESI.

PREPARATION EXAMPLES

General Procedure A;

Step-1: An aqueous solution of chloroacetic acid (1.1 eq.) and aq. NaOH [3.0 eq. dissolved in ~2 vol. of water] were simultaneously added to a solution of corresponding substituted thiophenol (1.0 eq.) in water, and the mixture was heated to 50° C. for 4-5 hrs. After completion of reaction, as monitored by TLC, the reaction mass was cooled to room temperature and slowly diluted with 5N HCl (pH~4-5). The resulting suspension was filtered; washed with water and vacuum dried to afford series 2 [compounds 2a-2o] as off-white solids.

General Procedure B;

Step-2: A mixture of isatin (0.9 eq.), series 2 (1.0 eq.) and sodium acetate (0.2 eq.) in AcOH (4-5 vol.) was heated at 150° C. for 24 hrs. After cooling, the solid formed was suspended with acetic acid (10 vol.); filtered and washed with Acetic acid: water (1:9) to remove unreacted isatin. The remaining solid was again washed with water and dried under vacuum to afford series 3 [compounds 3a-3o].

General Procedure C;

Step-3: A solution of series 3 in $POCl_3$ (3-4 vol.) was heated at 160° C. for 48 h. After cooling, the mixture was carefully poured into ice at 0° C. The resulting precipitate that separated was collected by filtration. The filtered cake was suspended in 10% $NaHCO_3$ solution and stirred vigorously for 1 h. The resulting precipitate was collected and washed with $H_2O$. The crude solid was washed with EtOAc: THF mixture (1:1) and vacuum dried to afford the following scaffold compounds.

General Procedure D:

A mixture of series 4 (1.0 eq.), amine (5.0 eq.) in DMSO (~4-5 vol.) was heated at 120° C. for 2-3 hrs in a reaction flask (Note: reaction was performed in sealed tube in case of targets involving usage of amines with b.ps<120° C.). After completion of the reaction, as monitored by TLC, reaction mass was cooled to RT and quenched in water. Resulting precipitate was diluted with 10% MeOH/DCM mixture and extracted. The aqueous layer separated was reextracted with 10% MeOH/DCM. The combined organic extract was washed with brine solution; dried over anhydrous $Na_2SO_4$ and concentrated to give the crude compounds. The crude mixtures were either crystallized or purified by FCC using MeOH/DCM/aq. $NH_3$ mixtures to afford target compounds as pale yellow to yellow solids.

General Procedure E:

A suspension of series 4 (1.0 eq.) in DMSO (~4-5 vol.) was added dropwise to a stirred solution of amine (5.0 eq.) in DMSO (~5 vol.) at 120° C. and the mixture was heated at same temperature for 2-3 hrs. After completion of the reaction, as monitored by TLC, reaction mass was cooled to RT and quenched in water. Resulting precipitate was diluted with 10% MeOH/DCM mixture and extracted. The aqueous layer was separated and reextracted with 10% MeOH/DCM. The combined organic extract was washed with brine solution; dried over anhydrous $Na_2SO_4$ and concentrated to give the crude compounds. The crude mixtures were purified by FCC using MeOH/DCM/aq. $NH_3$ mixtures to afford target compounds as pale yellow to yellow solids.

General Procedure F:

A mixture of series 4 (1.0 eq.), 4-methoxybenzylamine (5.0 eq.) in DMSO (~4-5 vol.) was heated at 120° C. for 2-3 hrs. After completion of the reaction, as monitored by TLC, reaction mass was cooled to RT and quenched in water. Resulting precipitate was filtered; washed with water and vacuum dried to afford crude products, which were purified by FCC using MeOH/DCM mixtures to afford series 4 as pale yellow to yellow solids. A mixture of TFA (~10 vol.) and series 4 (1.0 eq.) was stirred at RT for 4-5 hrs. After completion of the reaction, as monitored by TLC, reaction mass was concentrated on rotary evaporator. Resulting residue was quenched with ice-cold water and resulting solid was filtered. The filtered cake was suspended in saturated $NaHCO_3$ solution (pH~8) and stirred for 30 min. The suspension was filtered; washed with water and vacuum dried to afford target compounds as pale yellow to yellow solids.

General Procedure G:

series 4 (1.0 eq.) was added to a stirred mixture of $Na_2CO_3$ (3.0 eq.), ethylene glycol (5.0 eq.) in DMSO (~4-5 vol.) at RT, and the mixture was heated at 120° C. for 2-3 hrs in a reaction flask. After completion of the reaction, as monitored by TLC, reaction mass was cooled to RT and quenched in water. Resulting precipitate was diluted with 10% MeOH/DCM mixture and extracted. The aqueous layer separated was reextracted with 10% MeOH/DCM. The combined organic extract was washed with brine solution; dried over anhydrous $Na_2SO_4$ and concentrated to give the crude compounds. The crude mixtures were either crystallized or purified by FCC to afford target compounds as pale yellow to yellow solids.

General Procedure H:

$Pd(OAc)_2$ (0.05 eq.) followed by appropriate amine (1.0 eq.) were added to a degassed solution of series 4 (1.1 eq.), $CS_2CO_3$ (1.6 eq.), BINAP (0.1 eq.) in NMP (5 ml) at RT and the mixture was refluxed for 2 hrs. After completion of reaction (as monitored by TLC), the reaction mixture was cooled to RT and filtered through celite. The filtrate was diluted with water (30 ml) and extracted in 10% MeOH/DCM (3×30 ml). The combined organic extract was washed with water (25 ml), followed by brine solution (25 ml). The organic layer was dried over anhydrous $Na_2SO_4$ and concentrated to a residue, which was purified by FCC to afford target compounds as pale yellow to yellow solids.

General Procedure I:

Ethyl iodide or benzyl chloride (1.5 eq.) was added to a stirred mixture of compound (1.0 eq.), $K_2CO_3$ (2.1 eq.), in DMF (~4-5 vol.) at RT, and the mixture was stirred at RT. After completion of the reaction, as monitored by TLC, reaction mass was quenched in water. Resulting suspension was diluted with 10% MeOH/DCM mixture and extracted. The aqueous layer separated was reextracted with 10% MeOH/DCM. The combined organic extract was washed with brine solution; dried over anhydrous $Na_2SO_4$ and concentrated to give the crude compounds. The crude mixtures were purified by FCC to afford target compounds as pale yellow to yellow solids.

General Procedure J:

Series 4 (1.0 eq.) was added to a stirred mixture of TEA (10.0 eq.) and ethylamine.HCl (10.0 eq.) in DMSO (~4-5 vol.) at RT, and the mixture was heated at 120° C. for 2-3 hrs in a sealed tube. After completion of the reaction, as monitored by TLC, reaction mass was cooled to RT and quenched in water. Resulting precipitate was diluted with EtOAc and extracted. The aqueous layer separated was reextracted with EtOAc. The combined organic extract was washed with brine solution; dried over anhydrous $Na_2SO_4$ and concentrated to give the crude compounds. The crude mixtures were purified by FCC to afford target compounds as pale yellow to yellow solids.

General Procedure K:

6-amino derivatives (1.0 eq.) was added to a stirred mixture of CDI (1.5 eq.) and benzoic acid analogues (1.2 eq.) in DMSO (~4-5 vol.) at 70° C. and continued stirring at same temperature for 30 mins. The temperature was raised to 140° C. and the reaction mixture was further stirred at same temperature for 16 hrs. After completion of the reaction, as monitored by TLC, reaction mass was cooled to RT and quenched into water. Resulting precipitate was diluted with 10% MeOH/DCM mixture and extracted. The aqueous layer separated was reextracted with 10% MeOH/DCM. The combined organic extract was washed with brine solution; dried over anhydrous $Na_2SO_4$ and concentrated to give the crude compound. The crude mixture was purified by FCC using MeOH/DCM/aq. $NH_3$ mixtures to afford target compound as yellow solid.

General Procedure L:

m-CPBA (5.0 eq.) was added to a stirred mixture of series 4 (1.0 eq.) in chloroform (~200 vol.) at RT, and the mixture was stirred at RT for 16-20 hrs. After completion of the reaction, as monitored by TLC, the solvent was concentrated. The crude product was purified by FCC to afford target compound 5a as pale yellow solid.

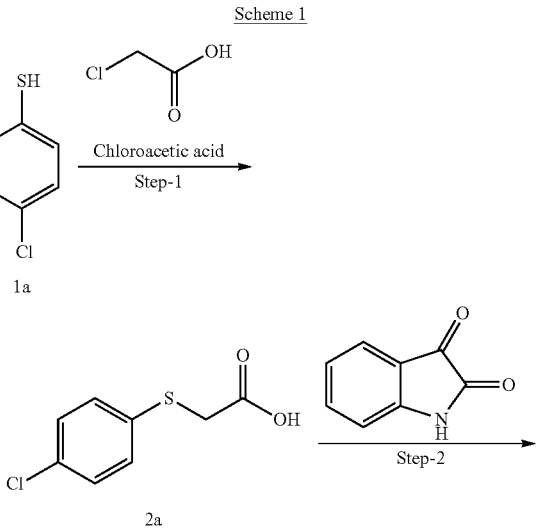

Scheme 1

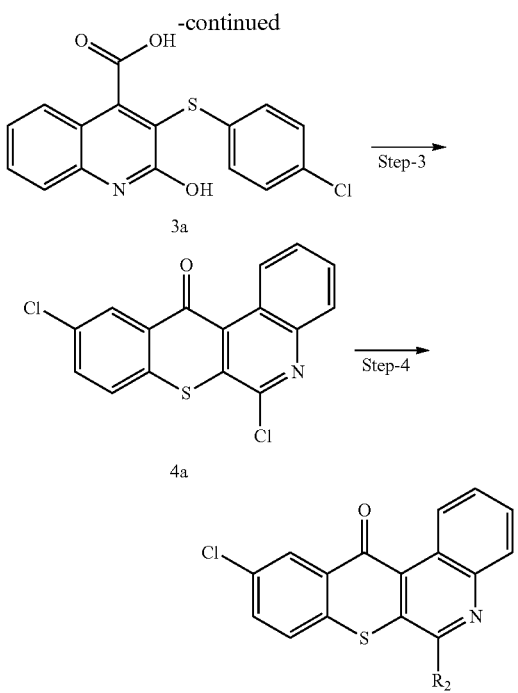

Example 1 6-chloro-10-fluoro-12H-thiochromeno[2,3-c]quinolin-12-one (4a)

Synthesized starting from 4-chlorothiophenol in 3 steps following general procedures A-C. Yield: 46% over 3 steps. ES-MS [M+1]$^+$: 331.8; $t_R$: 6.95 min (method-A).

Example 2 10-chloro-6-((4-methoxybenzyl)amino)-12H-thiochromeno[2,3-c]quinolin-12-one (7700)

Synthesized according to general procedure-E. Yield: 300 mg (92%). ES-MS [M+1]$^+$: 432.9; $t_R$: 6.31 min (method-A), $^1$H NMR (400 MHz, DMSO-d$_6$): δ 9.33 (d, J=8.4 Hz, 1H), 8.36 (d, J=2.4 Hz, 1H), 7.98 (d, J=9.2 Hz, 1H), 7.87 (dd, J=8.4, 2.4 Hz, 1H), 7.71 (m, 1H), 7.66 (d, J=7.6 Hz, 1H), 7.59 (m, 1H), 7.39, 7.36 (m, 1H), 6.84 (d, J=8.4 Hz, 2H), 4.70 (d, J=5.6 Hz, 1H), 3.67 (s, 3H).

Example 3 6-Amino-10-chloro-12H-thiochromeno[2,3-c]quinolin-12-one (7702)

Synthesized according to general procedure-F. Yield: 195 mg (81%). ES-MS [M+1]$^+$: 312.9; $t_R$: 4.29 min (method-A); $^1$HNMR (400 MHz, TFA-d): δ 9.48 (d, J=8.4 Hz, 1H), 8.73 (s, 1H), 8.00-7.85 (m, 5H).

Example 4 10-chloro-6-(propylamino)-12H-thiochromeno[2,3-c]quinolin-12-one (7703)

Synthesized according to general procedure-D. Yield: 120 mg (75%). ES-MS [M+1]$^+$: 355.0; $t_R$: 6.84 min (method-A); $^1$H NMR (400 MHz, DMSO-d$_6$): δ 9.33 (d, J=8.4 Hz, 1H), 8.37 (d, J=2.0 Hz, 1H), 7.97 (d, J=8.4 Hz, 1H), 7.87 (dd, J=8.4, 2.0 Hz, 1H), 7.66 (d, J=8.4 Hz, 1H), 7.57 (ddd, J=8.4, 6.8, 1.2 Hz, 1H), 7.35 (ddd, J=8.4, 6.8, 1.2 Hz, 1H), 7.12 (dd, J=5.6, 4.8 Hz, 1H), 3.52 (q, J=6.0 Hz, 2H), 1.70 (m, 2H), 0.95 (t, J=7.2 Hz, 3H).

Example 5 6-(3-aminopropylamino)-10-chloro-12H-thiochromeno[2,3-c]quinolin-12-one (7704)

Synthesized according to general procedure-E. Yield: 295 mg (88%). ES-MS [M+1]$^+$: 370.0; $t_R$: 2.52 min (method-A); $^1$H NMR (400 MHz, DMSO-d$_6$): δ 9.34 (d, J=8.4 Hz, 1H), 8.38 (d, J=1.2 Hz, 1H), 7.98 (d, J=8.8 Hz, 1H), 7.88 (dd, J=8.4, 1.6 Hz, 1H), 7.69 (d, J=8.0 Hz, 1H), 7.60 (dd, J=8.4, 6.8, 1H), 7.35 (dd, J=8.0, 7.2, 1H), 6.5 (brs, 2H), 3.66 (m, 2H), 2.83 (t, J=6.8 Hz, 2H), 1.91 (t, J=6.8 Hz, 2H).

Example 6 10-chloro-6-(3-(2-hydroxyethylamino)propylamino)-12H-thiochromeno[2,3-c]quinolin-12-one (7701)

Synthesized according to general procedure-D. Yield: 328 mg (55%). ES-MS [M+1]$^+$: 413.9; $t_R$: 2.89 min (method-B); $^1$H NMR (400 MHz, DMSO-d$_6$): δ 9.33 (d, J=8.8 Hz, 1H), 8.36 (d, J=2.0 Hz, 1H), 7.93 (d, J=8.4 Hz, 1H), 7.88 (dd, J=8.8, 2.0 Hz, 1H), 7.66 (d, J=8.0 Hz, 1H), 7.58 (dd, J=8.0, 7.2 Hz, 1H), 7.35 (t, J=7.6, 1H), 4.57 (brs, 1H), 3.62 (t, J=6.4 Hz, 2H), 3.55 (m, 2H), 2.71 (t, J=6.0 Hz, 2H), 2.63 (t, J=5.6 Hz, 2H), 1.82 (t, J=6.0 Hz, 2H).

Example 7 10-chloro-6-(2-hydroxyethylamino)-12H-thiochromeno[2,3-c]quinolin-12-one (7717)

Synthesized according to general procedure-D. Yield: 213 mg (58%). ES-MS [M+1]$^+$: 356.9; $t_R$: 4.21 min (method-A); $^1$H NMR (400 MHz, DMSO-d$_6$): δ 9.30 (d, J=8.4 Hz, 1H), 8.32 (d, J=2.4 Hz, 1H), 7.95 (d, J=8.4 Hz, 1H), 7.84 (dd, J=8.4, 2.0 Hz, 1H), 7.64 (d, J=8.0 Hz, 1H), 7.57 (ddd, J=8.4, 8.0, 1.2 Hz, 1H), 7.35 (ddd, J=8.4, 8.0, 1.2 Hz, 1H), 6.93 (t, J=4.8 Hz, 1H), 4.84 (t, J=5.6 Hz, 1H), 3.66 (m, 4H).

Example 8 10-chloro-6-(2-hydroxyethoxy)-12H-thiochromeno[2,3-c]quinolin-12-one (7718)

Synthesized according to general procedure-G. Yield: 150 mg (56%). ES-MS [M+1]$^+$: 357.9; $t_R$: 4.73 min (method-A); $^1$H NMR (400 MHz, DMSO-d$_6$): δ 9.50 (d, J=8.4 Hz, 1H), 8.33 (d, J=2.4 Hz, 1H), 8.04 (d, J=8.8 Hz, 1H), 7.86-7.81 (m, 2H), 7.70 (dd, J=6.8, 4.8 Hz, 1H), 7.59 (t, J=8.0 Hz, 1H), 4.93 (t, J=5.6 Hz, 1H), 4.60 (t, J=5.2 Hz, 2H), 3.85 (t, J=5.2 Hz, 2H).

Example 9 10-chloro-6-(3-hydroxypropylamino)-12H-thiochromeno[2,3-c]quinolin-12-one (7719)

Synthesized according to general procedure-D. Yield: 218 mg (78%). ES-MS [M+1]$^+$: 370.9; $t_R$: 4.43 min (method-A); $^1$H NMR (400 MHz, DMSO-d$_6$): δ 9.32 (d, J=8.4 Hz, 1H), 8.35 (d, J=2.4 Hz, 1H), 7.97 (d, J=8.4 Hz, 1H), 7.86 (dd, J=8.4, 2.4 Hz, 1H), 7.65 (d, J=8.4 Hz, 1H), 7.57 (t, J=8.0, 1H), 7.35 (dd, J=8.0, 7.2 Hz, 1H), 7.13 (t, J=4.8 Hz, 1H), 4.65 (dd, J=5.2, 4.8 Hz, 1H), 3.62 (q, J=6.0 Hz, 2H), 3.55 (q, J=5.6 Hz, 2H), 1.84 (quint, J=6.4 Hz, 2H).

Example 10 10-chloro-6-(3-methoxypropylamino)-12H-thiochromeno[2,3-c]quinolin-12-one (7720)

Synthesized according to general procedure-D. Yield: 160 mg (55%). ES-MS [M+1]$^+$: 384.9; $t_R$: 6.12 min (method-A); $^1$H NMR (400 MHz, DMSO-d$_6$): δ 9.31 (d, J=8.4 Hz, 1H), 8.33 (d, J=2.4 Hz, 1H), 7.96 (d, J=8.4 Hz, 1H), 7.84 (dd, J=8.4, 2.4 Hz, 1H), 7.64 (d, J=8.4 Hz, 1H), 7.56 (ddd, J=8.4, 8.0, 1.2 Hz, 1H), 7.34 (ddd, J=8.4, 8.0, 1.2 Hz, 1H), 7.12 (t, J=4.8 Hz, 1H), 3.59 (q, J=6.8 Hz, 2H), 3.46 (dd, J=6.4, 6.0 Hz, 2H), 3.26 (s, 3H), 1.92 (quint, J=6.4 Hz, 2H).

Example 11 10-chloro-6-(3-(methylamino)propylamino)-12H-thiochromeno[2,3-c]quinolin-12-one (7721)

Synthesized according to general procedure-D. Yield: 162 mg (56%). ES-MS [M+1]$^+$: 384.0; $t_R$: 4.12 min (method-A); $^1$H NMR (400 MHz, DMSO-d$_6$): δ 9.32 (d, J=8.8 Hz, 1H), 8.36 (d, J=2.0 Hz, 1H), 7.97 (d, J=8.8 Hz, 1H), 7.87 (dd, J=8.4, 2.4 Hz, 1H), 7.67 (d, J=8.4 Hz, 1H), 7.58 (dd, J=8.0, 7.2 Hz, 1H), 7.36 (dd, J=8.0, 7.2 Hz, 1H), 3.63 (t, J=6.4 Hz, 2H), 2.80 (dd, J=7.2, 6.4 Hz, 2H), 2.43 (s, 3H), 1.91 (quint, J=6.4 Hz, 2H).

Example 12 10-chloro-6-(3-(dimethylamino)propylamino)-12H-thiochromeno[2,3-c]quinolin-12-one (7722)

Synthesized according to general procedure-D. Yield: 275 mg (92%). ES-MS [M+1]$^+$: 398.0; $t_R$: 5.76 min (method-A); $^1$H NMR (400 MHz, DMSO-d$_6$): δ 9.34 (d, J=8.0 Hz, 1H), 8.39 (s, 1H), 8.05 (d, J=8.4 Hz, 1H), 7.90 (m, 2H), 7.66 (d, J=8.0 Hz, 1H), 7.58 (dd, J=8.0, 7.2 Hz, 1H), 7.36 (dd, J=8.0, 7.6 Hz, 1H), 3.60 (q, J=4.8 Hz, 2H), 2.41 (m, 2H), 2.24 (s, 6H), 1.82 (quint, J=6.4 Hz, 2H).

Example 13 10-chloro-6-(ethylamino)-12H-thiochromeno[2,3-c]quinolin-12-one (7736)

Synthesized according to general procedure-D. Yield: 200 mg (49%). ES-MS [M+1]$^+$: 340.9; $t_R$: 6.09 min (method-C); $^1$H NMR (400 MHz, DMSO-d$_6$): δ 9.31 (d, J=7.6 Hz, 1H), 8.33 (d, J=2.0 Hz, 1H), 7.93 (d, J=8.8 Hz, 1H), 7.83 (dd, J=8.4, 2.4 Hz, 1H), 7.65 (d, J=8.0 Hz, 1H), 7.56 (ddd, J=8.0, 6.8, 1.2 Hz, 1H), 7.33 (ddd, J=8.4, 6.8, 1.2 Hz, 1H), 7.10 (dd, J=5.2, 4.8 Hz, 1H), 3.57 (m, 2H), 1.25 (t, J=7.2 Hz, 3H).

Example 14 6-(Benzylamino)-10-chloro-12H-thiochromeno[2,3-c]quinolin-12-one (7737)

Synthesized according to general procedure-D. Yield: 205 mg (68%). ES-MS [M+1]$^+$: 403.0; $t_R$: 6.51 min (method-A); $^1$H NMR (400 MHz, DMSO-d$_6$): δ 9.33 (d, J=8.4 Hz, 1H), 8.38 (d, J=2.4 Hz, 1H), 8.00 (d, J=8.8 Hz, 1H), 7.88 (dd, J=8.8, 2.4 Hz, 1H), 7.82 (dd, J=6.0, 5.2 Hz, 1H), 7.62 (d, J=8.0 Hz, 1H), 7.56 (ddd, J=8.0, 6.8, 1.2 Hz, 1H), 7.44 (d, J=7.6 Hz, 2H), 7.36 (dt, J=6.8, 1.2 Hz, 1H), 7.28 (dd, J=8.0, 7.2 Hz, 2H), 4.79 (d, J=5.6 Hz, 2H).

Example 15 6-(2-aminoethylamino)-10-cholor-12H-thiochromeno[2,3-c]quinolin-12-one (7767)

Synthesized according to general procedure-E starting from scaffold compound 4a. ES-MS [M+1]$^+$: 356.1; 1H NMR (400 MHz, DMSO-d$_6$): δ 9.32 (1H, d, J=8.4 Hz), 8.35 (1H, br), 7.96 (1H, d, J=8.8 Hz), 7.85 (1H, t, J=7.2 Hz), 7.66 (1H, d, J=8.0 Hz), 7.59 (1H, t, J=8.0 Hz), 7.36 (1H, t, J=8.0 Hz), 3.59 (2H, t, J=6.0 Hz), 2.90 (2H, t, J=6.0 Hz).

Example 16 N-(10-chloro-12-oxo-12H-thiochromeno[2,3-c]quinolin-6-yl)picolinamide (7801)

Synthesized according to general procedure-K with 7702. Yield: 120 mg (36%). ES-MS [M+1]$^+$: 417.9; $t_R$: 4.77 min (method-A), $^1$H NMR (400 MHz, DMSO-d$_6$): δ 11.45 (s, 1H), 9.68 (dd, J=8.4, 2.0 Hz, 1H), 8.82 (d, J=4.8 Hz, 1H), 8.42 (d, J=2.0 Hz, 1H), 8.17 (d, J=7.6 Hz, 1H), 8.13-8.08 (m, 3H), 7.90-7.84 (m, 3H), 7.76 (dd, J=6.4, 4.8 Hz, 1H).

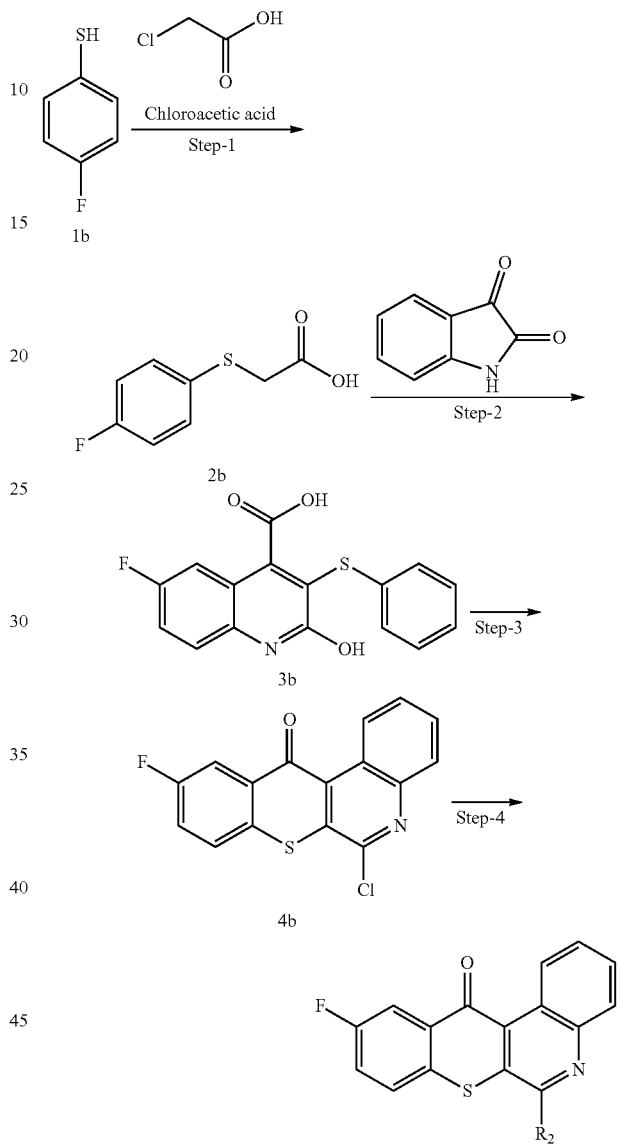

Example 17 6-chloro-10-fluoro-12H-thiochromeno[2,3-c]quinolin-12-one (4b)

Synthesized starting from 4-fluorothiophenol in 3 steps following general procedures A-C. Yield: 54% over 3 steps. ES-MS [M+1]$^+$: 315.9; tR: 5.84 min (method-A).

Example 18 6-amino-10-fluoro-12H-thiochromeno[2,3-c]quinolin-12-one (7705)

Synthesized according to general procedure-F. Yield: 165 mg (92%). ES-MS [M+1]$^+$: 297.0; $t_R$: 3.53 min (method-A); $^1$H NMR (400 MHz, DMSO-d$_6$): δ 9.41 (d, J=8.4 Hz, 1H), 8.17 (dd, J=9.6, 2.4 Hz, 1H), 8.04 (dd, J=8.8, 5.2 Hz, 1H), 7.78 (ddd, J=8.4, 8.0, 2.8 Hz, 1H), 7.66-7.58 (m, 2H), 7.39 (dd, J=8.0, 7.2 Hz, 1H), 7.08 (brs, 2H).

Example 19 10-fluoro-6-(propylamino)-12H-thiochromeno[2,3-c]quinolin-12-one (7706)

Synthesized according to general procedure-D. Yield: 190 mg (71%). ES-MS [M+1]$^+$: 339.0; $t_R$: 5.87 min (method-A); $^1$H NMR (400 MHz, DMSO-d$_6$): δ 9.38 (d, J=8.4 Hz, 1H), 8.17 (dd, J=9.6, 2.8 Hz, 1H), 8.06 (m, 1H), 7.79 (td, J=8.4, 2.8 Hz, 1H), 7.69 (d, J=7.4 Hz, 1H), 7.61 (t, J=7.0 Hz, 1H), 7.37 (t, J=7.0 Hz, 1H), 7.13 (t, J=5.2 Hz, 1H), 3.55 (q, J=6.4 Hz, 2H), 1.74 (q, J=7.2 Hz, 2H), 0.97 (t, J=7.2 Hz, 3H).

Example 20 6-(3-aminopropylamino)-10-fluoro-12H-thiochromeno[2,3-c]quinolin-12-one (7707)

Synthesized according to general procedure-E. Yield: 210 mg (75%). ES-MS [M+1]$^+$: 354.0; $t_R$: 2.35 min (method-A); $^1$H NMR (400 MHz, DMSO-d$_6$): δ 9.36 (d, J=8.4 Hz, 1H), 8.15 (dd, J=9.6, 2.8 Hz, 1H), 8.02 (dd, J=8.8, 5.2 Hz, 1H), 7.76 (ddd, J=8.8, 8.0, 2.8 Hz, 1H), 7.68 (d, J=8.0 Hz, 1H), 7.58 (dd, J=7.2, 6.8 Hz, 1H), 7.36 (t, J=7.2 Hz, 1H), 3.65 (t, J=6.8 Hz, 2H), 2.78 (t, J=6.8 Hz, 2H), 1.86 (quint, J=6.8 Hz, 2H).

Example 21 10-fluoro-6-(3-(2-hydroxyethylamino)propylamino)-12H-thiochromeno[2,3-c]quinolin-12-one (7708)

Synthesized according to general procedure-D. Yield: 260 mg (69%). ES-MS [M+1]$^+$: 398.0; $t_R$: 2.42 min (method-A); $^1$H NMR (400 MHz, DMSO-d$_6$): δ 9.36 (d, J=8.4 Hz, 1H), 8.14 (dd, J=9.6, 2.8 Hz, 1H), 8.00 (dd, J=8.8, 4.8 Hz, 1H), 7.76 (ddd, J=8.8, 8.4, 2.8 Hz, 1H), 7.67 (d, J=8.0 Hz, 1H), 7.58 (d, J=7.2, 1H), 7.35 (dd, J=7.6, 7.2 Hz, 1H), 4.81 (brs, 1H), 3.63 (t, J=6.4 Hz, 2H), 3.57 (t, J=5.6 Hz, 2H), 2.82 (t, J=6.4 Hz, 2H), 2.75 (dd, J=6.0, 5.2 Hz, 2H), 1.90 (quint, J=6.4 Hz, 2H).

Example 22 10-fluoro-6-(2-hydroxyethylamino)-12H-thiochromeno[2,3-c]quinolin-12-one (7727)

Synthesized according to general procedure-D. Yield: 180 mg (55%). ES-MS [M+1]$^+$: 340.9; $t_R$: 3.55 min (method-C); $^1$H NMR (400 MHz, DMSO-d$_6$): δ 9.32 (d, J=7.6 Hz, 1H), 8.09 (dd, J=9.6, 2.8 Hz, 1H), 8.00 (dd, J=8.8, 5.2 Hz, 1H), 7.73 (ddd, J=8.8, 8.4, 2.8 Hz, 1H), 7.65 (d, J=7.6 Hz, 1H), 7.57 (ddd, J=8.4, 7.6, 1.6 Hz, 1H), 7.34 (dt, J=8.4, 1.6 Hz, 1H), 6.97 (brs, 1H), 3.70-3.64 (m, 4H).

Example 23 10-fluoro-6-(2-hydroxyethoxy)-12H-thiochromeno[2,3-c]quinolin-12-one (7728)

Synthesized according to general procedure-D. Yield: 180 mg (33%). ES-MS [M+1]$^+$: 342.0; $t_R$: 4.09 min (method-C); $^1$H NMR (400 MHz, DMSO-d$_6$): δ 9.56 (dd, J=8.4, 1.2 Hz, 1H), 8.16-8.11 (m, 2H), 7.84 (ddd, J=8.4, 8.0, 1.2 Hz, 1H), 7.79-7.69 (m, 2H), 7.59 (ddd, J=7.2, 6.8, 1.2 Hz, 1H), 4.95 (dd, J=5.6, 5.2 Hz, 1H), 4.62 (dd, J=5.2, 4.8 Hz, 2H), 3.85 (q, J=5.2 Hz, 2H).

Example 24 10-fluoro-6-(3-hydroxypropylamino)-12H-thiochromeno[2,3-c]quinolin-12-one (7729)

Synthesized according to general procedure-D. Yield: 247 mg (73%). ES-MS [M+1]$^+$: 355.0; $t_R$: 3.79 min (method-C); $^1$H NMR (400 MHz, DMSO-d$_6$): δ 9.34 (d, J=8.0 Hz, 1H), 8.10 (dd, J=9.6, 2.8 Hz, 1H), 8.00 (dd, J=8.8, 5.2 Hz, 1H), 7.73 (dt, J=8.8, 2.8 Hz, 1H), 7.65 (d, J=7.2 Hz, 1H), 7.56 (dt, J=8.0, 1.2 Hz, 1H), 7.33 (dt, J=8.4, 1.2 Hz, 1H), 7.10 (d, J=4.8 Hz, 1H), 4.65 (brs, 1H), 3.62 (m, 2H), 3.55 (t, J=6.0 Hz, 2H), 1.84 (quint, J=6.4 Hz, 2H).

Example 25 10-fluoro-6-(3-methoxypropylamino)-12H-thiochromeno[2,3-c]quinolin-12-one (7730)

Synthesized according to general procedure-D. Yield: 150 mg (51%). ES-MS [M+1]$^+$: 369.0; $t_R$: 5.49 min (method-C); $^1$H NMR (400 MHz, DMSO-d$_6$): δ 9.35 (d, J=8.4 Hz, 1H), 8.13 (d, J=9.2 Hz, 1H), 8.03 (m, 1H), 7.75 (t, J=7.2 Hz, 1H), 7.66 (d, J=8.0 Hz, 1H), 7.57 (dd, J=7.6, 6.8 Hz, 1H), 7.35 (dd, J=8.0, 7.2 Hz, 1H), 7.12 (brs, 1H), 3.60 (q, J=5.2 Hz, 2H), 3.46 (t, J=5.6 Hz, 2H), 3.26 (s, 3H), 1.93 (quint, J=6.4 Hz, 2H).

Example 26 10-fluoro-6-(3-(methylamino)propylamino)-12H-thiochromeno[2,3-c]quinolin-12-one (7731)

Synthesized according to general procedure-D. Yield: 137 mg (47%). ES-MS [M+1]$^+$: 368.0; $t_R$: 3.29 min (method-C); $^1$H NMR (400 MHz, DMSO-d$_6$): δ 9.35 (d, J=8.4 Hz, 1H), 8.14 (dd, J=9.6, 2.4 Hz, 1H), 8.03 (dd, J=8.8, 4.8 Hz, 1H), 7.76 (ddd, J=8.8, 8.4, 2.8 Hz, 1H), 7.66 (d, J=8.0 Hz, 1H), 7.57 (dd, J=8.0, 6.8 Hz, 1H), 7.34 (dd, J=8.0, 7.6 Hz, 1H), 7.30 (brs, 1H), 3.62 (t, J=6.4 Hz, 2H), 2.64 (t, J=6.4 Hz, 2H), 2.33 (s, 3H), 1.81 (quint, J=6.4 Hz, 2H).

Example 27 6-(3-(dimethylamino)propylamino)-10-fluoro-12H-thiochromeno[2,3-c]quinolin-12-one (7732)

Synthesized according to general procedure-D. Yield: 240 mg (66%). ES-MS [M+1]$^+$: 382.0; $t_R$: 3.86 min (method-C); $^1$H NMR (400 MHz, DMSO-d$_6$): δ 9.36 (d, J=8.4 Hz, 1H), 8.15 (dd, J=9.6, 2.8 Hz, 1H), 8.05 (dd, J=8.8, 4.8 Hz, 1H), 7.77 (ddd, J=8.8, 8.4, 2.8 Hz, 1H), 7.67 (d, J=8.4 Hz, 1H), 7.62-7.56 (m, 2H), 7.36 (ddd, J=8.4, 8.0, 1.2 Hz, 1H), 3.62 (m, 2H), 2.77 (m, 2H), 2.49 (s, 6H), 1.94 (quint, J=6.8 Hz, 2H).

Example 28 10-fluoro-6-(3-morpholinopropylamino)-12H-thiochromeno[2,3-c]quinolin-12-one (7741)

Synthesized according to general procedure-D. Yield: 297 mg (72%). ES-MS [M+1]$^+$: 424.0; $t_R$: 5.13 min (method-A); $^1$H NMR (400 MHz, DMSO-d$_6$): δ 9.37 (d, J=8.4 Hz, 1H), 8.16 (dd, J=9.6, 2.8 Hz, 1H), 8.02 (dd, J=8.8, 4.8 Hz, 1H), 7.78 (td, J=8.0, 2.8 Hz, 1H), 7.65 (d, J=8.0 Hz, 1H), 7.58 (ddd, J=8.4, 7.6, 1.2 Hz, 1H), 7.38-7.33 (m, 2H), 3.62 (m, 6H), 2.46-2.41 (m, 6H), 1.85 (d, J=6.8 Hz, 2H).

Example 29 10-fluoro-6-(2-methoxyethylamino)-12H-thiochromeno[2,3-c]quinolin-12-one (7745)

Synthesized according to general procedure-D. Yield: 170 mg (50%). ES-MS [M+1]$^+$: 355.0; $t_R$: 2.8 min (method-A); $^1$H NMR (400 MHz, DMSO-d$_6$): δ 9.34 (d, J=8.8 Hz, 1H), 8.12 (dd, J=9.6, 2.4 Hz, 1H), 8.03 (dd, J=9.2, 5.2 Hz, 1H), 7.75 (td, J=8.4, 2.8 Hz, 1H), 7.66 (d, J=8.0 Hz, 1H), 7.57 (t, J=7.6 Hz, 1H), 7.35 (t, J=7.6 Hz, 1H), 7.02 (brs, 1H), 3.74 (q, J=5.6 Hz, 2H), 3.62 (t, J=5.6 Hz, 2H).

Example 30 10-fluoro-6-(piperidin-1-yl)-12H-thiochromeno[2,3-c]quinolin-12-one (7746)

Synthesized according to general procedure-D. Yield: 118 mg (34%). ES-MS [M+1]$^+$: 365.0; $t_R$: 4.57 min (method-D); $^1$H NMR (400 MHz, DMSO-d$_6$): δ 9.56 (d, J=8.4 Hz, 1H), 8.16 (dd, J=9.6, 2.8 Hz, 1H), 8.13 (dd, J=9.2, 5.2 Hz, 1H), 7.93 (d, J=8.4 Hz, 1H), 7.78-7.73 (m, 2H), 7.64 (t, J=7.2 Hz, 1H), 3.24 (t, J=4.4 Hz, 4H), 1.79-1.76 (m, 4H), 1.65 (m, 2H).

Example 31 10-fluoro-6-(pyrrolidin-1-yl)-12H-thiochromeno[2,3-c]quinolin-12-one (7747)

Synthesized according to general procedure-D. Yield: 166 mg (49%). ES-MS [M+1]$^+$: 350.9; $t_R$: 6.76 min (method-A); $^1$H NMR (400 MHz, DMSO-d$_6$): δ 9.35 (d, J=8.4 Hz, 1H), 8.11 (dd, J=9.6, 2.8 Hz, 1H), 8.06 (dd, J=8.8, 5.2 Hz, 1H), 7.77-7.23 (m, 2H), 7.65 (dd, J=8.0, 7.2 Hz, 1H), 7.46 (dd, J=8.0, 7.2 Hz, 1H), 3.70 (m, 4H), 1.94 (m, 4H).

Example 32 10-fluoro-6-morpholino-12H-thiochromeno[2,3-c]quinolin-12-one (7738)

Synthesized according to general procedure-D. Yield: 160 mg (55%). ES-MS [M+1]$^+$: 367.0; $t_R$: 5.43 min (method-C); $^1$H NMR (400 MHz, DMSO-d$_6$): δ 9.56 (d, J=8.4 Hz, 1H), 8.17-8.10 (m, 2H), 7.95 (d, J=8.0 Hz, 1H), 7.79-7.74 (m, 2H), 7.66 (t, J=7.2 Hz, 1H), 3.88 (m, 4H), 3.3 (m, 4H; found merged with signal from H—O-D).

Example 33 10-fluoro-6-(piperazin-1-yl)-12H-thiochromeno[2,3-c]quinolin-12-one (7739)

Synthesized according to modified general procedure-F with 1-Boc-piperazine replacing 4-methoxybenzylamine in first stage. Yield: 310 mg (56% over 2 steps). ES-MS [M+1]$^+$: 366.0; $t_R$: 3.6 min (method-A); $^1$H NMR (400 MHz, DMSO-d$_6$): δ 9.53 (d, J=8.4 Hz, 1H), 8.14-8.07 (m, 2H), 7.92 (d, J=8.0 Hz, 1H), 7.77-7.71 (m, 2H), 7.63 (ddd, J=8.4, 8.0, 1.0 Hz, 1H), 3.20 (m, 4H), 2.97 (m, 4H).

Example 34 10-fluoro-6-(4-methylpiperazin-1-yl)-12H-thiochromeno[2,3-c]quinolin-12-one (7740)

Synthesized according to general procedure-D. Yield: 175 mg (48%). ES-MS [M+1]$^+$: 380.0; $t_R$: 3.69 min (method-A); $^1$H NMR (400 MHz, DMSO-d$_6$): δ 9.51 (d, J=8.4 Hz, 1H), 8.1 (dd, J=9.6, 2.4 Hz, 1H), 8.07 (dd, J=8.8, 4.8 Hz, 1H), 7.91 (d, J=8.4 Hz, 1H), 7.76-7.70 (m, 2H), 7.61 (ddd, J=8.4, 7.2, 1.2 Hz, 1H), 3.29 (m, 4H, merged with signal of H—O-D), 2.63 (m, 4H), 2.31 (s, 3H).

Example 35 10-fluoro-6-(pyridin-3-ylmethylamino)-12H-thiochromeno[2,3-c]quinolin-12-one (7748)

Synthesized according to general procedure-D. Yield: 200 mg (54%). ES-MS [M+1]$^+$: 387.9; $t_R$: 4.33 min (method-A); $^1$H NMR (400 MHz, DMSO-d$_6$): δ 9.35 (d, J=8.4 Hz, 1H), 8.69 (s, 1H), 8.38 (d, J=4.0 Hz, 1H), 8.13 (dd, J=9.6, 2.8 Hz, 1H), 8.03 (dd, J=8.8, 5.2 Hz, 1H), 7.90-7.78 (m, 1H), 7.77-7.73 (m, 1H), 7.65 (dd, J=8.0, 7.2 Hz, 1H), 7.56 (t, J=7.2 Hz, 1H), 7.35 (t, J=7.6 Hz, 1H), 7.3 (dd, J=7.6, 4.8 Hz, 1H), 4.77 (d, J=5.6 Hz, 2H).

Example 36 6-(Benzylamino)-10-fluoro-12H-thiochromeno[2,3-c]quinolin-12-one (7749)

Synthesized according to general procedure-D. Yield: 127 mg (41.5%). ES-MS [M+1]$^+$: 386.9; $t_R$: 5.72 min (method-A); $^1$H NMR (400 MHz, DMSO-d$_6$): δ 9.35 (d, J=8.8 Hz, 1H), 8.14 (dd, J=9.2, 2.8 Hz, 1H), 8.04 (dd, J=8.8, 4.8 Hz, 1H), 7.8-7.74 (m, 2H), 7.63 (d, J=8.0 Hz, 1H), 7.55 (t, J=8.0 Hz, 1H), 7.44 (d, J=8.0 Hz, 2H), 7.35 (t, J=8.8 Hz, 1H), 7.28 (t, J=8.0 Hz, 2H), 7.18 (t, J=7.6 Hz, 1H), 4.78 (d, J=5.6 Hz, 2H).

Example 37 6-(2-(dimethylamino)ethylamino)-10-fluoro-12H-thiochromeno[2,3-c]quinolin-12-one (7744)

Synthesized according to general procedure-D. Yield: 210 mg (60%). ES-MS [M+1]$^+$: 367.9; $t_R$: 3.94 min (method-A); $^1$H NMR (400 MHz, DMSO-d$_6$): δ 9.35 (d, J=8.4 Hz, 1H), 8.14 (dd, J=10.0, 2.8 Hz, 1H), 8.07 (dd, J=8.8, 5.2 Hz, 1H), 7.76 (td, J=8.4, 2.8 Hz, 1H), 7.67 (d, J=7.6 Hz, 1H), 7.58 (t, J=7.2 Hz, 1H), 7.36 (t, J=7.2 Hz, 1H), 6.85 (brs, 1H), 3.65 (q, J=6.0 Hz, 2H), 2.57 (t, J=6.4 Hz, 2H), 2.23 (s, 6H).

Example 38 10-fluoro-6-(1H-pyrrol-1-yl)-12H-thiochromeno[2,3-c]quinolin-12-one (7750)

Synthesized according to general procedure-H starting from scaffold compound 4b. Yield: 96 mg (27%). ES-MS [M+1]$^+$: 346.9; $t_R$: 7.21 min (Method-G), $^1$H NMR (400 MHz, DMSO-d$_6$): δ 9.59 (d, J=8.4 Hz, 1H), 8.16 (dd, J=9.6, 2.8 Hz, 1H), 8.09 (m, 2H), 7.85 (m, 2H), 7.76 (td, J=8.4, 2.8 Hz, 1H), 7.40 (m, 2H), 6.41 (m, 2H).

Example 39 10-fluoro-6-(2-(methylamino)ethylamino)-12H-thiochromeno[2,3-c]quinolin-12-one (7752)

Synthesized according to general procedure-D starting from scaffold compound 4b. Yield: 165 mg (49%). ES-MS [M+1]$^+$: 353.9; tR: 4.12 min (Method-E), 1H NMR (400 MHz, DMSO-d$_6$): δ 9.38 (d, J=8.0 Hz, 1H), 8.94 (brs, 1H), 8.16 (dd, J=10.0, 2.8 Hz, 1H), 8.05 (dd, J=9.2, 8.8 Hz, 1H), 7.79-7.74 (m, 2H), 7.62 (dd, J=7.2, 6.8 Hz, 1H), 7.48 (t, J=5.2 Hz, 1H), 7.41 (dd, J=7.6, 7.2 Hz, 1H), 3.88 (m, 2H), 3.25 (m, 2H), 2.59 (s, 3H).

Example 40 10-fluoro-6-(3-(pyrrolidin-1-yl)propylamino)-12H-thiochromeno[2,3-c]quinolin-12-one (7753)

Synthesized according to general procedure-D starting from scaffold compound 4b. Yield: 125 mg (32%). ES-MS [M+1]$^+$: 408.0; $t_R$: 3.39 min (Method-E), 1H NMR (400 MHz, DMSO-d$_6$): δ 9.37 (d, J=8.4 Hz, 1H), 8.15 (dd, J=9.6, 2.8 Hz, 1H), 8.01 (dd, J=8.4, 4.4 Hz, 1H), 7.78 (td, J=8.4, 2.8 Hz, 1H), 7.69 (d, J=8.0 Hz, 1H), 7.60 (t, J=6.8 Hz, 1H), 7.47 (brs, 1H), 7.38 (t, J=7.6 Hz, 1H), 3.65 (q, J=4.8 Hz, 2H), 3.1 (brs, 4H), 2.05 (t, J=6.0 Hz, 2H), 1.88 (brs, 4H).

Example 41 6-(2-aminoethylamino)-10-fluoro-12H-thiochromeno[2,3-c]quinolin-12-one (7754)

Synthesized according to general procedure-E starting from scaffold compound 4b. Yield: 115 mg (36%). ES-MS [M+1]$^+$: 340.0; tR: 4.69 min (Method-E), 1H NMR (400 MHz, DMSO-d$_6$): δ 9.38 (d, J=8.4 Hz, 1H), 8.15 (d, J=9.6

Hz, 1H), 8.06 (m, 1H), 7.78 (m, 1H), 7.72 (d, J=8.0 Hz, 1H), 7.61 (dd, J=7.6, 7.2 Hz, 1H), 7.40 (t, J=7.6 Hz, 1H), 3.75 (m, 2H), 3.08 (m, 2H).

Example 42 10-fluoro-6-(2-(pyrrolidin-1-yl)ethylamino)-12H-thiochromeno[2,3-c]quinolin-12-one (7755)

Synthesized according to general procedure-D starting from scaffold compound 4b. Yield: 82 mg (22%). ES-MS [M+1]$^+$: 394.1; $t_R$: 3.34 min (Method-E), 1H NMR (400 MHz, DMSO-d$_6$): δ 9.39 (d, J=8.4 Hz, 1H), 8.17 (dd, J=9.6, 4.8 Hz, 1H), 8.06 (dd, J=8.8, 4.8 Hz, 1H), 7.79 (ddd, J=8.8, 8.4, 2.8 Hz, 1H), 7.73 (d, J=7.6 Hz, 1H), 7.63 (t, J=6.8 Hz, 1H), 7.55 (brs, 1H), 7.42 (dd, J=8.4, 7.2 Hz, 1H), 3.93 (m, 2H), 3.67 (brs, 2H), 3.47 (m, 2H), 3.09 (m, 2H), 1.99 (brs, 2H), 1.87 (brs, 2H).

Example 43 10-fluoro-6-((2-morpholinoethyl)amino)-12H-thiochromeno[2,3-c]quinolin-12-one (7756)

Synthesized according to general procedure-D starting from scaffold compound 4b. Yield: 194 mg (50%). ES-MS [M+1]$^+$: 409.9; $t_R$: 4.08 min (Method-E), $^1$H NMR (400 MHz, DMSO-d$_6$): δ 9.36 (d, J=8.0 Hz, 1H), 8.14 (dd, J=10.0, 2.8 Hz, 1H), 8.06 (dd, J=9.2, 5.2 Hz, 1H), 7.77 (ddd, J=8.8, 8.4, 2.8 Hz, 1H), 7.67 (d, J=7.6 Hz, 1H), 7.58 (dd, J=7.2, 6.8 Hz, 1H), 7.36 (t, J=7.2 Hz, 1H), 6.98 (m, 1H), 3.68 (m, 2H), 3.58 (m, 4H), 2.47 (m, 4H; merged with residual DMSO signal), 2.63 (t, J=6.4 Hz, 2H).

Example 44 tert-butyl 4-(10-fluoro-12-oxo-12H-thiochromeno[2,3-c]quinolin-6-yl)piperazine-1-carboxylate (7764)

Synthesized according to general procedure-D starting from scaffold compound 4b. Yield: 230 mg (53%). ES-MS [M+1]$^+$: 465.9; $t_R$: 7.57 min (Method-E), $^1$H NMR (400 MHz, DMSO-d$_6$): δ 9.55 (d, J=8.4 Hz, 1H), 8.14 (d, J=10.0 Hz, 1H), 8.09 (m, 1H), 7.93 (d, J=8.4 Hz, 1H), 7.76 (m, 2H), 7.65 (dd, J=8.4, 7.2 Hz, 1H), 3.61 (brs, 4H), 3.25 (m, 4H), 1.43 (s, 9H).

Example 45 6-(4-ethylpiperazin-1-yl)-10-fluoro-12H-thiochromeno[2,3-c]quinolin-12-one (7757)

Synthesized according to general procedure-I in presence of ethyl iodide. Yield: 160 mg (49%). ES-MS [M+1]$^+$: 394.0; $t_R$: 4.37 min (method-F), $^1$H NMR (400 MHz, DMSO-d$_6$): δ 9.53 (d, J=8.4 Hz, 1H), 8.14-8.07 (m, 2H), 7.92 (d, J=8.0 Hz, 1H), 7.77-7.72 (m, 2H), 7.64 (dd, J=8.0, 7.6 Hz, 1H), 2.70-2.64 (m, 2H), 1.08 (m, 3H).

Example 46 6-(4-benzylpiperazin-1-yl)-10-fluoro-12H-thiochromeno[2,3-c]quinolin-12-one (7758)

Synthesized according to general procedure-I in presence of benzyl chloride. Yield: 152 mg (61%). ES-MS [M+1]$^+$: 456.0; $t_R$: 4.59 min (method-E), $^1$H NMR (400 MHz, DMSO-d$_6$): δ 9.54 (d, J=8.8 Hz, 1H), 8.15-8.07 (m, 2H), 7.93 (d, J=8.0 Hz, 1H), 7.74 (dd, J=8.0, 7.6 Hz, 2H), 7.64 (dd, J=8.0, 7.6 Hz, 1H), 7.38-7.32 (m, 4H), 7.26 (m, 1H), 3.62 (s, 2H), 3.32 (m, 4H), 2.69 (m, 4H).

Example 47 10-fluoro-6-(1H-pyrazol-1-yl)-12H-thiochromeno[2,3-c]quinolin-12-one (7759)

Synthesized according to modified general procedure-H wherein, K$_2$CO$_3$, L-proline and CuI were used as base, ligand and catalyst respectively. Yield: 168 mg (51%). ES-MS [M+1]: 347.9; $t_R$: 6.96 min (Method-E), $^1$H NMR (400 MHz, DMSO-d$_6$): δ 9.44 (d, J=8.8 Hz, 1H), 8.64 (d, J=2.4 Hz, 1H), 8.13-8.05 (m, 3H), 8.02 (d, J=1.6 Hz, 1H), 7.89 (dd, J=10.0, 8.4 Hz, 1H), 7.83 (dd, J=8.0, 6.8 Hz, 1H), 7.75 (td, J=8.8, 2.8 Hz, 1H), 6.74 (t, J=2.4 Hz, 1H).

Example 48 10-fluoro-6-(pyridin-2-ylamino)-12H-thiochromeno[2,3-c]quinolin-12-one (7760)

Synthesized according to general procedure-H starting from scaffold compound 4b. Yield: 200 mg (25%). ES-MS [M+1]$^+$: 373.9; $t_R$: 5.98 min (Method-E), $^1$H NMR (400 MHz, DMSO-d$_6$): δ 9.43 (d, J=7.2 Hz, 1H), 8.35 (brs, 1H), 8.18-8.12 (m, 2H), 7.87-7.76 (m, 4H), 7.62 (m, 1H), 7.39 (m, 1H), 7.23 (d, J=7.2 Hz, 1H), 7.00 (m, 1H).

Example 49 10-fluoro-6-(pyridin-3-ylamino)-12H-thiochromeno[2,3-c]quinolin-12-one (7761)

Synthesized according to general procedure-H starting from scaffold compound 4b. Yield: 82 mg (23%). ES-MS [M+1]$^+$: 373.9; $t_R$: 4.19 min (Method-E), $^1$H NMR (400 MHz, DMSO-d$_6$): δ 9.47 (d, J=8.4 Hz, 1H), 9.23 (brs, 1H), 8.91 (d, J=2.0 Hz, 1H), 8.25 (d, J=4.4 Hz, 1H), 8.19 (dd, J=9.6, 2.8 Hz, 1H), 8.14-8.11 (m, 2H), 7.81 (td, J=8.4, 2.8 Hz, 1H), 7.73 (d, J=7.6 Hz, 1H), 7.67 (t, J=7.2 Hz, 1H), 7.53 (dd, J=8.0, 7.2 Hz, 1H), 7.38 (dd, J=8.4, 4.4 Hz, 1H)

Example 50 10-fluoro-6-(phenylamino)-12H-thiochromeno[2,3-c]quinolin-12-one (7762)

Synthesized according to general procedure-D starting from scaffold compound 4b. Yield: 85 mg (23%). ES-MS [M+1]$^+$: 372.9; $t_R$: 3.59 min (Method-E), $^1$H NMR (400 MHz, DMSO-d$_6$): δ 9.45 (d, J=8.4 Hz, 1H), 8.99 (s, 1H), 8.17 (dd, J=9.6, 2.8 Hz, 1H), 8.12-8.09 (m, 1H), 7.78 (td, J=8.8, 2.8 Hz, 1H), 7.72-7.63 (m, 4H), 7.50 (td, J=8.4, 1.2 Hz, 1H), 7.34 (m, 2H), 7.04 (t, J=7.2 Hz, 1H).

Example 51 10-fluoro-6-(pyridin-4-ylamino)-12H-thiochromeno[2,3-c]quinolin-12-one (7763)

Synthesized according to general procedure-H starting from scaffold compound 4b. Yield: 189 mg (53%). ES-MS [M+1]$^+$: 373.9; $t_R$: 5.57 min (Method-G), $^1$H NMR (400 MHz, DMSO-d$_6$): δ 9.54 (brs, 1H), 9.52 (d, J=8.4 Hz, 1H), 8.34 (m, 2H), 8.18 (dd, J=9.6, 2.8 Hz, 1H), 8.14 (m, 1H), 7.85-7.80 (m, 2H), 7.72 (m, 1H), 7.63 (m, 3H).

Example 51 10-fluoro-6-((2-(pyridin-2-ylamino)ethyl)amino)-12H-thiochromeno[2,3-c]quinolin-12-one (7765)

Synthesized according to general procedure-D starting from scaffold compound 4b. Yield: 115 mg (27%). ES-MS [M+1]$^+$: 417.0; $t_R$: 6.67 min (Method-G), $^1$H NMR (400 MHz, DMSO-d$_6$): δ 9.36 (d, J=8.0 Hz, 1H), 8.14 (dd, J=10.0, 2.8 Hz, 1H), 8.11-8.05 (m, 2H), 7.77 (td, J=8.4, 2.8 Hz, 1H), 7.70-7.67 (m, 2H), 7.58 (td, J=7.6, 1.2 Hz, 1H), 7.4-7.34 (m, 2H), 6.85 (m, 1H), 6.56-6.49 (m, 2H), 3.72 (q, J=5.2 Hz, 2H), 3.59 (q, J=5.2 Hz, 2H).

Example 52 10-fluoro-6-(1H-imidazol-1-yl)-12H-thiochromeno[2,3-c]quinolin-12-one (7766)

Synthesized according to general procedure-H starting from scaffold compound 4b. Yield: 105 mg (31%). ES-MS

[M+1]+: 348.0; t$_R$: 5.29 min (Method-G), $^1$H NMR (400 MHz, DMSO-d$_6$): δ 9.71 (s, 1H), 8.31-8.19 (m, 4H), 7.96 (m, 2H), 7.84 (m, 2H), 7.28 (s, 1H).

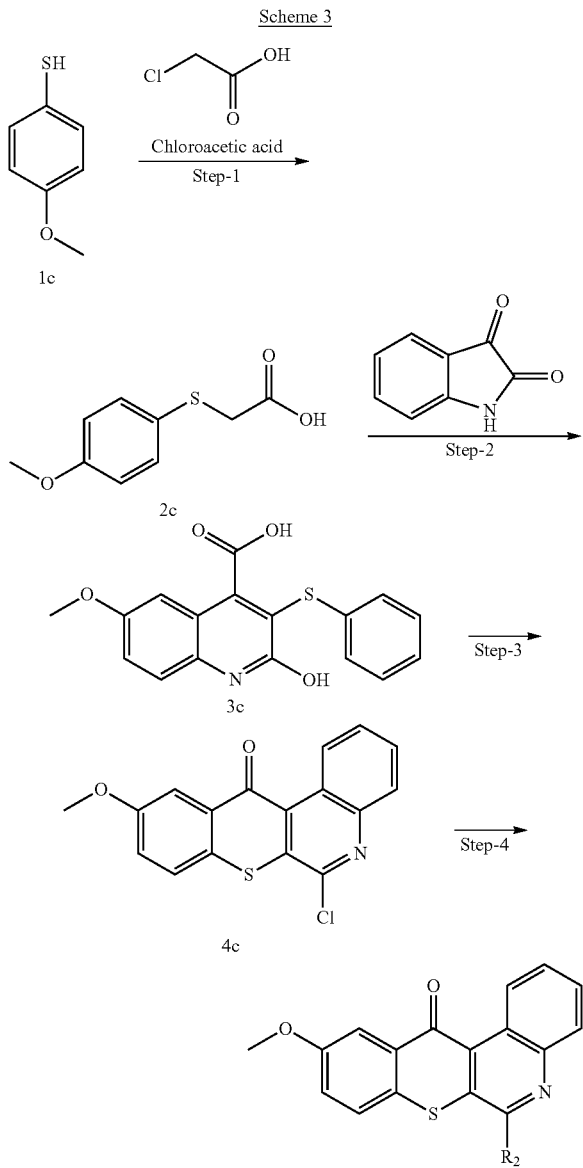

Example 53 6-chloro-10-methoxy-12H-thiochromeno[2,3-c]quinolin-12-one (4c)

Synthesized starting from 4-methoxythiophenol in 3 steps following general procedures A-C. Yield: 51% over 3 steps. ES-MS [M+1]+: 327.9; t$_R$: 5.95 min (method-A).

Example 54 6-Amino-10-methoxy-12H-thiochromeno[2,3-c]quinolin-12-one (7709)

Synthesized according to general procedure-F. Yield: 195 mg (84%). ES-MS [M+1]+: 309.0; t$_R$: 3.29 min (method-A); $^1$H NMR (400 MHz, DMSO-d$_6$): δ 9.46 (d, J=8.5 Hz, 1H), 7.95 (d, J=2.7 Hz, 1H), 7.89 (d, J=8.8 Hz, 1H), 7.66 (d, J=8.0 Hz, 1H), 7.6 (t, J=7.7 Hz, 1H), 7.5 (dd, J=8.8, 2.8 Hz, 1H), 7.39 (t, J=8.2 Hz, 1H), 7.02 (brs, 2H), 3.94 (s, 3H).

Example 55 10-methoxy-6-(propylamino)-12H-thiochromeno[2,3-c]quinolin-12-one (7710)

Synthesized according to general procedure-D. Yield: 120 mg (45%). ES-MS [M+1]+: 351.0; t$_R$: 5.71 min (method-A); $^1$H NMR (400 MHz, DMSO-d$_6$): δ 9.40 (d, J=8.4, 1H), 7.91 (d, J=2.8 Hz, 1H), 7.86 (d, J=8.8, 1H), 7.66 (dd, J=8.4, 1.2 Hz, 1H), 7.56 (ddd, J=8.4, 6.8, 1.2 Hz, 1H), 7.46 (td, J=8.4, 2.8 Hz, 1H), 7.34 (ddd, J=8.4, 6.8, 1.2 Hz, 1H), 7.08 (dd, J=4.8, 5.2 Hz, 1H), 3.91 (s, 3H), 3.52 (m, 2H), 1.70 (sextet, J=7.2 Hz, 2H), 0.94 (t, J=7.2 Hz, 3H).

Example 56 6-(3-aminopropylamino)-10-methoxy-12H-thiochromeno[2,3-c]quinolin-12-one (7711)

Synthesized according to general procedure-E. Yield: 130 mg (46%). ES-MS [M+1]+: 366.0; t$_R$: 2.12 min (method-A); $^1$H NMR (400 MHz, DMSO-d$_6$): δ 9.43 (d, J=8.0 Hz, 1H), 7.94 (d, J=2.8 Hz, 1H), 7.88 (d, J=8.8 Hz, 1H), 7.70 (d, J=8.0 Hz, 1H), 7.6 (td, J=7.0, 1.2 Hz, 1H), 7.50 (dd, J=8.8, 2.8 Hz, 1H), 7.37 (t, J=7.2 Hz, 1H), 3.94 (s, 3H), 3.67 (t, J=6.4 Hz, 2H), 2.79 (t, J=6.8 Hz, 2H), 1.86 (t, J=6.4 Hz, 2H).

Example 57 6-(3-(2-hydroxyethylamino)propylamino)-10-methoxy-12H-thiochromeno[2,3-c]quinolin-12-one (7712)

Synthesized according to general procedure-D. Yield: 320 mg (72%). ES-MS [M+1]+: 410.0; t$_R$: 2.04 min (method-A); $^1$H NMR (400 MHz, DMSO-d$_6$): δ 9.43 (d, J=8.0 Hz, 1H), 7.93 (d, J=2.0 Hz, 1H), 7.86 (d, J=8.8 Hz, 1H), 7.70 (d, J=8.0 Hz, 1H), 7.58 (t, J=7.2 Hz, 1H), 7.5 (dd, J=8.8, 2.8 Hz, 1H), 7.36 (t, J=8.0 Hz, 1H), 3.93 (m, 4H), 3.66 (t, J=6.4 Hz, 2H), 3.59 (t, J=5.4 Hz, 2H), 2.84 (t, J=6.4 Hz, 2H), 2.77 (t, J=5.4 Hz, 2H), 1.92 (t, J=6.4 Hz, 2H).

Example 58 6-(2-Hydroxyethylamino)-10-methoxy-12H-thiochromeno[2,3-c]quinolin-12-one (7733)

Synthesized according to general procedure-D. Yield: 200 mg (62%). ES-MS [M+1]+: 353.0; t$_R$: 3.25 min (method-C); $^1$H NMR (400 MHz, DMSO-d$_6$): δ 9.40 (d, J=8.4 Hz, 1H), 7.90 (d, J=3.2 Hz, 1H), 7.87 (d, J=8.8 Hz, 1H), 7.66 (d, J=8.0 Hz, 1H), 7.57 (dd, J=7.6, 7.2 Hz, 1H), 7.46 (dd, J=8.4, 2.8 Hz, 1H), 7.35 (dd, J=8.0, 7.6 Hz, 1H), 6.92 (t, J=4.4 Hz, 1H), 4.84 (brs, 1H), 3.91 (s, 3H), 3.65 (m, 4H).

Example 59 10-methoxy-6-(3-hydroxypropylamino)-12H-thiochromeno[2,3-c]quinolin-12-one (7742)

Synthesized according to general procedure-D. Yield: 210 mg (75%). ES-MS [M+1]+: 366.9; t$_R$: 3.50 min (method-A); $^1$H NMR (400 MHz, DMSO-d$_6$): δ 9.39 (d, J=8.0 Hz, 1H), 7.89 (d, J=3.2 Hz, 1H), 7.84 (d, J=8.8 Hz, 1H), 7.65 (d, J=8.0 Hz, 1H), 7.56 (ddd, J=8.4, 6.8, 1.2 Hz, 1H), 7.44 (dd, J=8.8, 2.8 Hz, 1H), 7.34 (dt, J=8.4, 1.2 Hz, 1H), 7.08 (d, J=4.8 Hz, 1H), 4.70 (brs, 1H), 3.90 (s, 3H), 3.62 (m, 2H), 3.55 (t, J=6.4 Hz, 2H), 1.84 (quint, J=6.4 Hz, 2H).

Example 60 10-methoxy-6-(3-methoxypropylamino)-12H-thiochromeno[2,3-c]quinolin-12-one (7743)

Synthesized according to general procedure-D. Yield: 170 mg (59%). ES-MS [M+1]+: 381.0; t$_R$: 5.08 min (method-A);

¹H NMR (400 MHz, DMSO-d₆): δ 9.40 (d, J=8.4 Hz, 1H), 7.91 (d, J=2.8 Hz, 1H), 7.87 (d, J=8.8 Hz, 1H), 7.66 (d, J=8.4 Hz, 1H), 7.56 (t, J=6.8 Hz, 1H), 7.46 (dd, J=8.8, 2.8 Hz, 1H), 7.35 (dd, J=7.2, 6.8 Hz, 1H), 7.09 (t, J=5.2 Hz, 1H), 3.91 (s, 3H), 3.61 (m, 2H), 3.46 (t, J=6.0 Hz, 2H), 3.26 (s, 3H), 1.93 (quint, J=6.8 Hz, 2H).

Example 61 10-methoxy-6-(3-(methylamino)propylamino)-12H-thiochromeno[2,3-c]quinolin-12-one (7734)

Synthesized according to general procedure-D. Yield: 160 mg (69%). ES-MS [M+1]⁺: 380.0; $t_R$: 3.02 min (method-C); ¹H NMR (400 MHz, DMSO-d₆): δ 9.41 (d, J=8.4 Hz, 1H), 8.68 (brs, 1H), 7.92 (s, 1H), 7.87 (d, J=8.8 Hz 1H), 7.70 (d, J=7.6 Hz, 1H), 7.59 (dd, J=8.0, 6.8 Hz, 1H), 7.49 (d, J=8.8 Hz, 1H), 7.39-7.35 (m, 2H), 3.92 (s, 3H), 3.65 (q, J=5.6 Hz, 2H), 2.96 (m, 2H), 2.52 (brs, 3H), 2.03 (m, 2H).

Example 62 6-(3-(dimethylamino)propylamino)-10-methoxy-12H-thiochromeno[2,3-c]quinolin-12-one (7735)

Synthesized according to general procedure-D. Yield: 100 mg (33%). ES-MS [M+1]⁺: 394.0; $t_R$: 4.24 min (method-A); ¹H NMR (400 MHz, DMSO-d₆): δ 9.40 (d, J=8.4 Hz, 1H), 7.9 (s, 1H), 7.88 (d, J=8.8 Hz, 1H), 7.75 (brs, 1H), 7.65 (d, J=8.4 Hz, 1H), 7.55 (t, J=7.6 Hz, 1H), 7.45 (dd, J=8.8, 2.8 Hz, 1H), 7.33 (dd, J=8.0, 7.2 Hz, 1H), 3.91 (s, 3H), 3.60 (m, 2H), 2.40 (t, J=6.0 Hz, 2H), 2.23 (s, 6H), 1.82 (quint, J=6.0 Hz, 2H).

Scheme 4

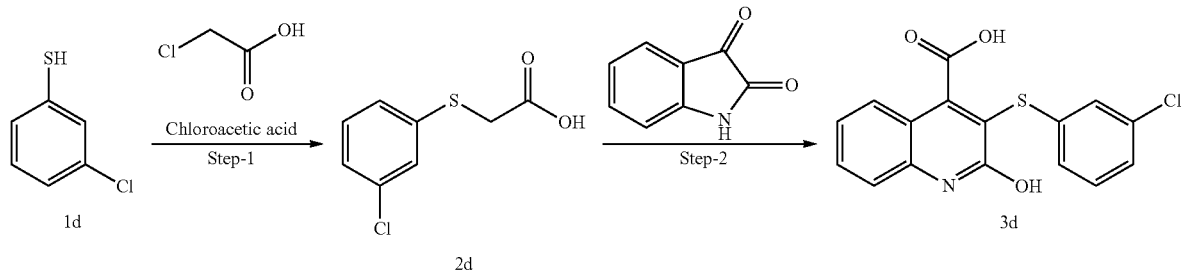

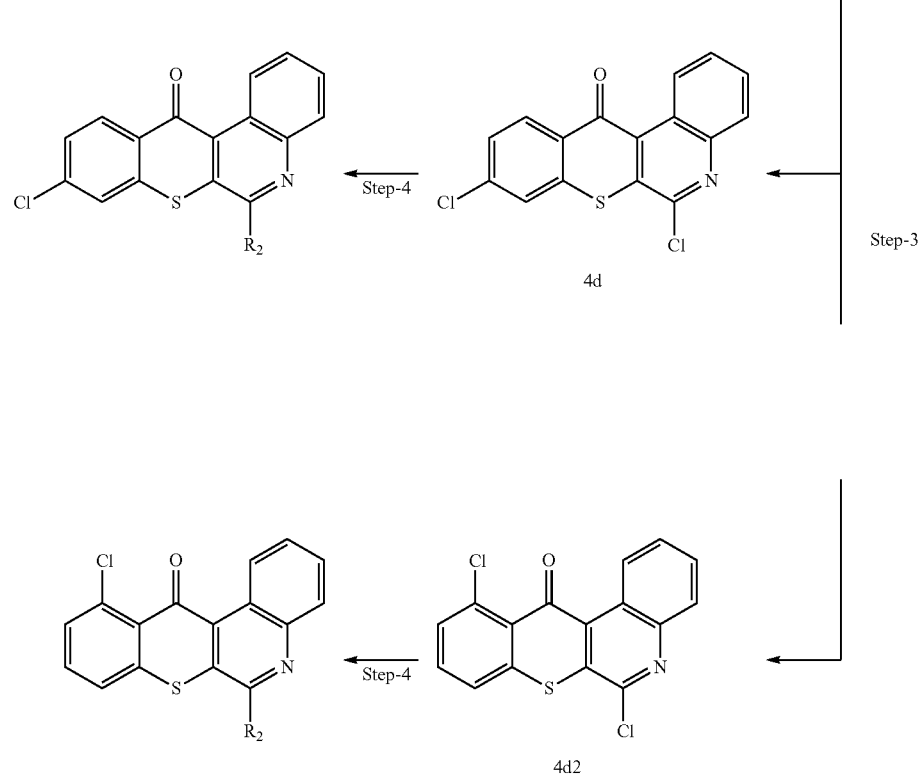

Example 63 Mixture of 6,9-dichloro-12H-thio-
chromeno[2,3-c]quinolin-12-one and 6,11-dichloro-
12H-thiochromeno[2,3-c]quinolin-12-one (4d/4d2)

Synthesized starting from 3-chlorothiophenol in 3 steps following general procedures A-C. The isomeric mixture 4d/4d2 formed could not be purified further and was as such used in analogue generation. Yield: 49% over 3 steps. ES-MS [M+1]$^+$: 331.9 and 331.9; $t_R$: 5.52 and 7.08 min (method-A).

Example 64 6-Amino-9-chloro-12H-thiochromeno
[2,3-c]quinolin-12-one (7723)

Synthesized according to general procedure-F starting from 4d/4d2 mixture. However, crude mixture of 6q1 and 6q2 obtained after stage-1 was purified in to individual isomers and preparation of 6q1 was further performed starting with isomer-1 (non-polar as compared to isomer-2). Yield: 170 mg (Stage-2: 78%). ES-MS [M+1]$^+$: 312.9; $t_R$: 3.99 min (method-A); $^1$H NMR (400 MHz, TFA-d$_1$): δ 9.74 (d, J=8.8 Hz, 1H), 8.95 (d, J=8.8 Hz, 1H), 8.26 (m, 2H), 8.15 (m, 3H).

Example 65 6-Amino-11-chloro-12H-thiochromeno
[2,3-c]quinolin-12-one (7724)

Synthesized according to general procedure-F starting from 4d/4d2 mixture. However, crude mixture of 6q1 and 6q2 obtained after stage-1 was purified in to individual isomers and preparation of 6q2 was further performed starting with isomer-2 (polar as compared to isomer-1). Yield: 60 mg (Stage-2: 40%). ES-MS [M+1]$^+$: 312.9; $t_R$: 3.24 min (method-A); $^1$H NMR (400 MHz, TFA-d$_1$): δ 9.20 (d, J=8.4 Hz, 1H), 8.31 (m, 1H), 8.20-8.12 (m, 5H).

Example 66 9-chloro-6-(propylamino)-12H-thio-
chromeno[2,3-c]quinolin-12-one (7725)

Synthesized according to general procedure-D starting from 4d/4d2 mixture. The non-polar product of the two isomers present in the crude mixture was isolated by FCC and confirmed as 6r1. Yield: 195 mg. ES-MS [M+1]$^+$: 355.0; $t_R$: 6.60 min (method-A); $^1$H NMR (400 MHz, DMSO-d$_6$): δ 9.31 (d, J=8.0 Hz, 1H), 8.40 (d, J=8.8 Hz, 1H), 8.09 (d, J=1.6 Hz, 1H), 7.69 (dd, J=8.8, 2.0 Hz, 1H), 7.66 (d, J=8.4 Hz, 1H), 7.57 (ddd, J=8.4, 8.0, 1.6 Hz, 1H), 7.34 (td, J=8.4, 1.6 Hz, 1H), 7.09 (t, J=5.6 Hz, 1H), 3.51 (q, J=6.0 Hz, 2H), 1.70 (sextet, J=7.2 Hz, 2H), 0.94 (t, J=7.2 Hz, 3H).

Example 67 11-chloro-6-(propylamino)-12H-thio-
chromeno[2,3-c]quinolin-12-one (7726)

Synthesized according to general procedure-D starting from 4d/4d2 mixture. The polar product of the two isomers present in the crude mixture was isolated by FCC and confirmed as 6r2. Yield: 176 mg. ES-MS [M+1]$^+$: 312.9; $t_R$: 3.24 min (method-A); $^1$H NMR (400 MHz, DMSO-d$_6$): δ 8.53 (d, J=8.4 Hz, 1H), 7.83 (m, 1H), 7.69-7.67 (m, 2H), 7.63 (d, J=8.0 Hz, 1H), 7.54 (dd, J=8.4, 7.2, 1.2 Hz, 1H), 7.29 (ddd, J=8.4, 6.8, 1.2 Hz, 1H), 3.50 (q, J=6.8 Hz, 2H), 1.68 (sextet, J=7.2 Hz, 2H), 0.93 (t, J=7.2 Hz, 3H).

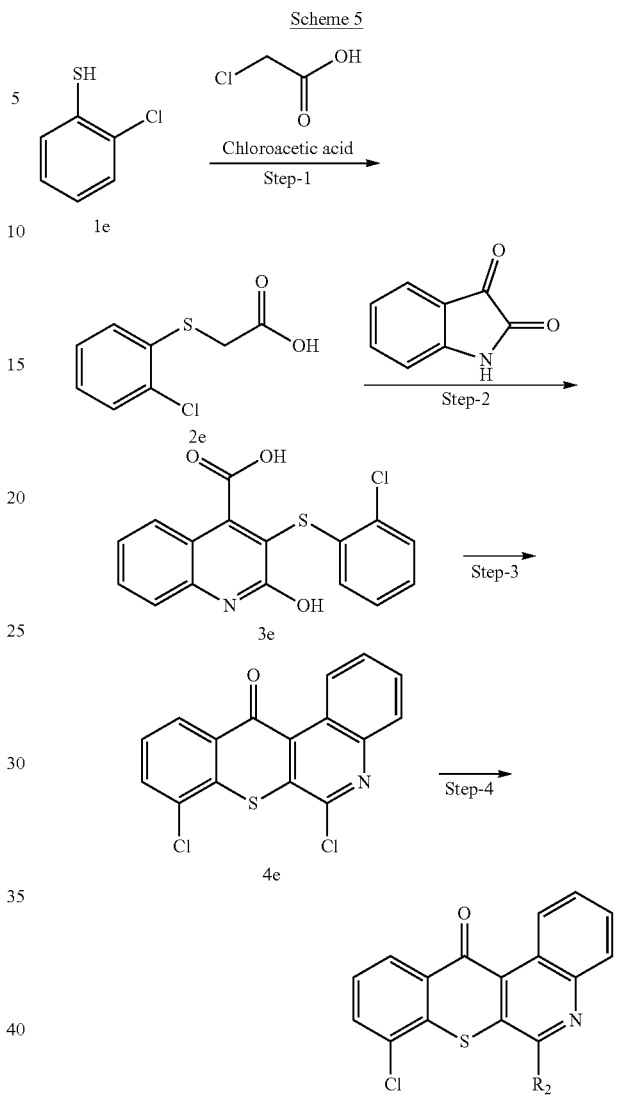

Scheme 5

Example 68 6,8-dichloro-12H-thiochromeno[2,3-c]
quinolin-12-one (4e)

Synthesized starting from 2-chlorothiophenol in 3 steps following general procedures A-C. Yield: 50% over 3 steps. ES-MS [M+1]$^+$: 331.9; $t_R$: 6.90 min (method-A).

Example 69 6-Amino-8-chloro-12H-thiochromeno
[2,3-c]quinolin-12-one (7713)

Synthesized according to general procedure-F. Yield: 550 mg (85%). ES-MS [M+1]$^+$: 312.9; $t_R$: 3.95 min (method-A); $^1$H NMR (400 MHz, DMSO-d$_6$): δ 9.31 (d, J=8.8, 1H), 8.41 (d, J=7.6 Hz, 1H), 8.00 (d, J=8.0 Hz, 1H), 7.69-7.57 (m, 3H), 7.37 (dd, J=8.0, 6.8 Hz, 1H), 7.15 (brs, 2H).

Example 70 8-chloro-6-(propylamino)-12H-thio-
chromeno[2,3-c]quinolin-12-one (7714)

Synthesized according to general procedure-D. Yield: 630 mg (84%). ES-MS [M+1]$^+$: 355.0; $t_R$: 6.57 min (method-A); $^1$H NMR (400 MHz, DMSO-d$_6$): δ 9.30 (d, J=8.8 Hz, 1H), 8.43 (d, J=8.0 Hz, 1H), 8.03 (dd, J=8.0, 1.6 Hz, 1H), 7.71-7.66 (m, 2H), 7.58 (dd, J=8.0, 1.2 Hz, 1H), 7.37-7.32 (m, 2H), 3.54 (m, 2H), 1.71 (sextet, J=7.2 Hz, 2H), 0.95 (t, J=7.2 Hz, 3H).

Example 71 6-(3-aminopropylamino)-8-chloro-12H-thiochromeno[2,3-c]quinolin-12-one (7715)

Synthesized according to general procedure-E. Yield: 400 mg (47%). ES-MS [M+1]$^+$: 370.0; $t_R$: 2.34 min (method-A); $^1$H NMR (400 MHz, DMSO-d$_6$): δ 9.28 (d, J=8.0 Hz, 1H), 8.40 (d, J=8.0 Hz, 1H), 8.01 (d, J=7.6 Hz, 1H), 7.69-7.65 (m, 2H), 7.58 (t, J=7.2 Hz, 1H), 7.34 (t, J=7.2 Hz, 1H), 3.65 (t, J=6.4 Hz, 2H), 2.73 (t, J=6.4 Hz, 2H), 1.80 (quint, J=6.4 Hz, 3H).

Example 72 8-chloro-6-(3-(2-hydroxyethylamino)propylamino)-12H-thiochromeno[2,3-c]quinolin-12-one (7716)

Synthesized according to general procedure-D. Yield: 700 mg (74%). ES-MS [M+1]$^+$: 414.0; $t_R$: 2.11 min (method-A); $^1$H NMR (400 MHz, DMSO-d$_6$): δ 9.26 (d, J=8.4 Hz, 1H), 8.37 (d, J=8.0 Hz, 1H), 7.97 (d, J=8.0 Hz, 1H), 7.82 (brs, 1H), 7.66-7.63 (m, 2H), 7.55 (dd, J=7.6, 7.2 Hz, 1H), 7.31 (dd, J=8.0, 7.2 Hz, 1H), 5.00 (brs, 1H), 3.62 (t, J=6.0 Hz, 2H), 3.53 (m, 2H), 2.71 (t, J=6.0 Hz, 2H), 2.63 (t, J=5.6 Hz, 2H), 1.82 (quint, J=6.0 Hz, 2H).

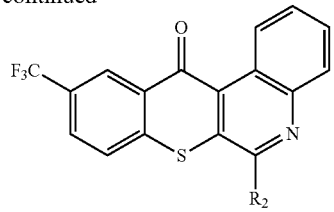

Example 73 6-chloro-10-trifluoromethyl-12H-thiochromeno[2,3-c]quinolin-12-one (4f)

Synthesized starting from 4-(trifluoromethyl)thiophenol in 3 steps following general procedures A-C. Yield: 25% over 3 steps. ES-MS [M+1]$^+$: 365.8; tR: 3.83 min (Method-E)

Example 74 6-(3-aminopropylamino)-10-trifluoromethyl-12H-thiochromeno[2,3-c]quinolin-12-one (7201)

Synthesized according to general procedure-E starting from scaffold compound 4f. Yield: 120 mg (36%). ES-MS [M+1]: 403.9; $t_R$: 3.40 min (Method-E), $^1$H NMR (400 MHz, DMSO-d$_6$): δ 9.33 (d, J=8.0 Hz, 1H), 8.67 (s, 1H), 8.18-8.11 (m, 2H), 7.70 (d, J=8.4 Hz, 1H), 7.61 (t, J=7.6 Hz, 1H), 7.38 (t, J=7.6 Hz, 1H), 6.5 (brs, 3H), 3.66 (t, J=6.4 Hz, 2H), 2.83 (t, J=6.8 Hz, 2H), 1.92 (quint, J=6.8 Hz, 2H).

Example 75 6-(3-(2-hydroxyethylamino)propylamino)-10-trifluoromethyl-12H-thiochromeno[2,3-c]quinolin-12-one (7214)

Synthesized according to general procedure-D starting from scaffold compound 4f. Yield: 610 mg (89%); ES-MS [M+1]: 447.9; $t_R$: 4.39 min (Method-G), $^1$H NMR (400 MHz, DMSO-d$_6$): δ 9.32 (d, J=8.8 Hz, 1H), 8.64 (s, 1H), 8.12 (m, 2H), 7.66 (d, J=8.4 Hz, 1H), 7.58 (dd, J=8.4, 6.4 Hz, 1H), 7.35 (dd, J=8.0, 7.6 Hz, 1H), 4.56 (brs, 1H), 3.62 (t, J=6.4 Hz, 2H), 3.54 (m, 2H), 2.72 (t, J=6.0 Hz, 2H), 2.64 (t, J=5.2 Hz, 2H), 1.82 (quint, J=6.0 Hz, 2H).

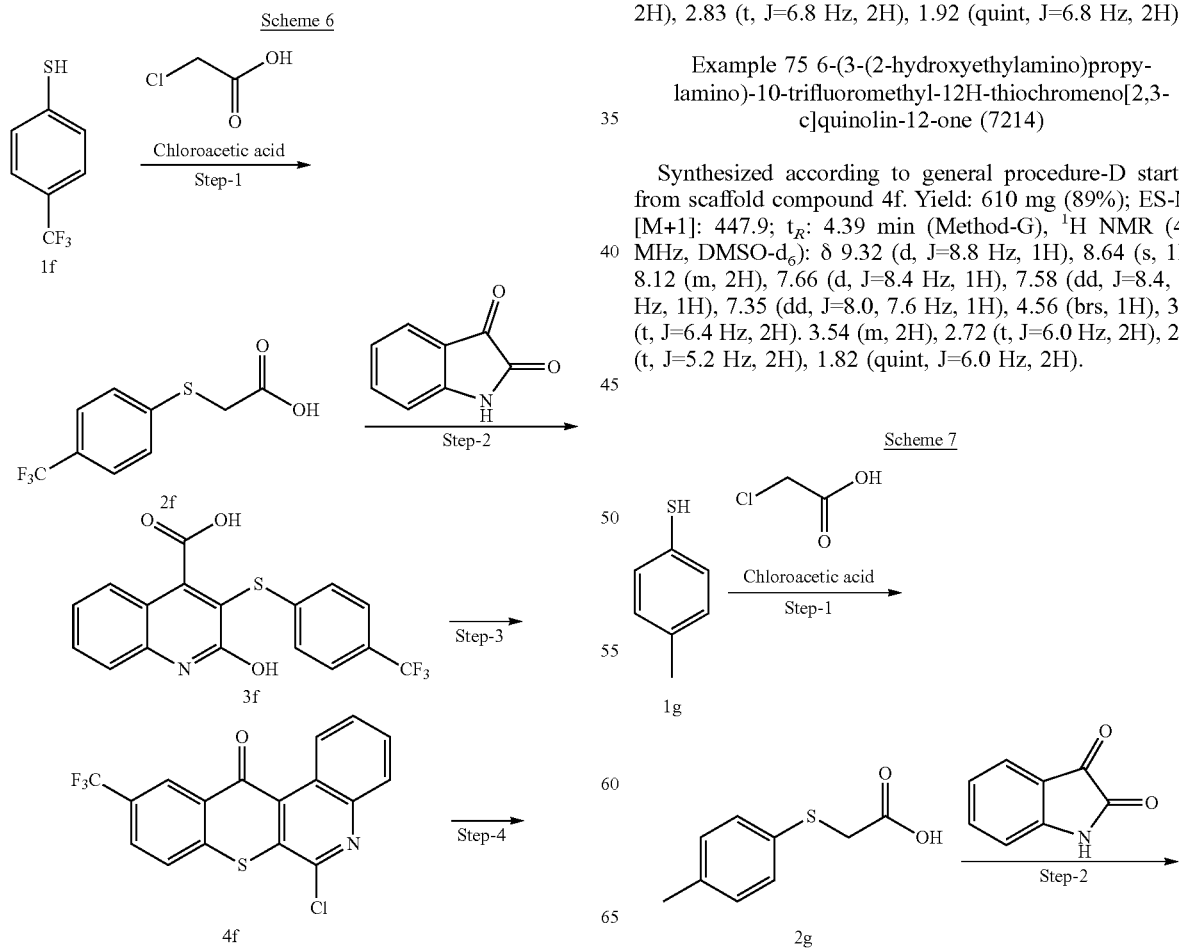

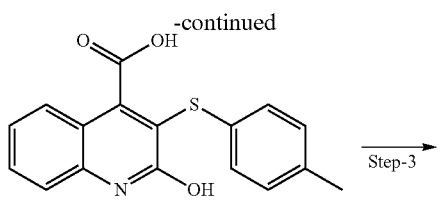

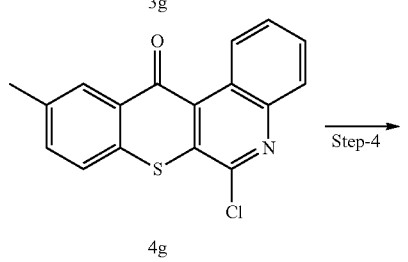

Example 76 6-chloro-10-methyl-12H-thiochromeno[2,3-c]quinolin-12-one (4g)

Synthesized starting from 4-methylbenzenethiol in 3 steps following general procedures A-C. Yield: 48% over 3 steps. ES-MS [M+1]$^+$: 311.9; $t_R$: 8.65 min (Method-G).

Example 77 6-(3-aminopropylamino)-10-methyl-12H-thiochromeno[2,3-c]quinolin-12-one (7202)

Synthesized according to general procedure-E starting from scaffold compound 4g. Yield: 130 mg (63%). ES-MS [M+1]$^+$: 350.0; $t_R$: 2.28 min (Method-E), $^1$H NMR (400 MHz, DMSO-d$_6$): δ 9.34 (d, J=8.8 Hz, 1H), 8.25 (s, 1H), 8.07 (m, 3H), 7.79 (d, J=8.4 Hz, 1H), 7.69-7.64 (m, 2H), 7.58 (td, J=8.4, 2.0 Hz, 1H), 7.37-7.33 (m, 2H), 3.66 (t, J=5.6 Hz, 2H), 2.87 (t, J=7.2 Hz, 2H), 2.47 (s, 3H; merged with residual DMSO), 2.00 (quint, J=6.8 Hz, 2H).

Example 78 6-(3-(2-hydroxyethylamino)propylamino)-10-methyl-12H-thiochromeno[2,3-c]quinolin-12-one (7215)

Synthesized according to general procedure-D starting from scaffold compound 4g. Yield: 210 mg (55%). ES-MS [M+1]$^+$: 394.0; $t_R$: 4.08 min (Method-G), $^1$H NMR (400 MHz, DMSO-d$_6$): δ 9.35 (d, J=8.8 Hz, 1H), 8.24 (s, 1H), 7.77 (d, J=8.0 Hz, 1H), 7.65 (m, 2H), 7.56 (t, J=7.6 Hz, 1H), 7.34 (t, J=7.6 Hz, 1H), 4.7 (brs, 1H), 3.63 (m, 2H), 3.56 (m, 2H), 2.75 (t, J=5.6 Hz, 2H), 2.67 (t, J=5.6 Hz, 2H), 1.85 (m, 2H).

Example 79 6-(2-aminoethylamino)-10-methyl-12H-thiochromeno[2,3-c]quinolin-12-one (7231)

Synthesized according to general procedure-E starting from scaffold compound 4g. Yield: 163 mg (52%). ES-MS [M+1]$^+$: 335.9; $t_R$: 4.15 min (Method-G), $^1$H NMR (400 MHz, DMSO-d$_6$): δ 9.34 (d, J=8.8 Hz, 1H), 8.25 (s, 1H), 7.82 (d, J=8.4 Hz, 1H), 7.66 (m, 2H), 7.57 (t, J=7.6 Hz, 1H), 7.35 (t, J=7.6 Hz, 1H), 3.57 (t, J=6.4 Hz, 2H), 2.87 (t, J=6.4 Hz, 2H), 2.47 (s, 3H; merged with residual DMSO).

Example 80 6-(ethylamino)-10-methyl-12H-thiochromeno[2,3-c]quinolin-12-one (7232)

Synthesized according to general procedure-J starting from scaffold compound 4f. Yield: 95 mg (30%). ES-MS [M+1]$^+$: 321.0; $t_R$: 6.10 min (Method-E), $^1$H NMR (400 MHz, DMSO-d$_6$): δ 9.39 (dd, J=8.4, 1.2 Hz, 1H), 8.30 (s, 1H), 7.86 (d, J=8.4 Hz, 1H), 7.69 (dd, J=7.6, 6.4 Hz, 2H), 7.60 (ddd, J=6.8, 5.6, 1.6 Hz, 1H), 7.38 (td, J=7.2, 5.6 Hz, 1H), 7.16 (t, J=5.2 Hz, 1H), 3.59-3.66 (m, 2H), 2.47 (s, 3H; merged with residual DMSO), 1.23-1.33 (m, 3H).

Example 81 6-(benzylamino)-10-methyl-12H-thiochromeno[2,3-c]quinolin-12-one (7233)

Synthesized according to general procedure-D starting from scaffold compound 4g. Yield: 178 mg (55%). ES-MS [M+1]$^+$: 382.9; $t_R$: 8.41 min (Method-G), $^1$H NMR (400 MHz, DMSO-d$_6$): δ 9.34 (d, J=8.8 Hz, 1H), 8.26 (s, 1H), 7.83 (d, J=8.0 Hz, 1H), 7.76 (t, J=5.6 Hz, 2H), 7.70-7.62 (m, 2H), 7.55 (t, J=8.0 Hz, 1H), 7.45 (m, 2H), 7.34 (td, J=8.4, 1.6 Hz, 1H), 7.28 (m, 2H), 7.18 (t, J=7.2 Hz, 1H), 4.79 (d, J=5.6 Hz, 2H).

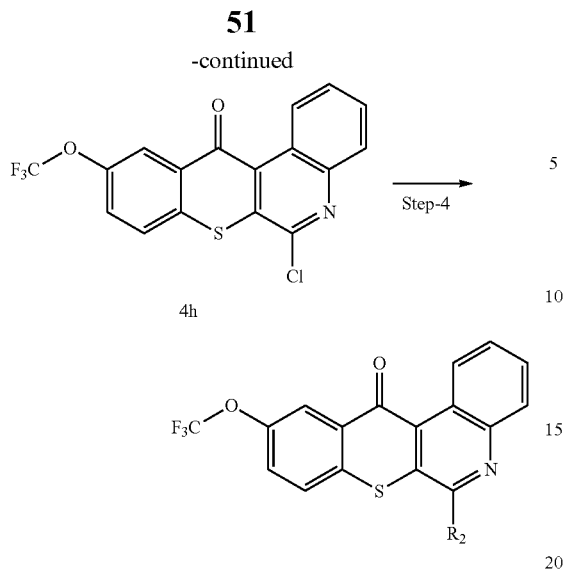

4h

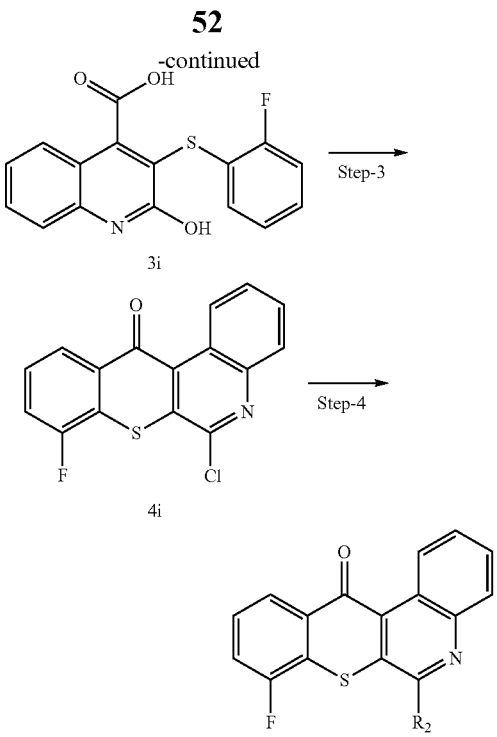

Example 82 6-chloro-10-trifluoromethoxy-12H-thiochromeno[2,3-c]quinolin-12-one (4h)

Synthesized starting from 4-(trifluoromethoxy)thiophenol in 3 steps following general procedures A-C. Yield: 25% over 3 steps. ES-MS [M+1]$^+$: 381.9; $t_R$: 5.90 min (Method-F).

Example 83 6-(3-aminopropylamino)-10-(trifluoromethoxy)-12H-thiochromeno[2,3-c]quinolin-12-one (7203)

Synthesized according to general procedure-E starting from scaffold compound 4h. Yield: 75 mg (23%). ES-MS [M+1]$^+$: 419.9; $t_R$: 4.55 min (Method-G), $^1$H NMR (400 MHz, DMSO-d$_6$): δ 9.36 (d, J=8.0 Hz, 1H), 8.31 (s, 1H), 8.12 (d, J=8.8 Hz, 1H), 7.90-7.87 (m, 4H), 7.70 (d, J=8.0 Hz, 1H), 7.62 (t, J=7.2 Hz, 1H), 7.39 (t, J=8.0 Hz, 1H), 3.66 (t, J=6.4 Hz, 2H), 2.89 (t, J=7.2 Hz, 2H), 1.99 (m, 2H).

Scheme 9

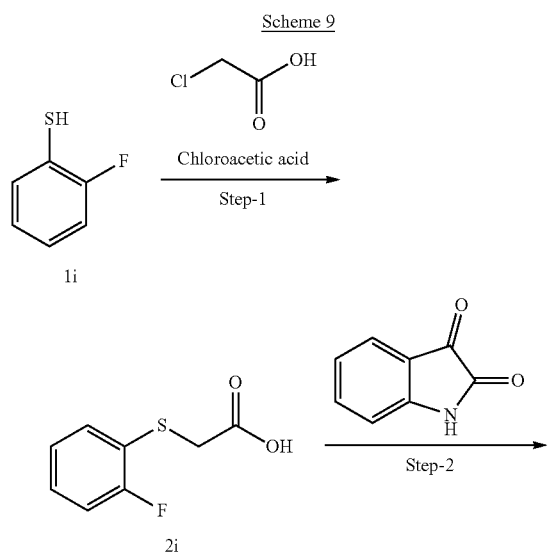

Example 84 6-chloro-8-fluoro-12H-thiochromeno[2,3-c]quinolin-12-one (4i)

Synthesized starting from 2-fluorothiophenol in 3 steps following general procedures A-C. Yield: 54% over 3 steps. ES-MS [M+1]$^+$: 315.8; $t_R$: 7.88 min (Method-G).

Example 85 6-(3-aminopropylamino)-8-fluoro-12H-thiochromeno[2,3-c]quinolin-12-one (7211)

Synthesized according to general procedure-E starting from scaffold compound 4i. Yield: 145 mg (37%). ES-MS [M+1]$^+$: 353.9; $t_R$: 4.01 min (Method-G), $^1$H NMR (400 MHz, DMSO-d$_6$): δ 9.31 (d, J=8.4 Hz, 1H), 8.29 (d, J=8.0 Hz, 1H), 7.92 (brs, 2H), 7.81 (dd, J=9.2, 8.8 Hz, 1H), 7.74-7.70 (m, 2H), 7.61 (dd, J=7.6, 7.2 Hz, 1H), 7.5 (brs, 1H), 7.38 (dd, J=8.4, 6.8 Hz, 1H), 3.67 (t, J=6.4 Hz, 2H), 2.89 (t, J=6.8 Hz, 2H), 2.00 (quint, J=6.4 Hz, 2H).

Example 86 8-fluoro-6-(3-(2-hydroxyethylamino)propylamino)-12H-thiochromeno[2,3-c]quinolin-12-one (7224)

Synthesized according to general procedure-D starting from scaffold compound 4i. Yield: 125 mg (28%). ES-MS [M+1]$^+$: 398.0; $t_R$: 4.03 min (Method-G), $^1$H NMR (400 MHz, DMSO-d$_6$): δ 9.31 (d, J=8.0 Hz, 1H), 8.74 (brs, 1H), 8.29 (d, J=8.0 Hz, 1H), 7.82 (dd, J=9.2, 8.8 Hz, 1H), 7.72 (m, 2H), 7.61 (t, J=7.6 Hz, 1H), 7.5 (brs, 1H), 7.38 (t, J=8.0 Hz, 1H), 5.26 (brs, 1H), 3.65 (m, 4H), 2.99 (m, 4H), 2.08 (m, 2H).

Example 87 6-(2-aminoethylamino)-8-fluoro-12H-thiochromeno[2,3-c]quinolin-12-one (7240)

Synthesized according to general procedure-E starting from scaffold compound 4i. Yield: 102 mg (31%). ES-MS [M+1]$^+$: 340.0; $t_R$: 3.98 min (Method-G), $^1$H NMR (400

MHz, DMSO-d$_6$): δ 9.30 (d, J=8.8 Hz, 1H), 8.27 (d, J=7.6 Hz, 1H), 7.80 (dd, J=9.2, 8.8 Hz, 1H), 7.72-7.66 (m, 2H), 7.58 (dd, J=7.6, 6.8 Hz, 1H), 7.35 (dd, J=8.0, 7.2 Hz, 1H), 3.57 (t, J=6.4 Hz, 2H), 2.86 (t, J=6.4 Hz, 2H).

Example 88 6-(ethylamino)-8-fluoro-12H-thiochromeno[2,3-c]quinolin-12-one (7241)

Synthesized according to general procedure-J starting from scaffold compound 4i. Yield: 164 mg (53%). ES-MS [M+1]$^+$: 324.9; t$_R$: 5.97 min (Method-E), $^1$H NMR (400 MHz, DMSO-d$_6$): δ 9.29 (d, J=8.0 Hz, 1H), 8.26 (d, J=8.0 Hz, 1H), 7.79 (t, J=8.8 Hz, 1H), 7.71-7.65 (m, 2H), 7.57 (t, J=7.6 Hz, 1H), 7.36-7.29 (m, 2H), 3.59 (m, 2H), 1.25 (t, J=6.8 Hz, 3H).

Example 89 6-(benzylamino)-8-fluoro-12H-thiochromeno[2,3-c]quinolin-12-one (7242)

Synthesized according to general procedure-D starting from scaffold compound 4i. Yield: 255 mg (69%). ES-MS [M+1]$^+$: 386.9; t$_R$: 6.41 min (Method-E), $^1$H NMR (400 MHz, DMSO-d$_6$): δ 9.29 (d, J=8.4 Hz, 1H), 8.27 (d, J=8.0 Hz, 1H), 7.98 (t, J=5.2 Hz, 1H), 7.79 (dd, J=9.2, 8.8 Hz, 1H), 7.69 (m, 1H), 7.62 (d, J=8.0 Hz, 1H), 7.56 (dd, J=7.6, 6.8 Hz, 1H), 7.45 (m, 2H), 7.35 (dd, J=7.6, 6.8 Hz, 1H), 7.28 (m, 2H), 7.17 (dd, J=7.2, 6.8 Hz, 1H), 4.78 (d, J=5.2 Hz, 2H).

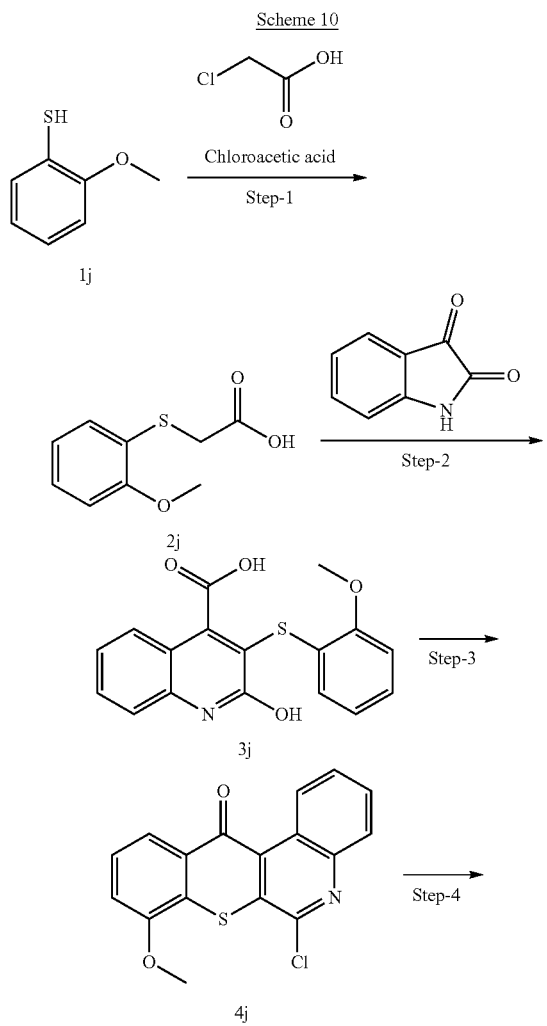

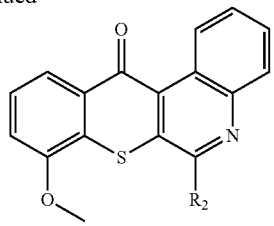

Example 90 6-chloro-8-methoxy-12H-thiochromeno[2,3-c]quinolin-12-one (4j)

Synthesized starting from 2-methoxythiophenol in 3 steps following general procedures A-C. Yield: 46% over 3 steps.

Example 91 6-(3-aminopropylamino)-8-methoxy-12H-thiochromeno[2,3-c]quinolin-12-one (7212)

Synthesized according to general procedure-E starting from scaffold compound 4j. Yield: 128 mg (33%); ES-MS [M+1]$^+$: 366.0; t$_R$: 3.59 min (Method-I), $^1$H NMR (400 MHz, DMSO-d$_6$): δ 9.35 (d, J=8.0 Hz, 1H), 8.05 (d, J=8.0 Hz, 1H), 7.66-7.61 (m, 2H), 7.57 (m, 1H), 7.47 (d, J=7.6 Hz, 1H), 7.33 (dd, J=8.0, 1.2 Hz, 1H), 4.04 (s, 3H), 3.65 (t, J=6.8 Hz, 2H), 2.66 (t, J=6.4 Hz, 2H), 1.76 (quint, J=6.4 Hz, 2H).

Example 92 6-(3-(2-hydroxyethylamino)propylamino)-8-methoxy-12H-thiochromeno[2,3-c]quinolin-12-one (7225)

Synthesized according to general procedure-D starting from scaffold compound 4j. Yield: 266 mg (71%). ES-MS [M+1]$^+$: 410.0; t$_R$: 4.02 min (Method-G), $^1$H NMR (400 MHz, DMSO-d$_6$): δ 9.35 (d, J=8.4 Hz, 1H), 8.04 (d, J=7.6 Hz, 1H), 7.66-7.60 (m, 2H), 7.55 (dd, J=8.4, 1.2 Hz, 1H), 7.45 (d, J=7.6 Hz, 1H), 7.32 (dd, J=8.4, 1.2 Hz, 1H), 4.51 (brs, 1H), 4.03 (s, 3H), 3.65-3.58 (m, 4H), 2.71 (t, J=6.0 Hz, 2H), 2.63 (t, J=6.4 Hz, 2H), 1.82 (quint, J=6.4 Hz, 2H).

Example 93 6-(2-aminoethylamino)-8-methoxy-12H-thiochromeno[2,3-c]quinolin-12-one (7244)

Synthesized according to general procedure-E starting from scaffold compound 4j. Yield: 151 mg (47%); ES-MS [M+1]$^+$: 352.0; t$_R$: 4.01 min (Method-G), $^1$H NMR (400 MHz, DMSO-d$_6$): δ 9.37 (d, J=8.4 Hz, 1H), 8.38 (s, 1H), 8.06 (d, J=8.4 Hz, 1H), 7.71 (d, J=8.4 Hz, 1H), 7.65 (t, J=8.0 Hz, 1H), 7.60 (dd, J=8.4, 7.2 Hz, 1H), 7.49 (d, J=8.0 Hz, 1H), 7.38 (dd, J=8.4, 8.0 Hz, 1H), 4.05 (s, 3H), 3.80 (t, J=6.0 Hz, 2H), 3.12 (t, J=6.0 Hz, 2H)

Example 94 6-(ethylamino)-8-methoxy-12H-thiochromeno[2,3-c]quinolin-12-one (7245)

Synthesized according to general procedure-J starting from scaffold compound 4j. Yield: 196 mg (63%); ES-MS [M+1]$^+$: 336.9; t$_R$: 7.04 min (Method-G), $^1$H NMR (400 MHz, DMSO-d$_6$): δ 9.35 (d, J=8.0 Hz, 1H), 8.05 (d, J=7.6 Hz, 1H), 7.66 (d, J=8.4 Hz, 1H), 7.62 (d, J=8.4 Hz, 1H), 7.56 (td, J=8.0, 1.2 Hz, 1H), 7.47 (d, J=8.0 Hz, 1H), 7.34 (td, J=8.4, 1.2 Hz, 1H), 7.27 (brs, 1H), 4.04 (s, 3H), 3.6 (m, 2H), 1.25 (t, J=7.2 Hz, 3H).

Example 95 6-(benzylamino)-8-methoxy-12H-thiochromeno[2,3-c]quinolin-12-one (7246)

Synthesized according to general procedure-D starting from scaffold compound 4j. Yield: 144 mg (39%); ES-MS [M+1]$^+$: 399.0; $t_R$: 7.76 min (Method-G), $^1$H NMR (400 MHz, DMSO-d$_6$): δ 9.35 (d, J=8.4 Hz, 1H), 8.06 (d, J=8.0 Hz, 1H), 7.93 (m, 1H), 7.64 (m, 2H), 7.56 (m, 1H), 7.49-7.45 (m, 3H), 7.34 (dd, J=8.4, 8.0 Hz, 1H), 7.28 (m, 2H), 7.18 (m, 1H), 4.79 (d, J=5.6 Hz, 2H), 4.05 (s, 3H).

Example 96 tert-butyl 4-(8-methoxy-12-oxo-12H-thiochromeno[2,3-c]quinolin-6-yl)piperazine-1-carboxylate (7297)

Synthesized according to general procedure-D starting from scaffold compound 4j. Yield: 260 mg (60%); ES-MS [M+1]$^+$: 478.0; $t_R$: 7.11 min (Method-E), $^1$H NMR (400 MHz, DMSO-d$_6$): δ 9.55 (d, J=8.8 Hz, 1H), 8.08 (d, J=8.4 Hz, 1H), 7.94 (d, J=8.4 Hz, 1H), 7.75 (dd, J=8.0, 7.2 Hz, 1H), 7.67-7.61 (m, 2H), 7.48 (d, J=8.0 Hz, 1H), 4.05 (s, 3H), 3.61 (brs, 4H), 3.28 (brs, 4H), 1.43 (s, 9H).

Example 97 8-methoxy-6-(piperazin-1-yl)-12H-thiochromeno[2,3-c]quinolin-12-one (7247)

Synthesized according to general procedure-F using N-Boc piperazine instead of 4-methoxybenzylamine in first stage. Yield: 206 mg (98%); ES-MS [M+1]$^+$: 378.0; $t_R$: 4.32 min (Method-G), $^1$H NMR (400 MHz, DMSO-d$_6$): δ 9.55 (d, J=8.4 Hz, 1H), 8.99 (brs, 1H), 8.07 (d, J=8.0 Hz, 1H), 7.95 (d, J=8.0 Hz, 1H), 7.77 (m, 1H), 7.67-7.61 (m, 2H), 7.49 (d, J=8.0 Hz, 1H), 4.04 (s, 3H), 3.53 (m, 4H), 3.40 (m, 4H).

Scheme 11

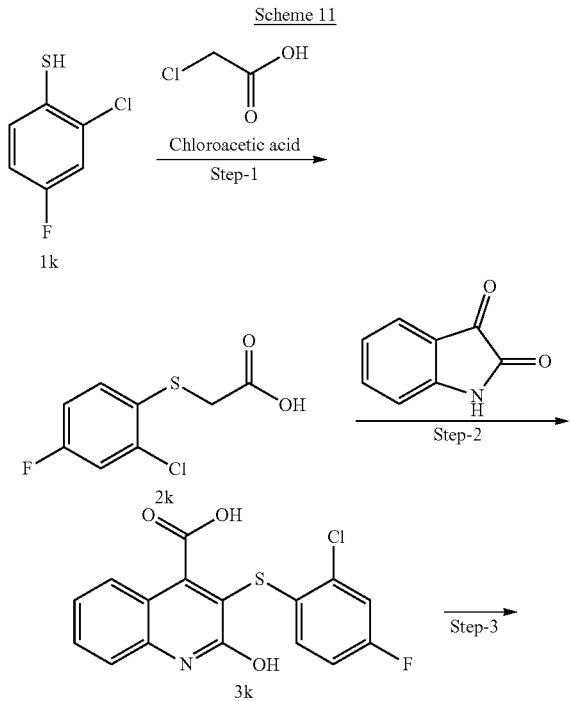

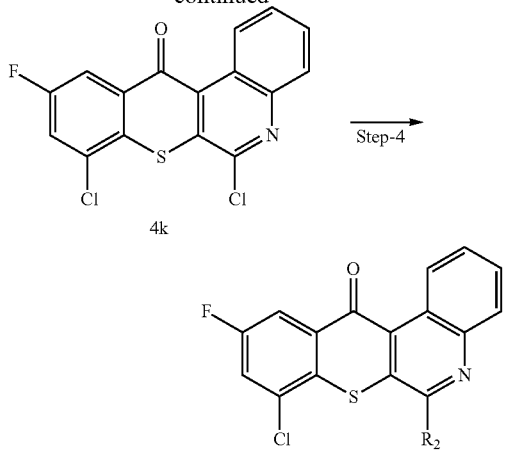

Example 98 6,8-dichloro-10-fluoro-12H-thiochromeno[2,3-c]quinolin-12-one (4k)

Synthesized starting from 2-chloro-4-fluorobenzenethiol in 3 steps following general procedures A-C. Yield: 40% over 3 steps. ES-MS [M+H]$^+$: 351.8; $t_R$: 9.41 min (Method-E).

Example 99 6-(3-aminopropylamino)-8-chloro-10-fluoro-12H-thiochromeno[2,3-c]quinolin-12-one (7213)

Synthesized according to general procedure-E starting from scaffold compound 4k. Yield: 108 mg (33%); ES-MS [M+1]$^+$: 388.0; $t_R$: 4.45 min (Method-G), $^1$H NMR (400 MHz, DMSO-d$_6$): δ 9.35 (dd, J=8.8, 1.2 Hz, 1H), 8.24-8.19 (m, 2H), 7.77 (t, J=4.8 Hz, 1H), 7.73-7.70 (m, 1H), 7.65-7.61 (m, 1H), 7.43-7.38 (m, 1H), 3.74-3.67 (m, 2H), 3.33 (m, 2H; merged with H—O-D signal), 2.08-1.97 (m, 2H).

Example 100 8-chloro-10-fluoro-6-(3-(2-hydroxyethylamino)propylamino)-12H-thiochromeno[2,3-c]quinolin-12-one (7226)

Synthesized according to general procedure-D starting from scaffold compound 4k. Yield: 172 mg (40%). ES-MS [M+1]$^+$: 431.9; $t_R$: 4.42 min (Method-G), $^1$H NMR (400 MHz, DMSO-d$_6$): δ 9.31 (d, J=8.4 Hz, 1H), 8.72 (brs, 1H), 8.21-8.15 (m, 2H), 7.70 (d, J=8.0 Hz, 1H), 7.61 (t, J=7.6 Hz, 1H), 7.53 (brs, 1H), 7.38 (t, J=7.6 Hz, 1H), 5.25 (brs, 1H), 3.65 (m, 4H), 3.01 (m, 4H), 2.08 (m, 2H).

Example 101 6-(2-aminoethylamino)-8-chloro-10-fluoro-12H-thiochromeno[2,3-c]quinolin-12-one (7248)

Synthesized according to general procedure-E starting from scaffold compound 4k. Yield: 100 mg (31%); ES-MS [M+1]$^+$: 374.0; $t_R$: 4.38 min (Method-G), $^1$H NMR (400 MHz, DMSO-d$_6$): δ 9.33 (d, J=8.4 Hz, 1H), 8.21 (m, 2H), 7.72 (td, J=6.8, 1.6 Hz, 1H), 7.62 (td, J=8.0, 6.8 Hz, 1H), 7.39 (td, J=6.8, 2.8 Hz, 1H), 3.62 (t, J=6.8 Hz, 2H), 2.91 (t, J=6.4 Hz, 2H).

Example 102 8-chloro-6-(ethylamino)-10-fluoro-12H-thiochromeno[2,3-c]quinolin-12-one (7249)

Synthesized according to general procedure-J starting from scaffold compound 4k. Yield: 87 mg (28%). ES-MS

[M+1]+: 358.8; $t_R$: 6.88 min (Method-E), 1H NMR (400 MHz, DMSO-d6): δ 9.27 (d, J=8.8 Hz, 1H), 8.13 (m, 2H), 7.65 (d, J=8.4 Hz, 1H), 7.58 (m, 1H), 7.36-7.30 (m, 2H), 3.59 (m, 2H), 1.26 (t, J=6.8 Hz, 3H).

Example 103 6-(benzylamino)-8-chloro-10-fluoro-12H-thiochromeno[2,3-c]quinolin-12-one (7250)

Synthesized according to general procedure-D starting from scaffold compound 4k. Yield: 175 mg (48%). ES-MS [M+1]+: 420.9; $t_R$: 7.19 min (Method-E), 1H NMR (400 MHz, DMSO-d6): δ 9.23 (d, J=8.4 Hz, 1H), 8.15 (m, 2H), 7.99 (m, 1H), 7.61 (d, J=8.0 Hz, 1H), 7.56 (m, 1H), 7.45 (m, 2H), 7.34 (t, J=7.2 Hz, 1H), 7.28 (m, 2H), 7.19 (m, 1H), 4.78 (d, J=4.4 Hz, 2H).

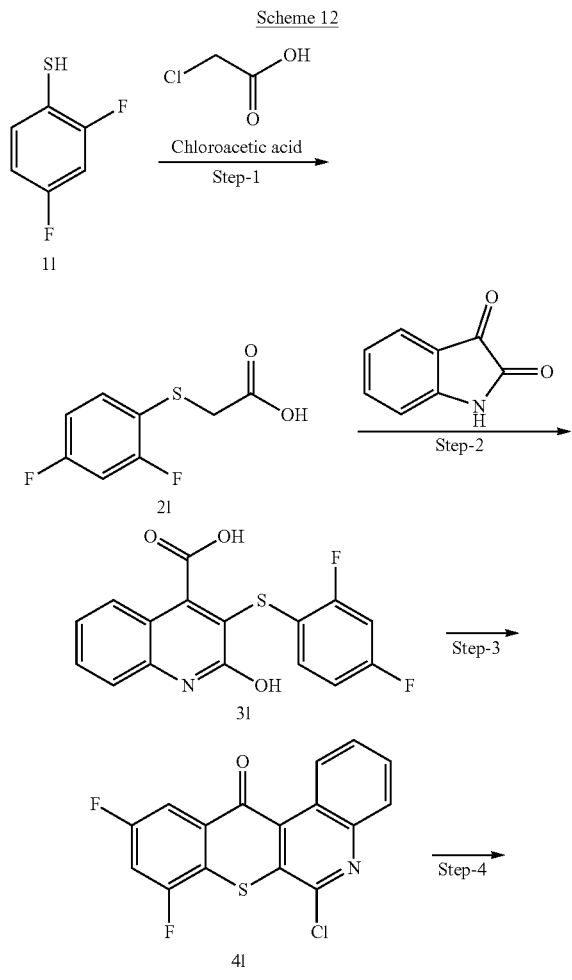

Example 104 6-chloro-8,10-difluoro-12H-thiochromeno[2,3-c]quinolin-12-one (4l)

Synthesized starting from 2,4-difluorobenzenethiol in 3 steps following general procedures A-C. Yield: 13% over 3 steps. ES-MS [M+H]+: 333.9; $t_R$: 8.25 min (Method-G).

Example 105 6-(3-aminopropylamino)-8,10-difluoro-12H-thiochromeno[2,3-c]quinolin-12-one (7252)

Synthesized according to general procedure-E starting from scaffold compound 4l. Yield: 255 mg (76%). ES-MS [M+1]+: 372.1; $t_R$: 4.27 min (Method-G), 1H NMR (400 MHz, DMSO-d6): δ 9.34 (d, J=8.4 Hz, 1H), 8.12-8.00 (m, 2H), 7.96-7.74 (m, 2H), 7.69-7.60 (m, 1H), 7.41 (dd, J=7.2, 6.8 Hz, 1H), 3.69 (t, J=6.4 Hz, 2H), 2.91 (t, J=7.2 Hz, 2H), 2.02 (m, 2H).

Example 106 8,10-difluoro-6-(3-(2-hydroxyethylamino)propylamino)-12H-thiochromeno[2,3-c]quinolin-12-one (7253)

Synthesized according to general procedure-D starting from scaffold compound 4l. Yield: 130 mg (42%). ES-MS [M+1]+: 416.1; $t_R$: 4.23 min (Method-G), 1H NMR (400 MHz, DMSO-d6): δ 9.36 (d, J=8.8 Hz, 1H), 8.85 (brs, 1H), 8.03-8.14 (m, 2H), 7.76 (d, J=7.6 Hz, 1H), 7.65 (td, J=7.2, 6.8 Hz, 1H), 7.57 (m, 1H), 7.41 (dd, J=8.4, 6.8 Hz, 1H), 5.28 (t, J=5.2 Hz, 1H), 3.67 (m, 4H), 2.99-3.06 (m, 4H), 2.07-2.14 (m, 2H).

Example 107 6-(2-aminoethylamino)-8,10-difluoro-12H-thiochromeno[2,3-c]quinolin-12-one (7254)

Synthesized according to general procedure-E starting from scaffold compound 4l. Yield: 25 mg (8%). ES-MS [M+1]+: 358.0; $t_R$: 4.26 min (Method-G), 1H NMR (400 MHz, DMSO-d6): δ 9.36 (d, J=8.4 Hz, 1H), 8.05-7.98 (m, 2H), 7.70 (d, J=8.0 Hz, 1H), 7.62 (ddd, J=8.0, 6.8, 1.2 Hz, 1H), 7.39 (ddd, J=8.4, 6.8, 1.6 Hz, 1H), 3.61 (t, J=9.6 Hz, 2H), 2.90 (t, J=9.6 Hz, 2H).

Example 108 6-(ethylamino)-8,10-difluoro-12H-thiochromeno[2,3-c]quinolin-12-one (7255)

Synthesized according to general procedure-J starting from scaffold compound 4l. Yield: 128 mg (42%). ES-MS [M+1]+: 343.0; $t_R$: 6.27 min (Method-E), 1H NMR (400 MHz, DMSO-d6): δ 9.32 (dd, J=8.4, 0.8 Hz, 1H), 8.05 (m, 2H), 7.69 (dd, J=8.4, 1.2 Hz, 1H), 7.61 (td, J=6.8, 1.2 Hz, 1H), 7.39 (dd, J=6.8, 1.2 Hz, 1H), 7.34 (t, J=5.2 Hz, 1H), 3.62 (m, 2H), 1.27 (t, J=6.0 Hz, 3H).

Example 109 6-(benzylamino)-8,10-difluoro-12H-thiochromeno[2,3-c]quinolin-12-one (7256)

Synthesized according to general procedure-D starting from scaffold compound 4l. Yield: 95 mg (52%). ES-MS [M+1]+: 405.0; $t_R$: 6.62 min (Method-E), 1H NMR (400 MHz, DMSO-d6): δ 9.34 (dd, J=8.4, 1.2 Hz, 1H), 8.05 (m, 3H), 7.67 (dd, J=8.4, 1.2 Hz, 1H), 7.61 (td, J=6.8, 1.2 Hz, 1H), 7.48 (dd, J=8.4, 1.2 Hz, 2H), 7.39 (td, J=6.8, 1.6 Hz, 1H), 7.31 (t, J=7.2 Hz, 2H), 7.21 (t, J=7.2 Hz, 1H), 4.87 (d, J=5.6 Hz, 2H).

Scheme 13

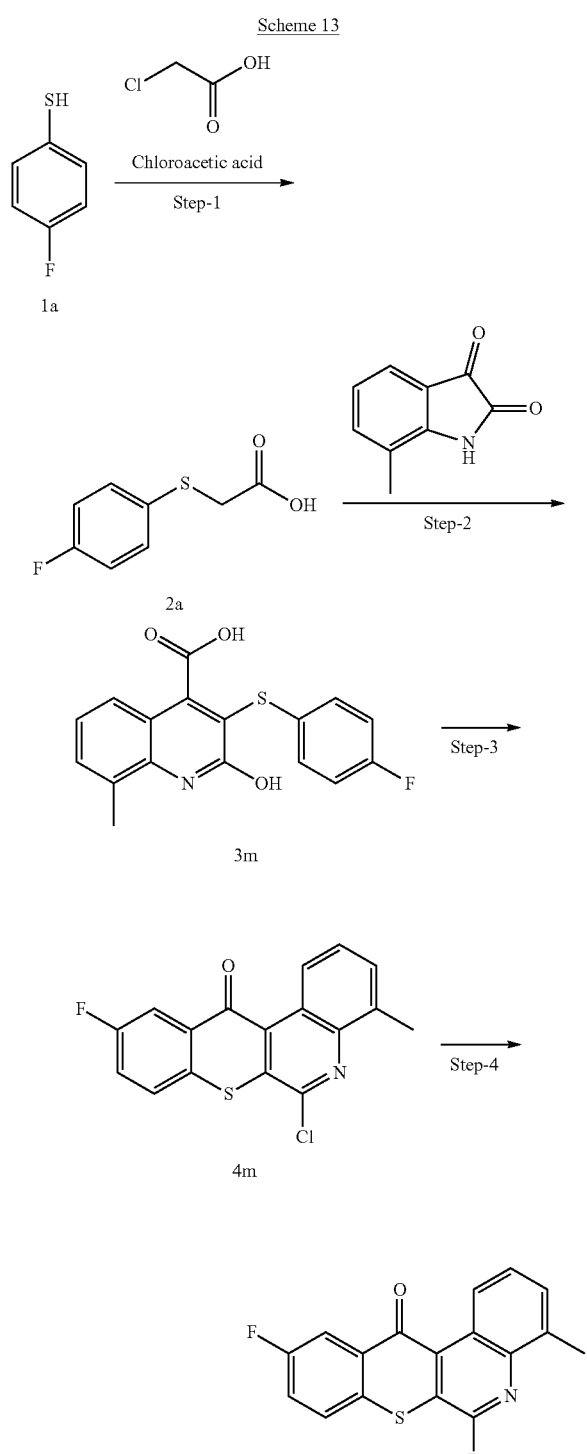

Example 110 6-chloro-10-fluoro-4-methyl-12H-thiochromeno[2,3-c]quinolin-12-one (4m)

Synthesized in 2 steps starting from 7-methylisatin and compound 2a using general procedures B-C. Yield: 51% over 2 steps. ES-MS [M+1]$^+$: 329.9; $t_R$: 4.19 min (Method-K).

Scheme 14

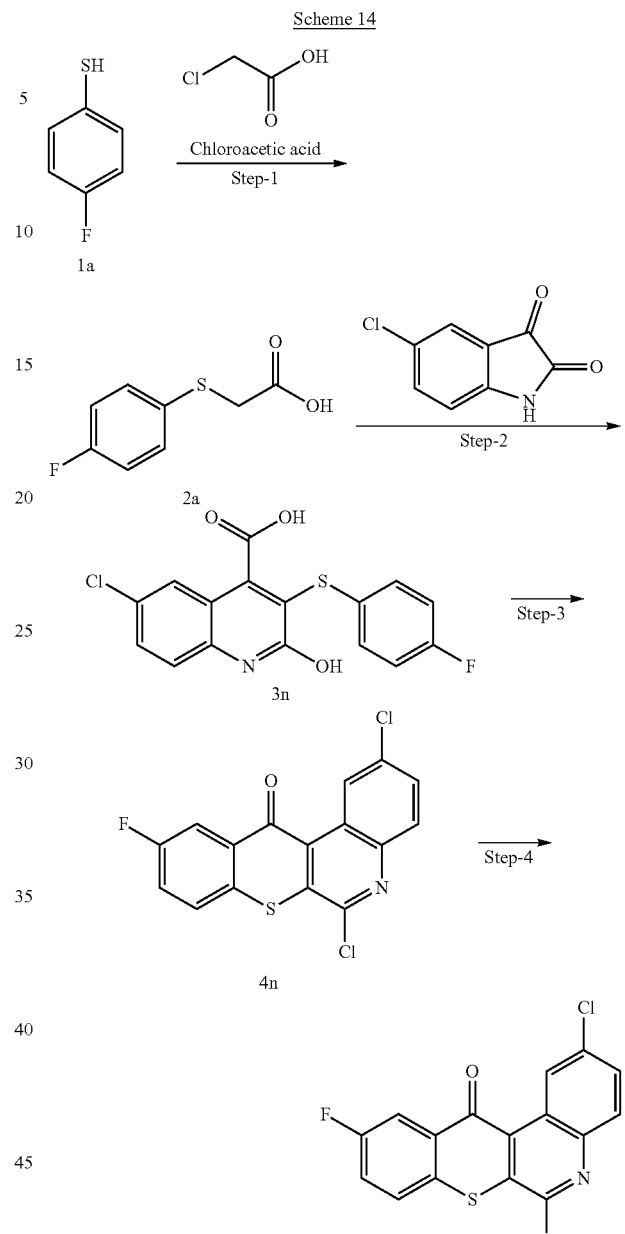

Example 111 2,6-dichloro-O-fluoro-12H-thiochromeno[2,3-c]quinolin-12-one (4n)

Synthesized in 2 steps starting from 5-chloroisatin and compound 2a using general procedures B-C. Yield: 40% over 2 steps. ES-MS [M+1]$^+$: 349.8; $t_R$: 9.39 min (Method-G).

Example 112 6-((3-aminopropyl)amino)-2-chloro-10-fluoro-12H-thiochromeno[2,3-c]quinolin-12-one (7403)

Synthesized according to general procedure-D starting from scaffold compound 4n. Yield: 150 mg (46%). ES-MS [M+1]$^+$: 387.9; $t_R$: 3.44 min (Method-F), $^1$H NMR (400 MHz, DMSO-d$_6$): δ 9.42 (d, J=2.4 Hz, 1H), 8.14-8.10 (m, 3H), 8.01 (dd, J=8.8, 4.8 Hz, 1H), 7.77 (ddd, J=8.8, 8.4, 2.8 Hz, 1H), 7.65 (d, J=8.8 Hz, 1H), 7.59-7.57 (m, 2H), 3.63 (m, 2H), 2.87 (t, J=7.2 Hz, 2H), 2.0 (m, 2H).

Example 113 2-chloro-10-fluoro-6-(3-(2-hydroxyethylamino)propylamino)-12H-thiochromeno[2,3-c]quinolin-12-one (7406)

Synthesized according to general procedure-D starting from scaffold compound 4n. Yield: 126 mg (34%). ES-MS [M+1]⁺: 431.9; $t_R$: 4.48 min (Method-G); ¹H NMR (400 MHz, DMSO-d₆): δ 9.46 (d, J=2.4 Hz, 1H), 8.8 (brs, 1H), 8.17 (dd, J=9.6, 2.8 Hz, 1H), 8.05 (dd, J=8.8, 4.8 Hz, 1H), 7.80 (td, J=8.8, 2.8 Hz, 1H), 7.69 (d, J=8.8 Hz, 1H), 7.61 (dd, J=8.8, 2.4 Hz, 1H), 7.59 (brs, 1H), 5.24 (m, 1H), 3.65 (m, 4H), 3.01-2.94 (m, 4H), 2.07 (m, 2H).

Example 114 6-(benzylamino)-2-chloro-10-fluoro-12H-thiochromeno[2,3-c]quinolin-12-one (7416)

Synthesized according to general procedure-D starting from scaffold compound 4n. Yield: 259 mg (71%), ES-MS [M+1]⁺: 421.0, $t_R$: 7.42 min (Method-E), ¹H NMR (400 MHz, DMSO-d₆): δ 9.48 (d, J=2.0 Hz, 1H), 9.05 (d, J=2.0 Hz, 1H), 9.05 (d, J=2.8 Hz, 1H), 9.05 (d, J=2.8 Hz, 1H), 9.05 (d, J=2.8 Hz, 1H).

Scheme 15

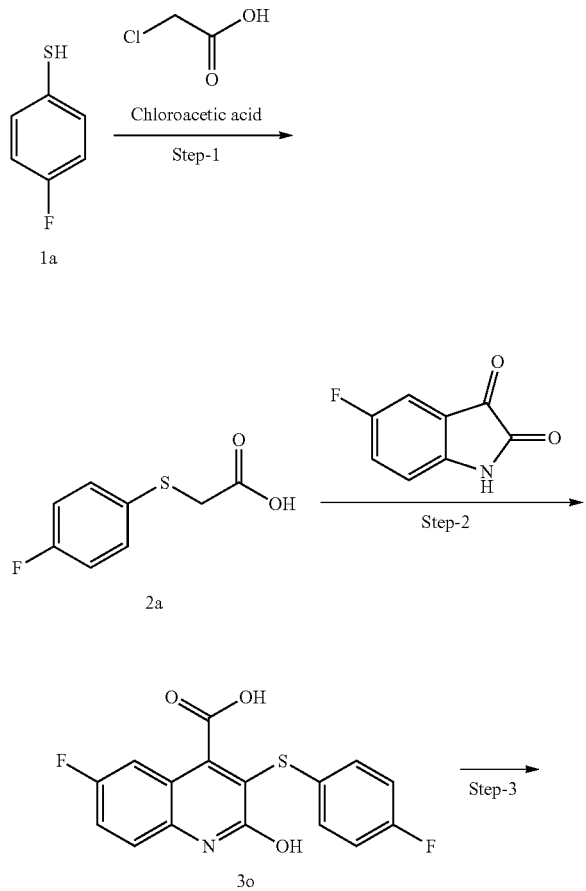

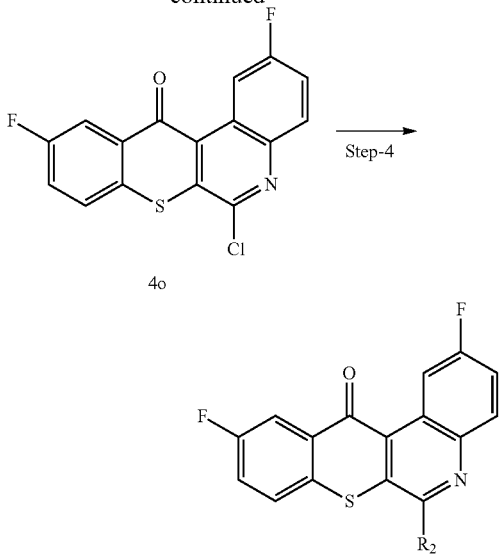

Example 115 6-chloro-2,10-difluoro-12H-thiochromeno[2,3-c]quinolin-12-one (4o)

Synthesized in 2 steps starting from 5-fluoroisatin and compound 2a using general procedures B-C. Yield: 53% over 2 steps. ES-MS [M+1]⁺: 333.8; $t_R$: 7.90 min (Method-G).

Example 116 6-(3-aminopropylamino)-2,10-difluoro-12H-thiochromeno[2,3-c]quinolin-12-one (7402)

Synthesized according to general procedure-E starting from scaffold compound 4o. Yield: 200 mg (60%), ES-MS [M+1]+: 372.0, $t_R$: 4.21 min (Method-G), ¹H NMR (400 MHz, DMSO-d₆): δ 9.18 (dd, J=8.8, 2.8 Hz, 1H), 8.20 (brs, 2H), 8.15 (dd, J=9.6, 2.8 Hz, 1H), 8.04 (dd, J=9.2, 8.8 Hz, 1H), 7.79 (m, 1H), 7.72 (dd, J=9.2, 5.2 Hz, 1H), 7.50 (m, 1H), 7.44 (m, 1H), 3.643 (m, 2H), 2.86 (m, 2H), 2.02 (m, 2H).

Example 117 2,10-difluoro-6-(3-(2-hydroxyethylamino)propylamino)-12H-thiochromeno[2,3-c]quinolin-12-one (7408)

Synthesized according to general procedure-D starting from scaffold compound 4o. Yield: 190 mg (51%), ES-MS [M+1]⁺: 416.0, $t_R$: 4.20 min (Method-G), ¹H NMR (400 MHz, DMSO-d₆): δ 9.18 (dd, J=12.8, 3.2 Hz, 1H), 8.8 (brs, 1H), 8.15 (dd, J=10.0, 2.8 Hz, 1H), 8.04 (dd, J=8.8, 5.2 Hz, 1H), 7.79 (ddd, J=8.8, 8.4, 2.8 Hz, 1H), 7.73 (dd, J=8.8, 6 Hz, 1H), 7.53-7.45 (m, 2H), 5.25 (brs, 1H), 3.64 (m, 4H), 3.0-2.93 (m, 4H), 2.01 (m, 2H).

Example 118 6-(2-aminoethylamino)-2,10-difluoro-12H-thiochromeno[2,3-c]quinolin-12-one (7422)

Synthesized according to general procedure-E starting from scaffold compound 4o. Yield: 102 mg (31%), ES-MS [M+1]⁺: 357.9, $t_R$: 4.16 min (Method-F), ¹H NMR (400 MHz, DMSO-d₆): δ 9.20 (dd, J=12.8, 2.8 Hz, 1H), 8.18 (ddd, J=10.0, 9.6, 2.8 Hz, 1H), 8.09-8.05 (m, 4H), 7.83-7.75

(m, 2H), 7.54 (td, J=8.8, 2.8 Hz, 1H), 8.04 (dd, J=8.8, 5.2 Hz, 1H), 7.42 (t, J=4.8 Hz, 1H), 3.81 (m, 2H), 3.16 (m, 2H).

Example 119 6-(benzylamino)-2,10-difluoro-12H-thiochromeno[2,3-c]quinolin-12-one (7424)

Synthesized according to general procedure-D starting from scaffold compound 4o. Yield: 149 mg (41%), ES-MS [M+1]$^+$: 404.9, $t_R$: 6.49 min (Method-J), $^1$H NMR (400 MHz, DMSO-d$_6$): δ 9.18 (dd, J=12.8, 2.8 Hz, 1H), 8.16 (ddd, J=10.0, 9.6, 2.8 Hz, 1H), 8.06 (m, 1H), 7.82-7.76 (m, 2H), 7.66 (dd, J=8.8, 6 Hz, 1H), 7.49-7.43 (m, 3H), 7.28 (m, 2H), 7.18 (dd, J=7.6, 7.2 Hz, 1H), 4.77 (d, J=5.6 Hz, 2H).

Example 120 tert-butyl 4-(2,10-difluoro-12-oxo-12H-thiochromeno[2,3-c]quinolin-6-yl)piperazine-1-carboxylate (7495)

Synthesized according to general procedure-D starting from scaffold compound 4o. Yield: 300 mg (69%), ES-MS [M+1]$^+$: 484.0, $t_R$: 7.77 min (Method-G), $^1$H NMR (400 MHz, DMSO-d$_6$): δ 9.35 (dd, J=12.8, 2.8 Hz), 8.18-8.11 (m, 2H), 7.99 (dd, J=9.2, 6 Hz), 7.79 (m, 1H), 7.67 (m, 1H), 3.62 (m, 4H), 3.25 (m, 4H), 1.43 (s, 9H).

Example 121 2,10-difluoro-6-(piperazin-1-yl)-12H-thiochromeno[2,3-c]quinolin-12-one (7425)

Synthesized according to general procedure-F starting from 1-Bocpiperazine instead of 4-methoxybenzylamine in step-1. Yield: 300 mg (69%), ES-MS [M+1]$^+$: 383.9, $t_R$: 4.66 min (Method-G), $^1$H NMR (400 MHz, DMSO-d$_6$): δ 9.32 (dd, J=12.8, 2.8 Hz), 8.15-8.09 (m, 2H), 7.99 (dd, J=9.2, 6 Hz), 7.78 (td, J=8.4, 2.8 Hz, 1H), 7.61 (td, J=8.8, 2.8 Hz, 1H), 3.35 (m, 4H), 3.20 (m, 4H).

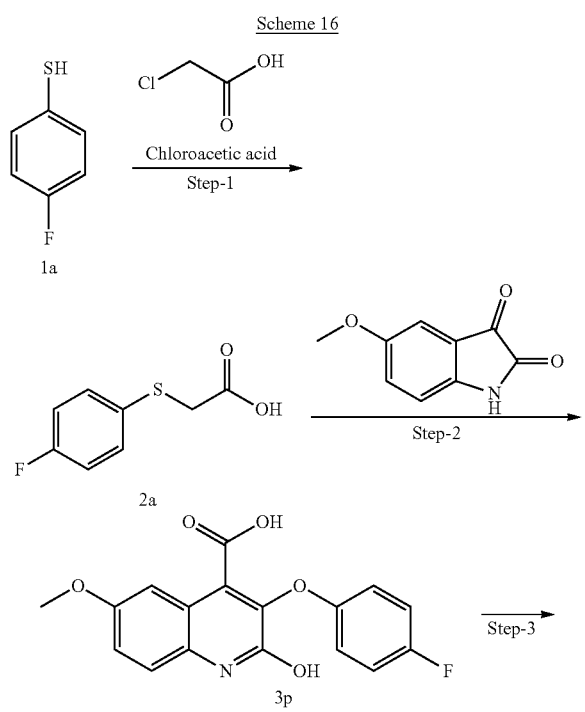

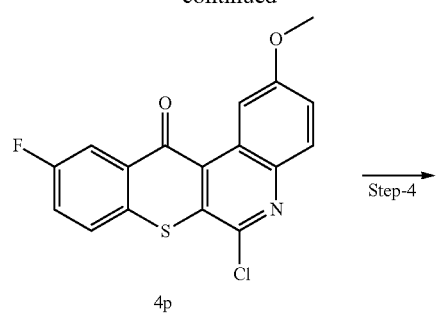

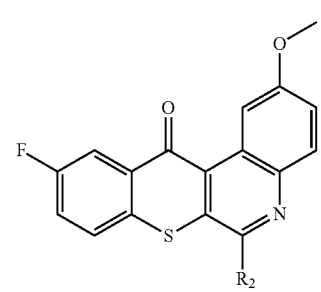

Example 122 6-chloro-10-fluoro-2-methoxy-12H-thiochromeno[2,3-c]quinolin-12-one (4p)

Synthesized in 2 steps starting from 5-methoxyisatin and compound 2a using general procedures B-C. Yield: 30% over 2 steps. ES-MS [M+1]$^+$: 345.8; $t_R$: 8.04 min (Method-G).

Example 123 10-fluoro-6-(3-(2-hydroxyethylamino)propylamino)-2-methoxy-12H-thiochromeno[2,3-c]quinolin-12-one (7407)

Synthesized according to general procedure-D starting from scaffold compound 4p. Yield: 135 mg (44%), ES-MS [M+1]$^+$: 428.0, $t_R$: 4.09 min (Method-G), $^1$H NMR (400 MHz, DMSO-d$_6$): δ 9.02 (d, J=2.8 Hz, 1H), 8.88 (brs, 1H), 8.17 (dd, J=9.6, 2.8 Hz, 1H), 8.02 (dd, J=9.2, 5.2 Hz, 1H), 7.77 (td, J=8.8, 2.8 Hz, 1H), 7.66 (d, J=8.8 Hz, 1H), 7.29 (dd, J=9.2, 2.8 Hz, 1H), 7.11 (t, J=4.8 Hz, 1H), 5.25 (brs, 1H), 3.85 (s, 3H), 3.66-3.59 (m, 4H), 3.00-2.64 (m, 4H), 2.10-2.05 (m, 2H).

Example 124 6-(benzylamino)-10-fluoro-2-methoxy-12H-thiochromeno[2,3-c]quinolin-12-one (7420)

Synthesized according to general procedure-D starting from scaffold compound 4p. Yield: 37 mg (10%), ES-MS [M+1]$^+$: 417.0, $t_R$: 7.87 min (Method-E), $^1$H NMR (400 MHz, DMSO-d$_6$): δ 9.05 (d, J=2.8 Hz, 1H), 8.21 (dd, J=9.6, 2.8 Hz, 1H), 8.08 (dd, J=8.8, 4.8 Hz, 1H), 7.80 (td, J=8.4, 2.8 Hz, 1H), 7.62 (d, J=8.8 Hz, 1H), 7.54 (t, J=5.6 Hz, 1H), 7.47 (d, J=7.2 Hz, 2H), 7.26-7.31 (m, 3H), 7.21 (t, J=7.2 Hz, 1H), 4.78 (d, J=5.6 Hz, 2H), 3.87 (s, 3H).

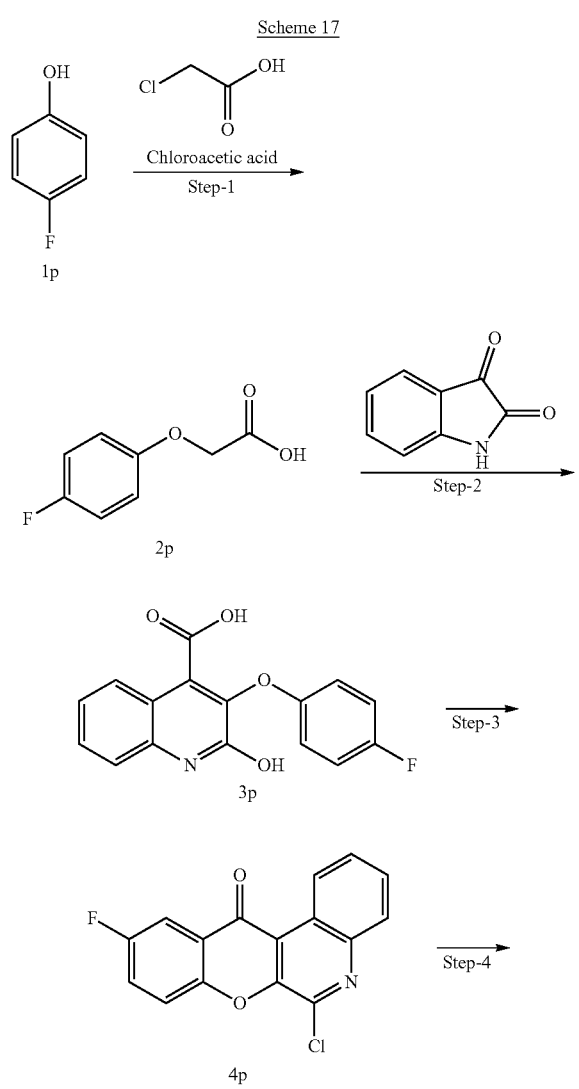
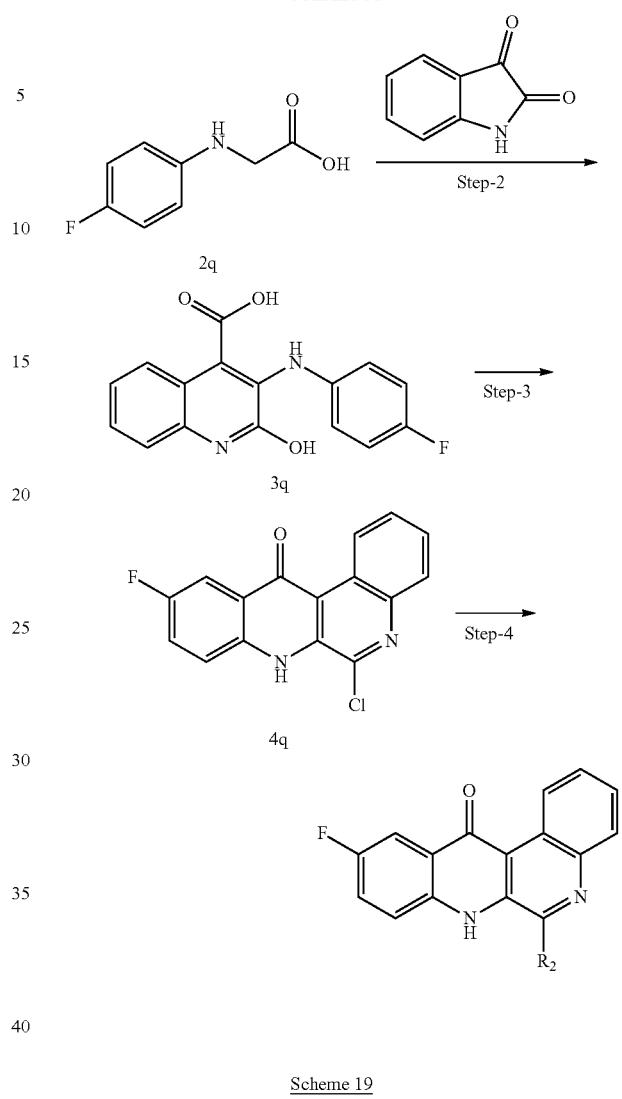
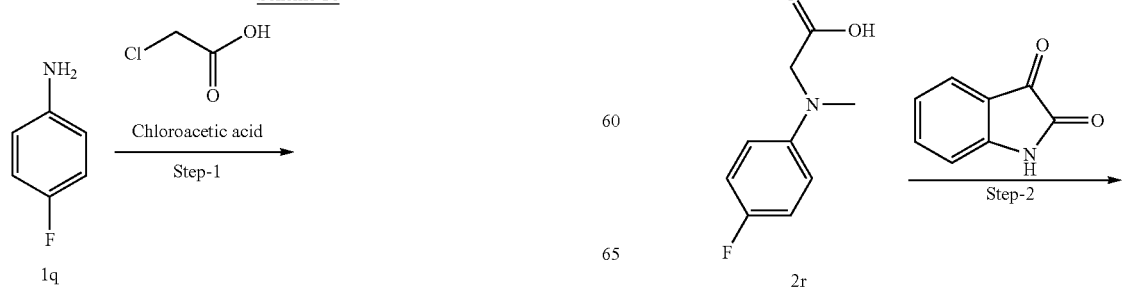

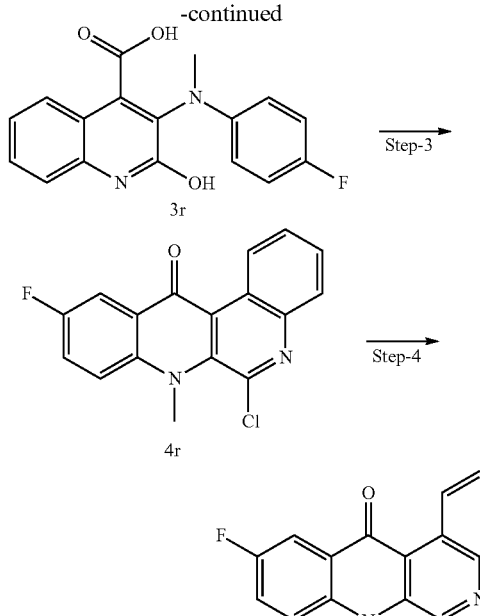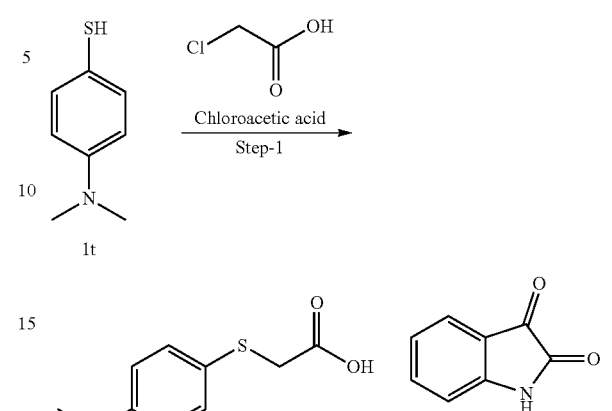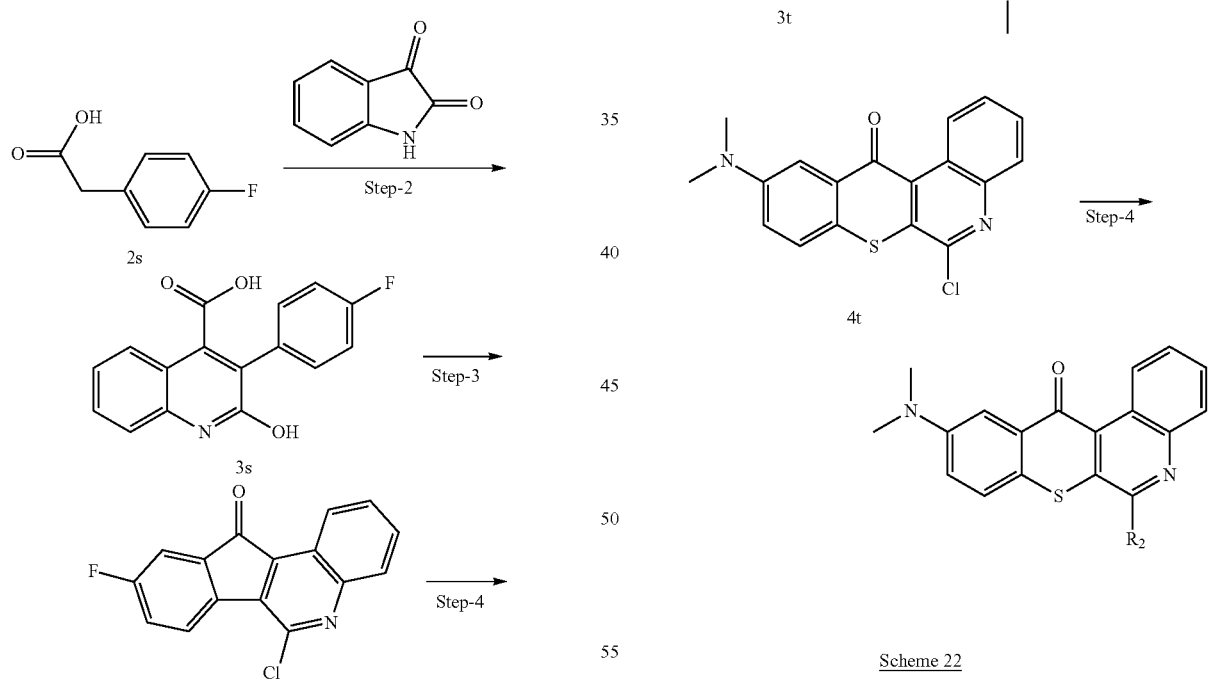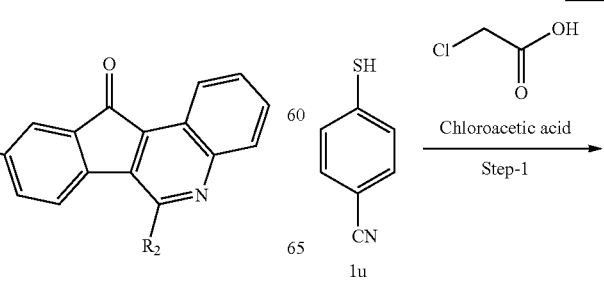

-continued
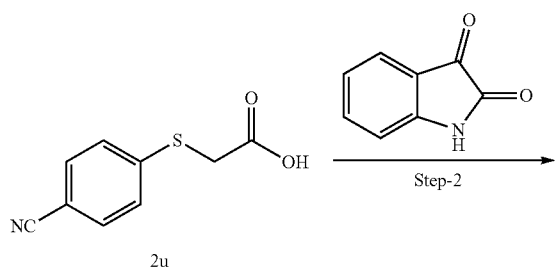
2u
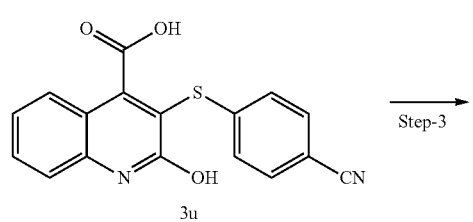
3u
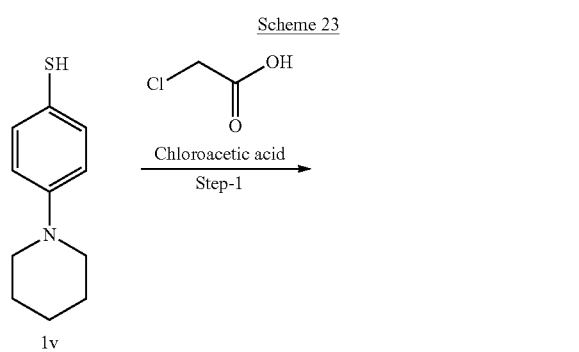
4u
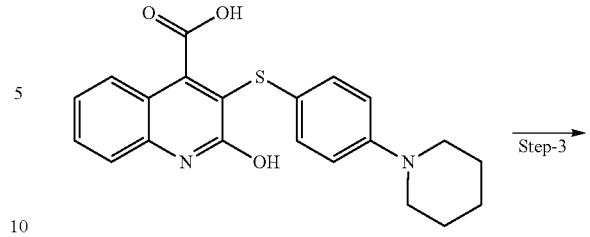
3v
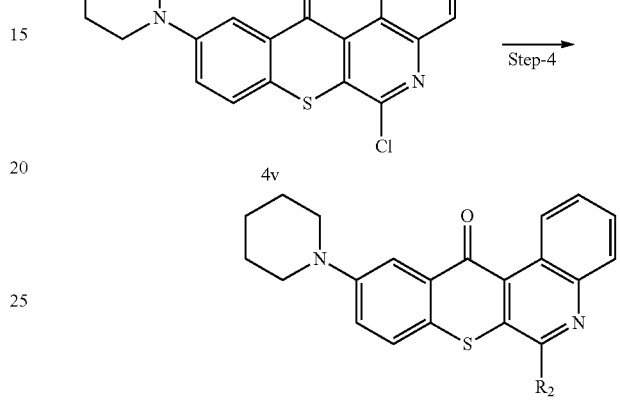
4v
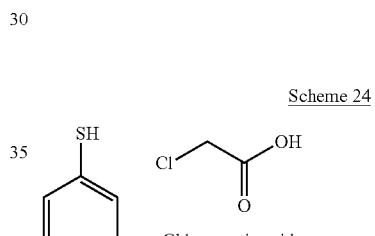
Scheme 23
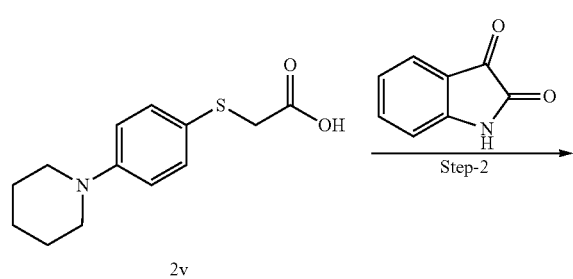
1v
Scheme 24
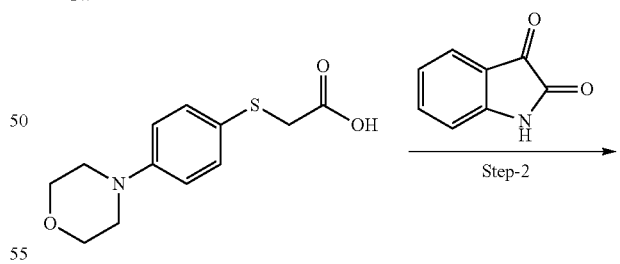
1w
2v
2w
3w 71
-continued
72
-continued
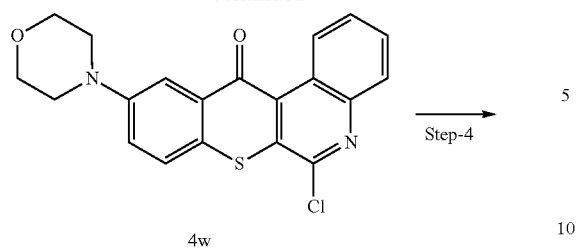
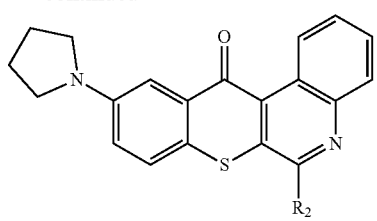
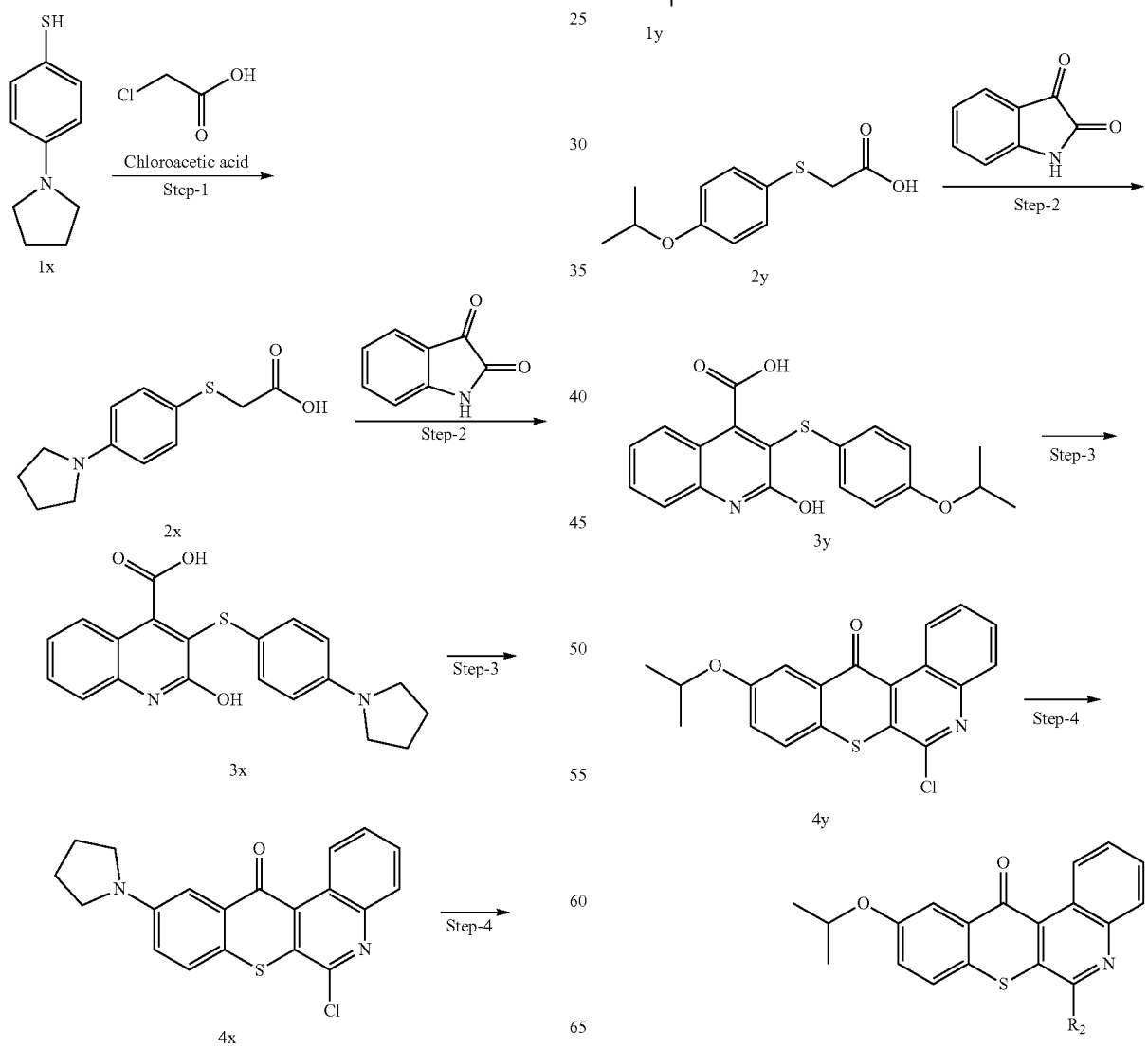

Scheme 27
Scheme 28
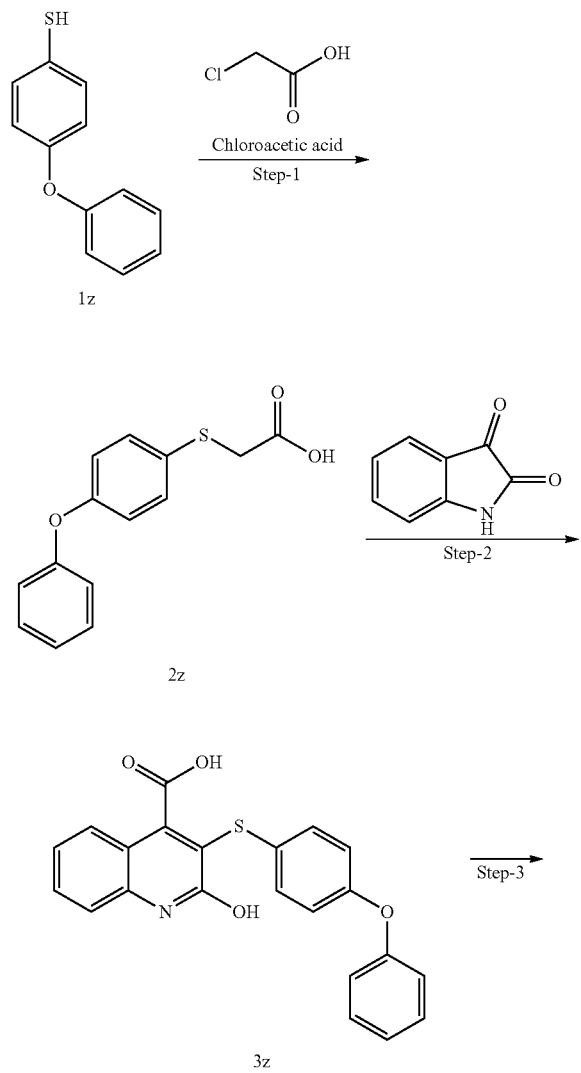
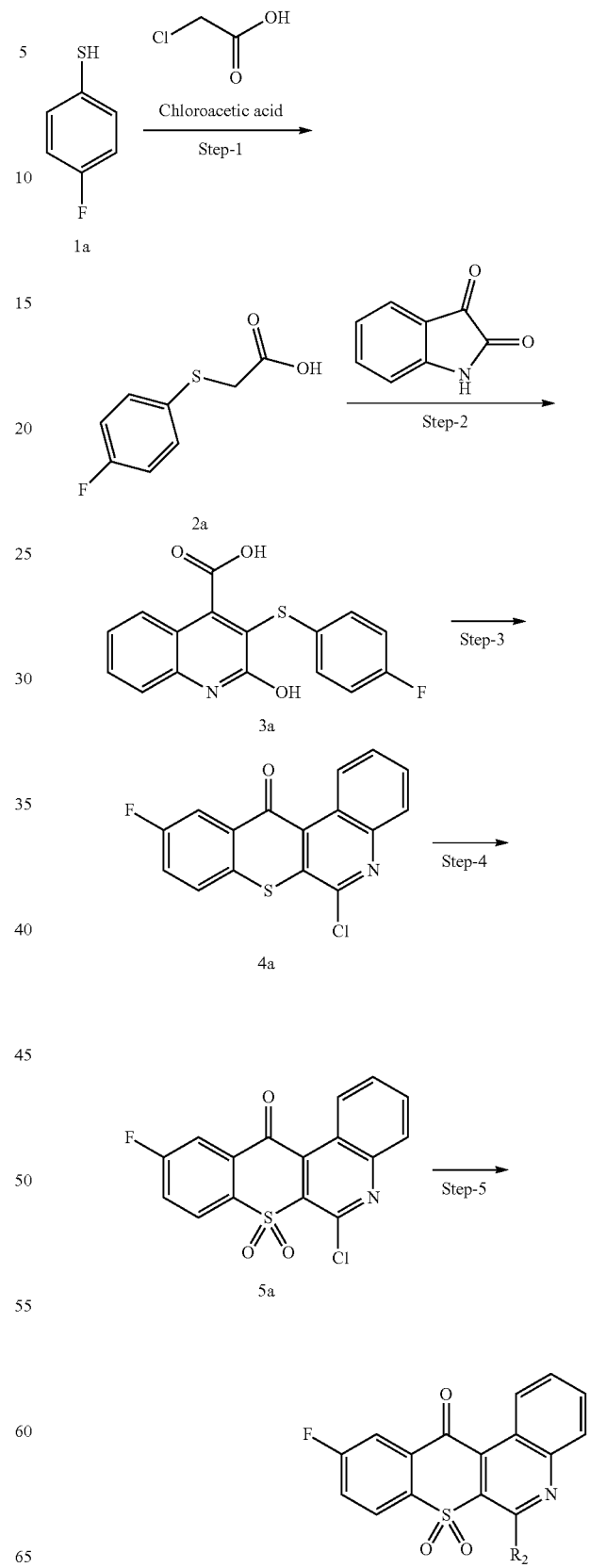

Scheme 29
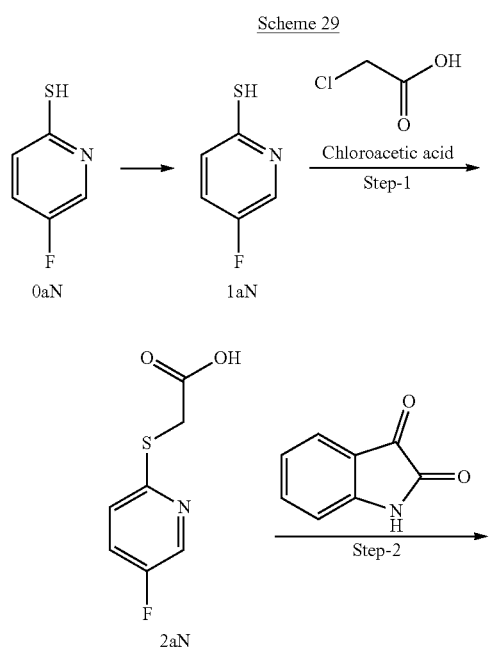
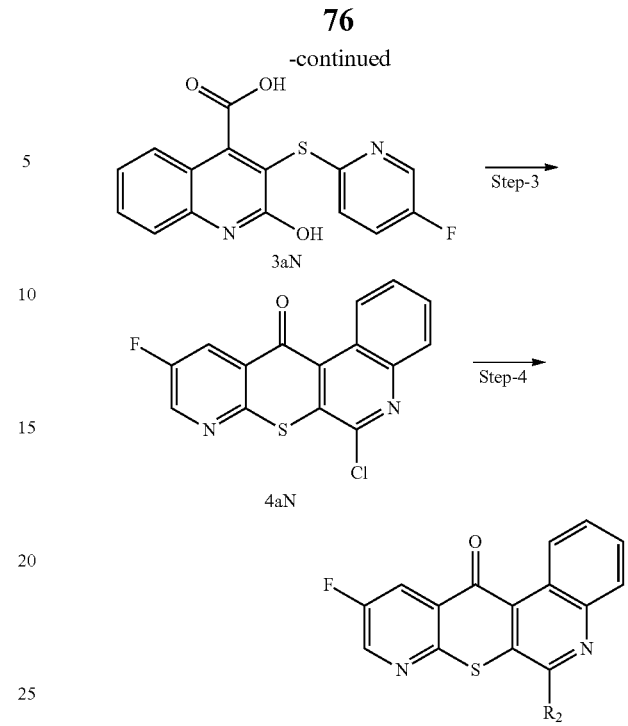
Scheme 30
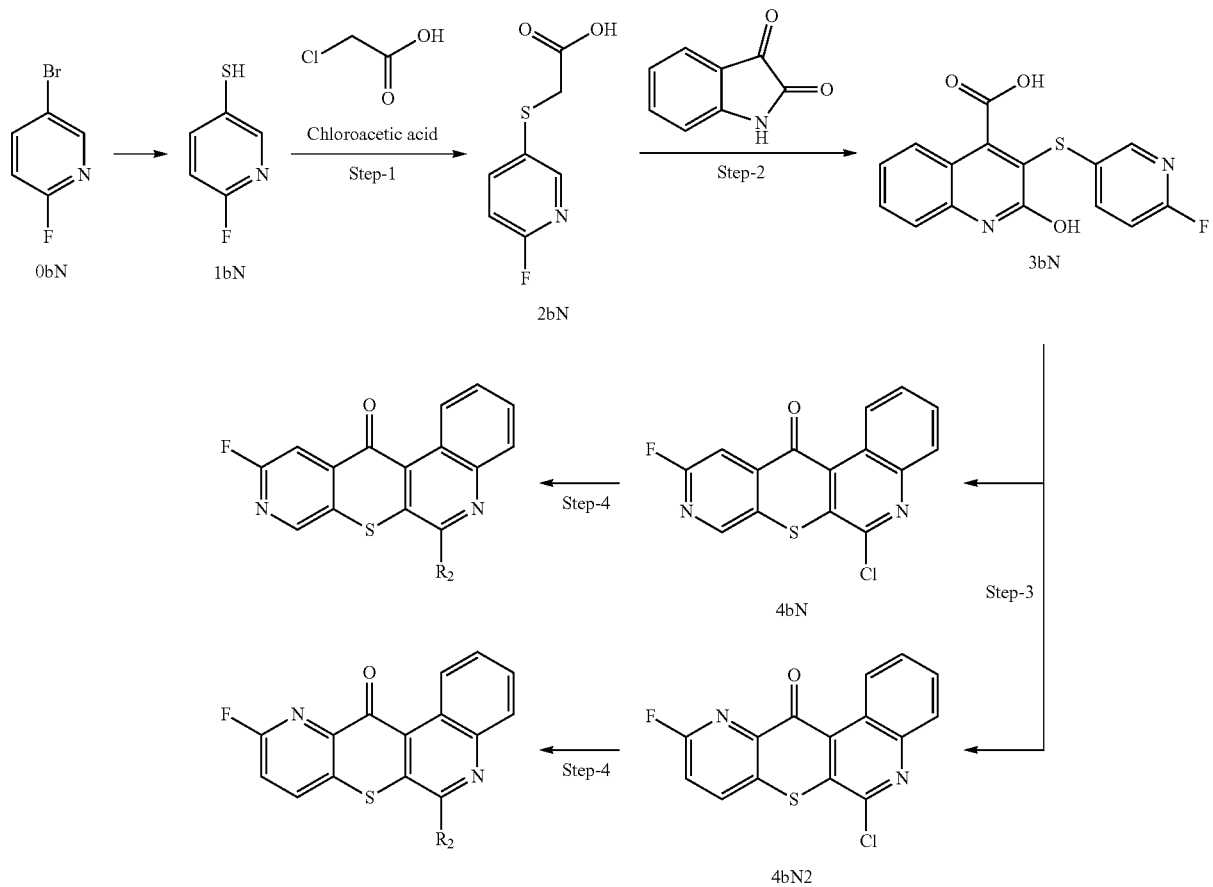

Scheme 31

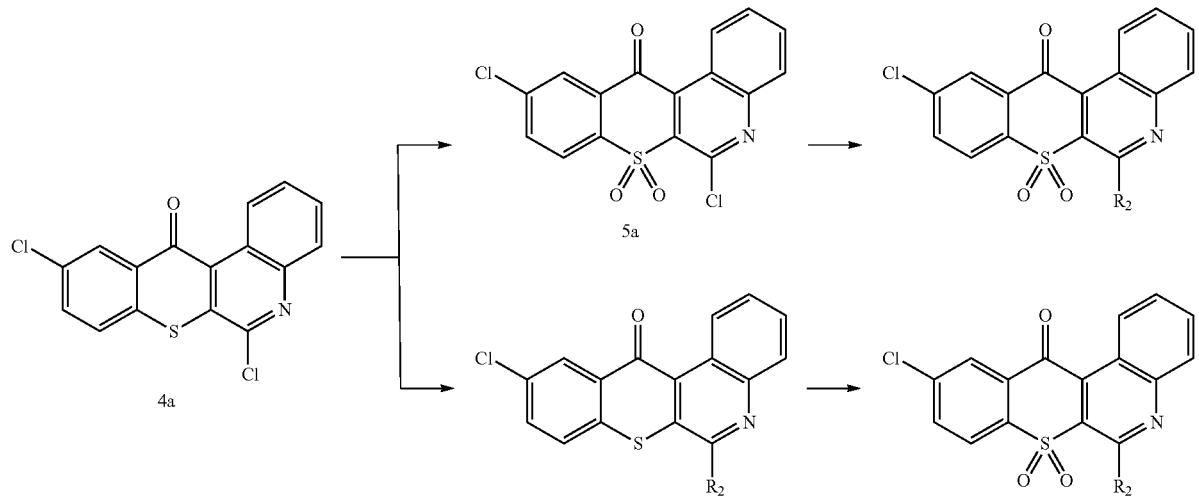

Example 124 6,10-dichloro-12H-thiochromeno[2,3-c]quinolin-12-one 7,7-dioxide (5a)

Synthesized according to general procedure-L starting from scaffold compound 4a. Yield: 480 mg (83%), ES-MS [M+1]$^+$: 363.8, $t_R$: 4.2 min (method-E), $^1$H NMR (400 MHz, TFA-d): δ 9.07 (d, J=7.6 Hz, 1H), 8.38 (m, 2H), 8.32-8.27 (m, 2H), 8.1 (m, 2H). $^{13}$C NMR (100 MHz, CDCl$_3$): 121.66, 125.37, 127.59, 128.51, 129.33, 130.85, 131.91, 132.27, 133.62, 135.23, 137.63, 138.46, 140.61, 143.04, 149.22, 179.89.

Example 125 6-Amino-10-chloro-12H-thiochromeno[2,3-c]quinolin-12-one 7,7-dioxide (7001)

Synthesized according to general procedure-F starting from 5a, by replacing DMSO with CHCl$_3$ as solvent, at 40° C. Yield: 310 mg (63%). ES-MS [M+1]$^+$: 344.9; $t_R$: 3.68 min (method-A), $^1$H NMR (400 MHz, CDCl$_3$): δ 8.58 (d, J=8.8 Hz, 1H), 8.12 (s, 1H), 8.07 (d, J=8.4 Hz, 1H), 7.81 (d, J=8.4 Hz, 1H), 7.73-7.67 (m, 2H), 7.44 (dd, J=7.6, 7.2 Hz, 1H), 6.12 (brs, 2H).

Example 126 10-chloro-6-(propylamino)-12H-thiochromeno[2,3-c]quinolin-12-one 7,7-dioxide (7002)

A mixture of 5a (1.0 eq.), propylamines (5.0 eq.) in CHCl$_3$ (~4-5 vol.) was stirred at RT for 24 hrs. After completion of the reaction, as monitored by TLC, the solvent was concentrated off. The crude product was purified by FCC to afford target compound as reddish orange solids. Yield: 130 mg (61%). ES-MS [M+1]$^+$: 387.0; $t_R$: 5.63 min (method-A), $^1$H NMR (400 MHz, CDCl$_3$): δ 8.48 (d, J=8.8 Hz, 1H), 8.09 (d, J=1.6 Hz, 1H), 8.04 (d, J=8.4 Hz, 1H), 7.79 (dd, J=8.0, 2.0 Hz, 1H), 7.73 (d, J=8.4 Hz, 1H), 7.66 (dd, J=7.6, 7.2 Hz, 1H), 7.35 (dd, J=8.0, 7.2 Hz, 1H), 6.89 (brs, 1H). 3.65 (m, 2H), 1.77 (sextet, J=7.2 Hz, 2H), 1.06 (t, J=7.2 Hz, 3H).

Example 127 6-((3-aminopropyl)amino)-10-chloro-12H-thiochromeno[2,3-c]quinolin-12-one 7,7-dioxide (7003)

H$_2$O$_2$ solution (~7 vol.) was added drop-wise to a stirred solution of 7704 (1.0 eq.) and TFA (~30 vol.) at RT, and the mixture was further stirred at same temperature for 1 hr. After completion of the reaction, as monitored by LCMS, the solvent was concentrated off. Resulting residue was quenched with ice-cold water and was basified with sat NaHCO$_3$ Soln (pH~8) and diluted with EtOAc (100 ml). The product that got precipitated out was filtered; washed with water and vacuum dried to afford target compound as reddish orange solid in almost pure form. Yield: 85 mg (31%). ES-MS [M+1]$^+$: 401.9; $t_R$: 2.16 min (method-A), $^1$H NMR (400 MHz, CDCl$_3$): (Poor peak resolution was observed; protons corresponding to two methylene groups gave distinct 4 signals) δ 8.37 (d, J=7.6 Hz, 1H), 8.17-8.08 (brm, 3H), 7.72 (brm, 1H), 7.64 (brm, 1H), 7.39 (brm, 1H), 7.23 (brm, 1H), 6.8 (brm, 1H), 3.63 (m, 2H), 3.03 (m, 1H), 2.66 (t, J=6.0 Hz, 1H), 1.74 (t, J=6.0 Hz, 2H).

Example 128 10-chloro-6-((3-((2-hydroxyethyl)amino)propyl)amino)-12H-thiochromeno[2,3-c]quinolin-12-one 7,7-dioxide (7004)

A mixture of 5a (1.0 eq.), 3-((2-hydroxyethyl)amino) propyl)amine (5.0 eq.) in CHCl$_3$ (~4-5 vol.) was stirred at RT for 24 hrs. After completion of the reaction, as monitored by TLC, the solvent was concentrated off. The crude product was purified by FCC to afford target compound as reddish orange solids. Yield: 105 mg (9%). ES-MS [M+1]$^+$: 446.0; $t_R$: 2.26 min (method-A), $^1$H NMR (400 MHz, DMSO-d$_6$): δ 8.42 (d, J=8.6 Hz, 1H), 8.30 (m, 1H), 8.23 (s, 1H), 8.2 (d, J=6.8 Hz, 1H), 8.12 (d, J=8.4 Hz, 1H), 7.77 (m, 1H), 7.68 (d, J=8.5 Hz, 1H), 7.45 (t, J=7.0 Hz, 1H), 7.33 (brs, 1H), 5.2 (brs, 1H), 3.71 (d, J=5.6 Hz, 2H), 3.63 (d, J=4.6 Hz, 2H), 3.03-2.98 (m, 4H), 2.04 (m, 2H).

Biological Assay

Prepare indicated substrate in freshly prepared Base Reaction Buffer (20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO). Deliver any required cofactors to the substrate solution above. Deliver indicated kinase into the substrate solution and gently mix. The testing compounds in DMSO was added into the kinase reaction mixture by Acoustic technology (Echo550; nanoliter range) and incubated for 20 minutes at room temperature. Deliver 33P-ATP (specific activity 10 uM) into the reaction mixture to initiate the reaction. Incubate kinase reaction for 2 hours at room temperature. Reactions are spotted onto P81 ion exchange paper. Detect kinase activity by filter-binding method.

Inhibition of FLT3 with 4-Quinolone Derivatives

| ID | Activity |
|---|---|
| (A: <51 nM; B: 51-200 nM; C: 201-500 nM; D: 501-1000 nM; E: >1 uM; N/A: not available) | |
| 7701 | E |
| 7702 | N/A |
| 7703 | E |
| 7704 | D |
| 7705 | E |
| 7706 | E |
| 7707 | A |
| 7708 | C |
| 7709 | E |
| 7710 | E |
| 7711 | B |
| 7712 | D |
| 7713 | E |
| 7714 | N/A |
| 7715 | A |
| 7716 | D |
| 7717 | E |
| 7718 | E |
| 7719 | E |
| 7720 | N/A |
| 7721 | D |
| 7722 | E |
| 7723 | E |
| 7724 | E |
| 7725 | E |
| 7726 | N/A |
| 7727 | N/A |
| 7728 | E |
| 7729 | E |
| 7730 | E |
| 7731 | C |
| 7732 | E |
| 7733 | E |
| 7734 | D |
| 7735 | E |
| 7736 | E |
| 7737 | N/A |
| 7738 | N/A |
| 7739 | B |
| 7740 | D |
| 7741 | N/A |
| 7742 | E |
| 7743 | E |
| 7744 | C |
| 7745 | E |
| 7746 | N/A |
| 7747 | E |
| 7748 | E |
| 7749 | N/A |
| 7750 | E |
| 7751 | E |
| 7752 | A |
| 7753 | E |
| 7754 | A |
| 7755 | D |
| 7756 | E |
| 7757 | C |
| 7758 | E |
| 7759 | N/A |
| 7760 | E |
| 7761 | E |
| 7762 | N/A |
| 7763 | E |
| 7764 | N/A |
| 7765 | E |
| 7766 | E |
| 7767 | A |
| 7801 | N/A |
| 7001 | E |
| 7002 | N/A |
| 7003 | N/A |
| 7004 | N/A |
| 7402 | E |
| 7403 | E |
| 7406 | E |
| 7407 | E |
| 7408 | E |
| 7416 | N/A |
| 7420 | N/A |
| 7422 | E |
| 7424 | E |
| 7425 | E |
| 7495 | N/A |
| 7201 | E |
| 7202 | B |
| 7203 | E |
| 7211 | A |
| 7212 | A |
| 7213 | E |
| 7214 | E |
| 7215 | C |
| 7224 | C |
| 7225 | C |
| 7226 | E |
| 7231 | A |
| 7232 | E |
| 7233 | E |
| 7240 | A |
| 7241 | E |
| 7242 | N/A |
| 7244 | A |
| 7245 | E |
| 7246 | N/A |
| 7247 | B |
| 7297 | N/A |
| 7248 | B |
| 7249 | N/A |
| 7250 | N/A |
| 7252 | C |
| 7253 | E |
| 7254 | B |
| 7255 | N/A |
| 7256 | N/A |
| PKC412 | A |
| AC220 | A |

What is claimed is:

1. A compound having the following Formula (I-1),

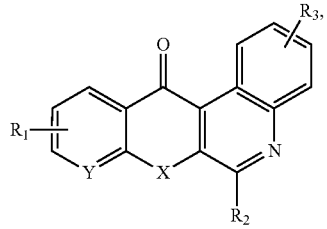

wherein

Y is [P]n, wherein P is —CH—, —N— or —O—;
X is [Q]n, wherein Q is —CH$_2$—, —N—, —O—, —S—, —SO$_2$— or —N-alkyl;
n is 1;
R$_1$ is CN, F, —OC$_{1-4}$alkyl, C$_{1-4}$alkyl or haloC$_{1-4}$alkyl;
R$_2$ is —NH$_2$, —NR$_d$R$_e$—, —O-alkyl, C(=O)— 5- or 6-membered aryl or —C(=O)— 5- or 6-membered heteroaryl;
  R$_d$ is 2-(2-pyridinylamino)ethyl, OH, alkyl, alkenyl, aryl, heteroaryl, heteroalkenyl, -alkylene-NR$_a$R$_e$, -alkylene-N(R$_b$)$_2$, -alkylene-OR$_c$, -alkylene-5- or 6-membered aryl, -alkylene-5- or 6-membered heteroaryl, or 5- or 6-membered heterocycloalkyl or heteroaryl containing at least one N;
  R$_a$ is H, alkyl, alkenyl, halogen, hydroxyalkyl, —OH, —NO$_2$ or phenyl;
  R$_b$ is alkyl, alkenyl or halogen;
  R$_e$ is H, alkyl, alkenyl or aryl; or
  R$_d$R$_e$ together with N forms a 3-8 membered heterocycloalkyl or heteroaryl ring, optionally substituted or N-substituted with C$_1$-C$_3$ alkyl, C$_1$-C$_3$ alkylene-phenyl, tert-butyloxycarbonyl,
  R$_c$ is H, alkyl, alkenyl, halogen, or phenyl;
R$_3$ is —OCH$_3$, H, alkyl, alkenyl, halogen or CN, NH$_2$ or NO$_2$,
wherein the alkyl or alkenyl is unbranched or branched, unsubstituted or substituted by halogen, hydroxyl, amino or nitro; and
wherein the cycloalkyl or heterocycloalkyl is unsubstituted or substituted by halogen, —OH, —NH$_2$, —NO$_2$, —CN, alkyl, alkenyl, —NHR$_a$, N(R$_b$)$_2$ or —OR$_a$;
or a solvate, stereoisomer, enantiomer, or pharmaceutically acceptable salt thereof.

2. The compound of claim 1, Q is —S—.

3. The compound of claim 1, P is —C— or —N—.

4. The compound of claim 1, wherein R$_2$ is —NH—C$_{1-3}$alkylene-NHR$_a$, —NH—C$_{1-3}$ alkylene-NH$_2$, —NH-C$_{1-3}$alkylene-OH, —NH-C$_{1-3}$alkylene-NHC$_{1-4}$alkylOH, —C$_{1-3}$ alkylene-5- or 6-membered aryl, —C$_{1-3}$ alkylene-5- or 6-membered heteroaryl.

5. The compound of claim 1, R$_3$ is H.

6. The compound of claim 1, which is selected from the group consisting of:

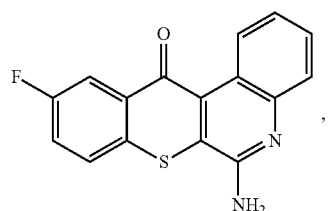

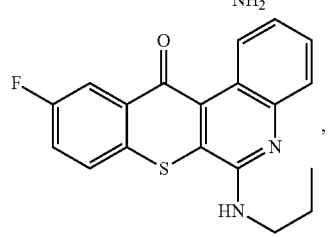

-continued

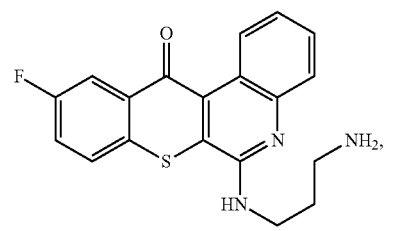

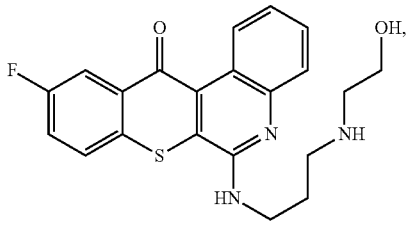

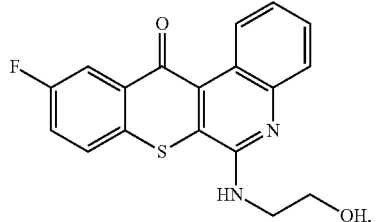

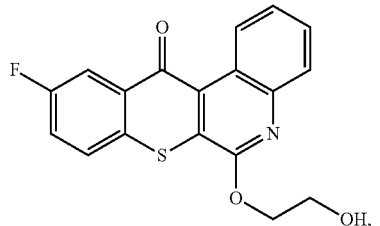

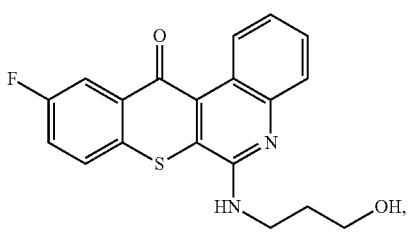

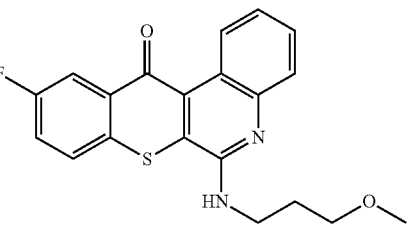

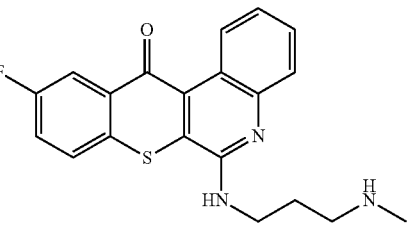

83
-continued
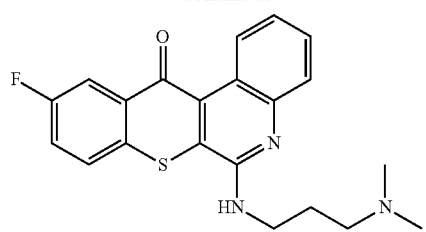
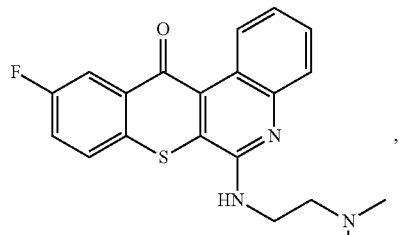
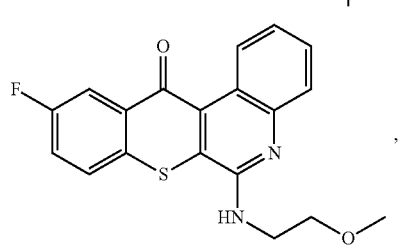
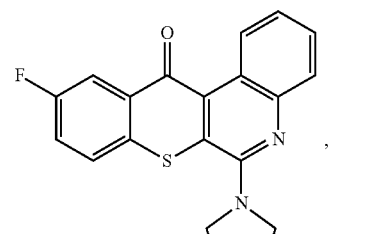
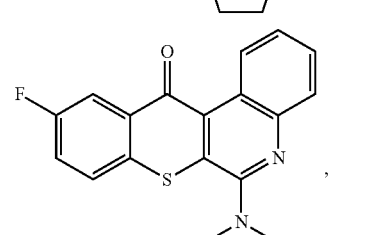
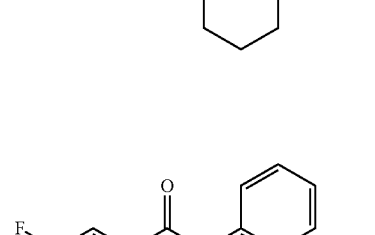
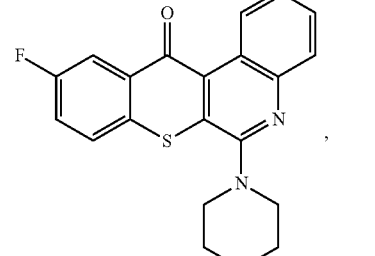
84
-continued
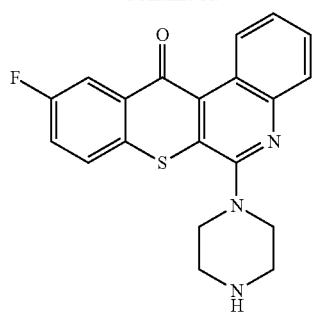
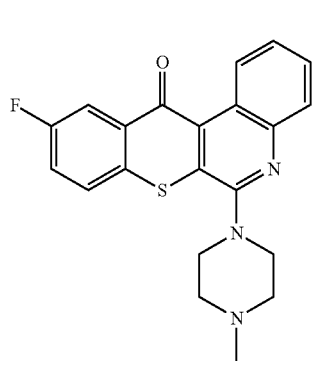
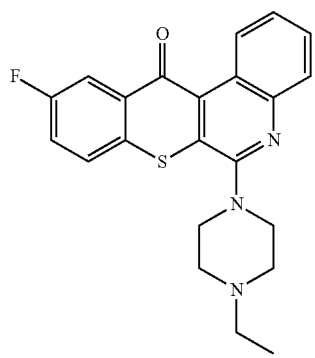
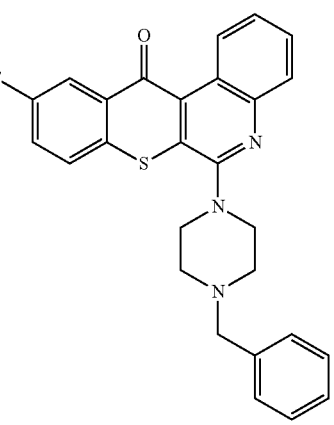

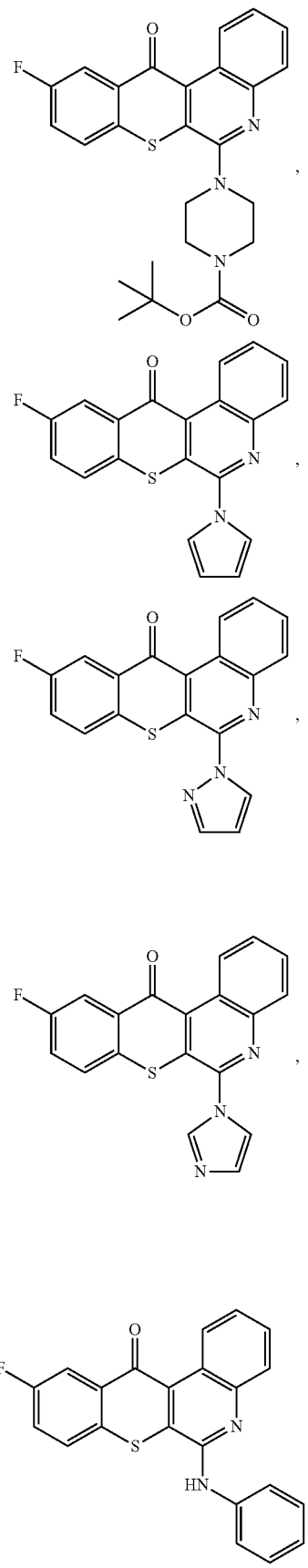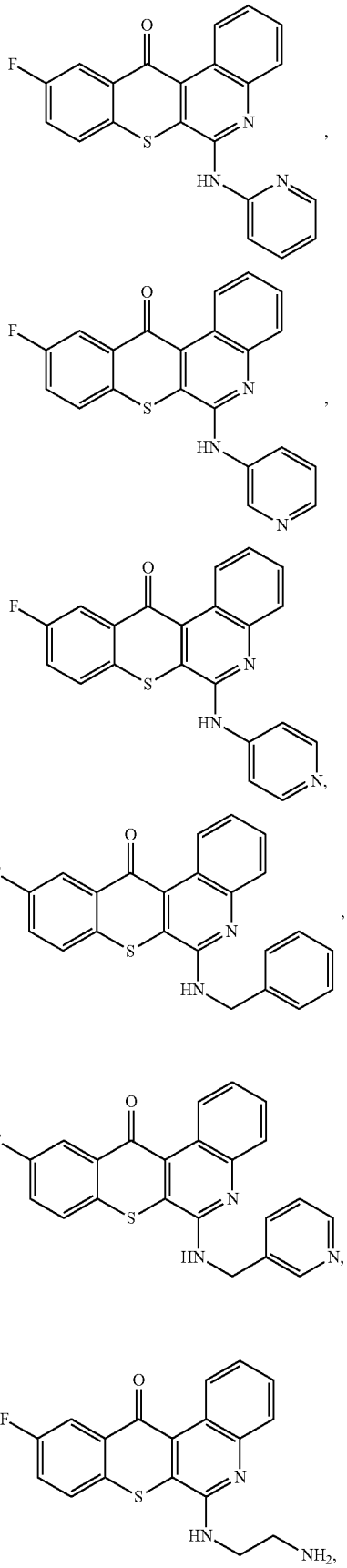

-continued
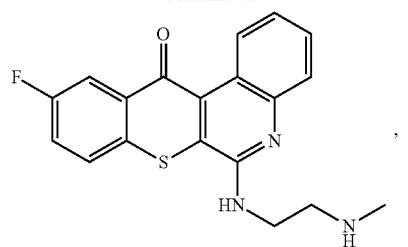
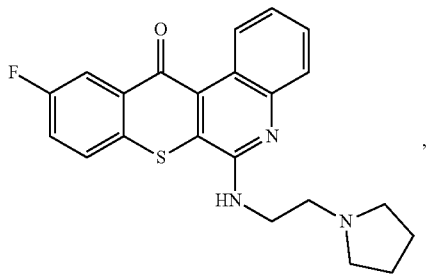
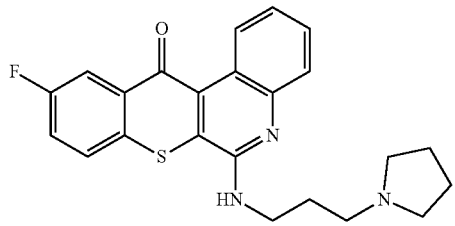
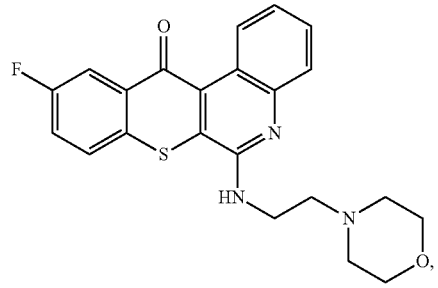
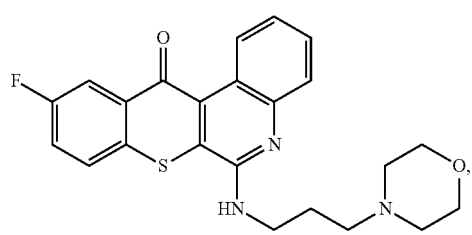
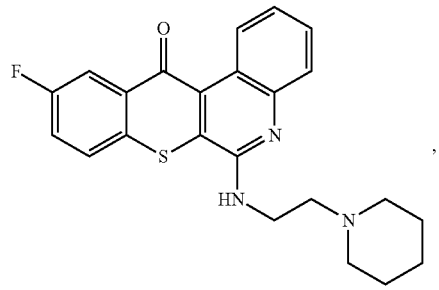
-continued
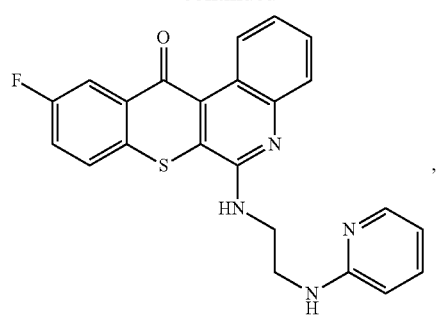 [SMILES: O=c1c2cc(F)ccc2sc2c(NCCNc3ccccn3)nc3ccccc3c12]
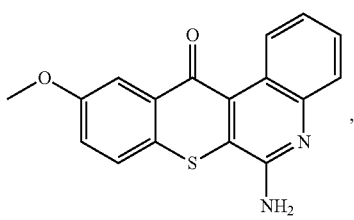
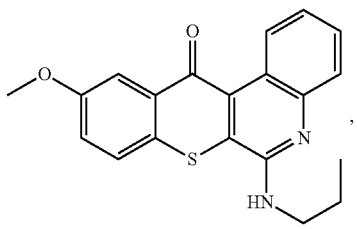
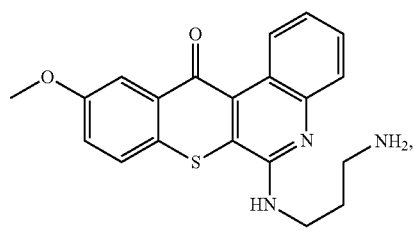
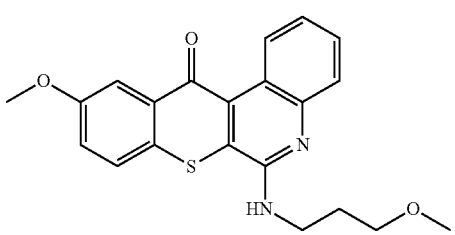
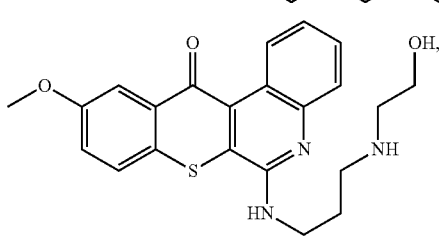
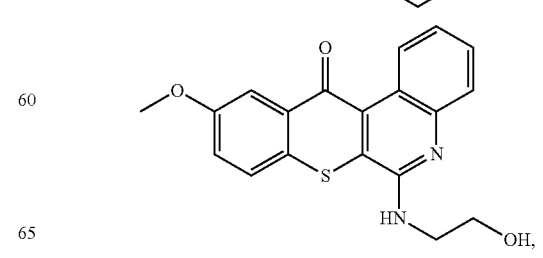

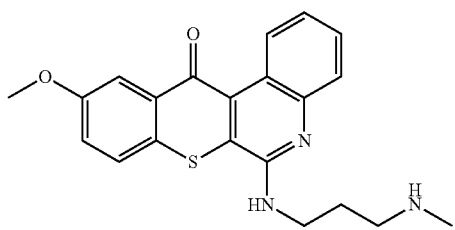,
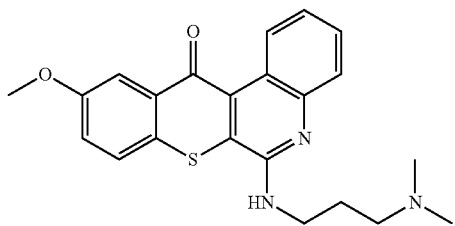,
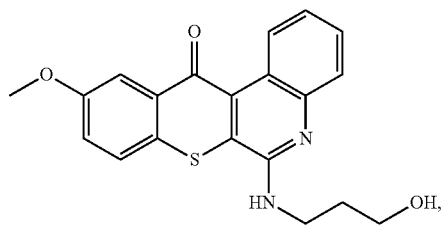,
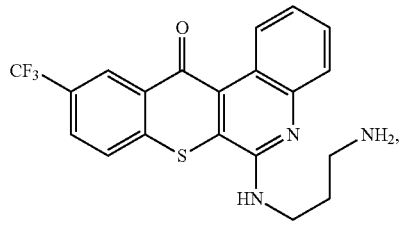,
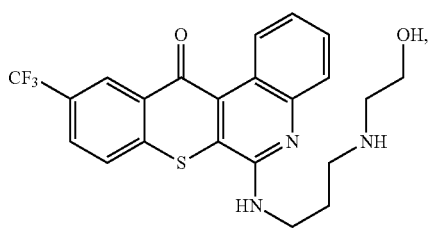,
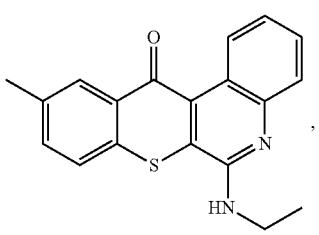,
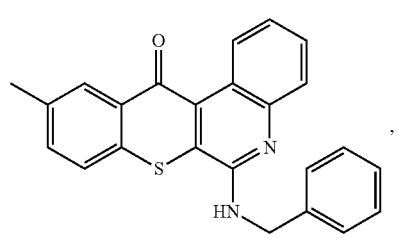,
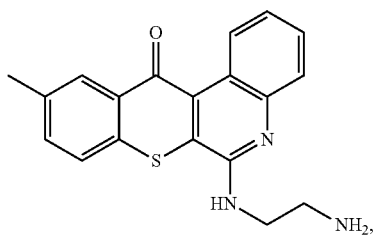,
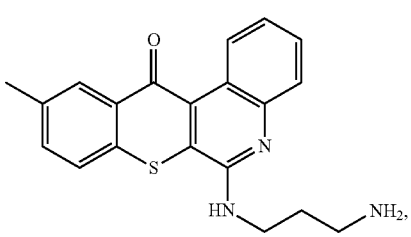,
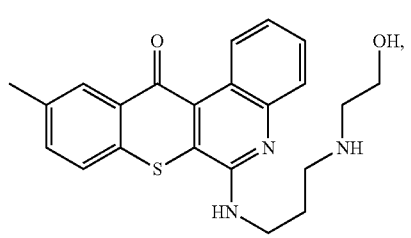,
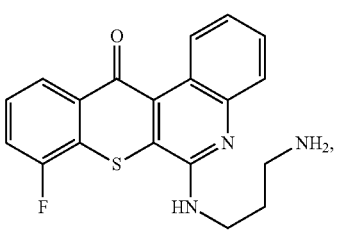,
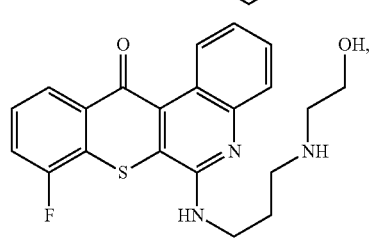,
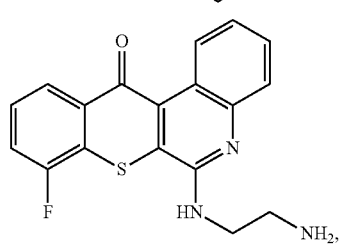,
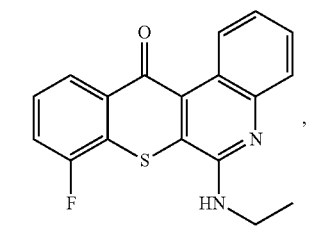, 91
-continued
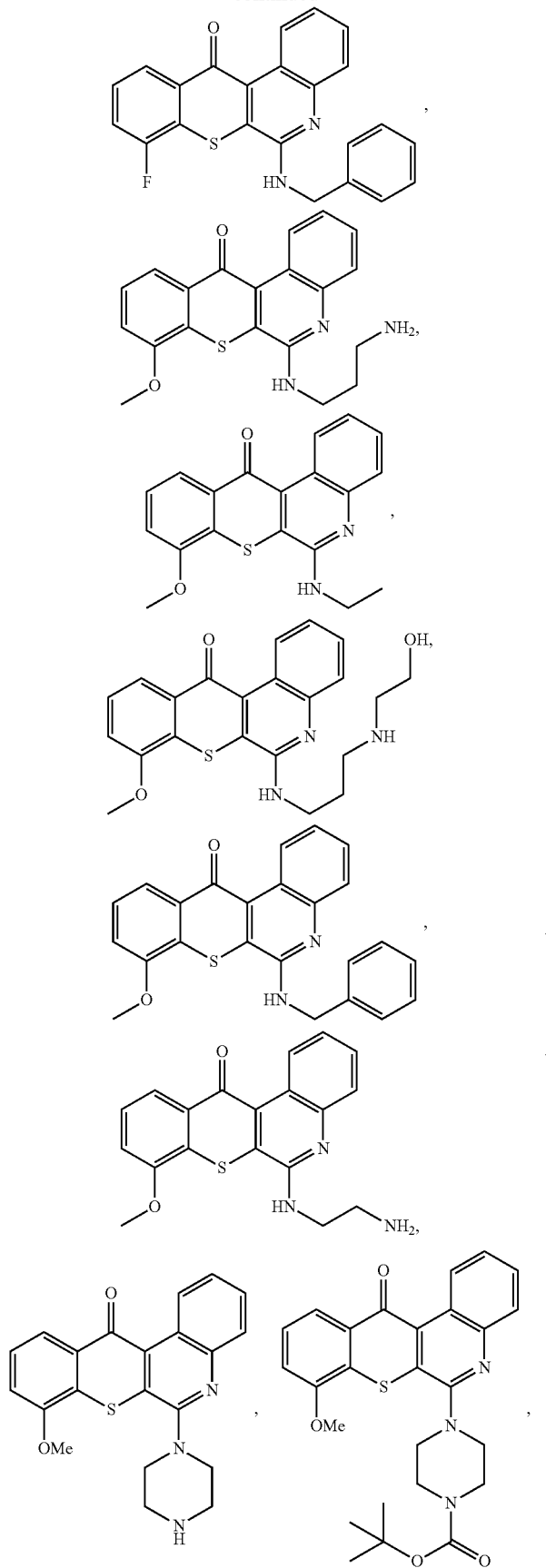
92
-continued
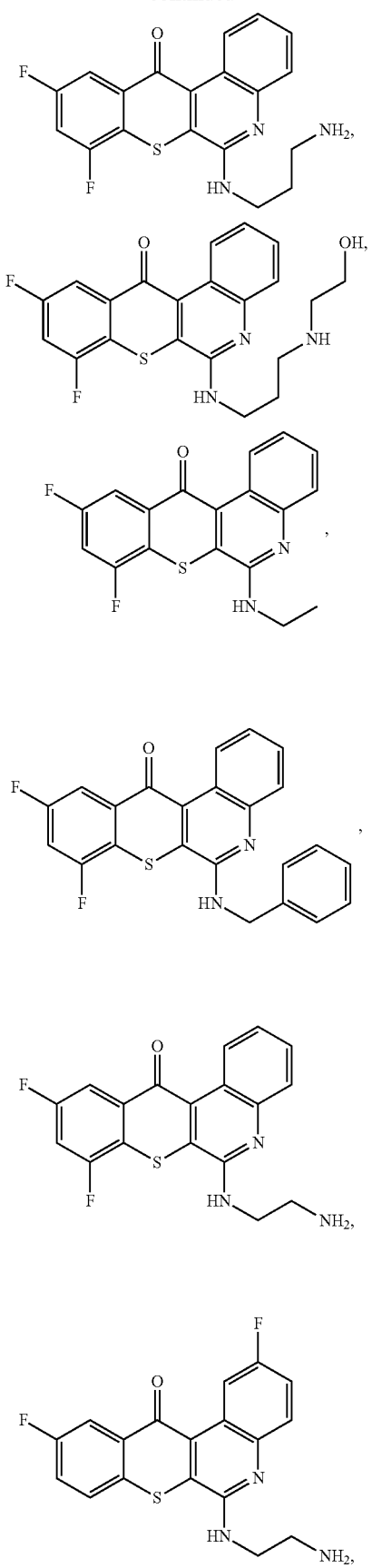

93
-continued

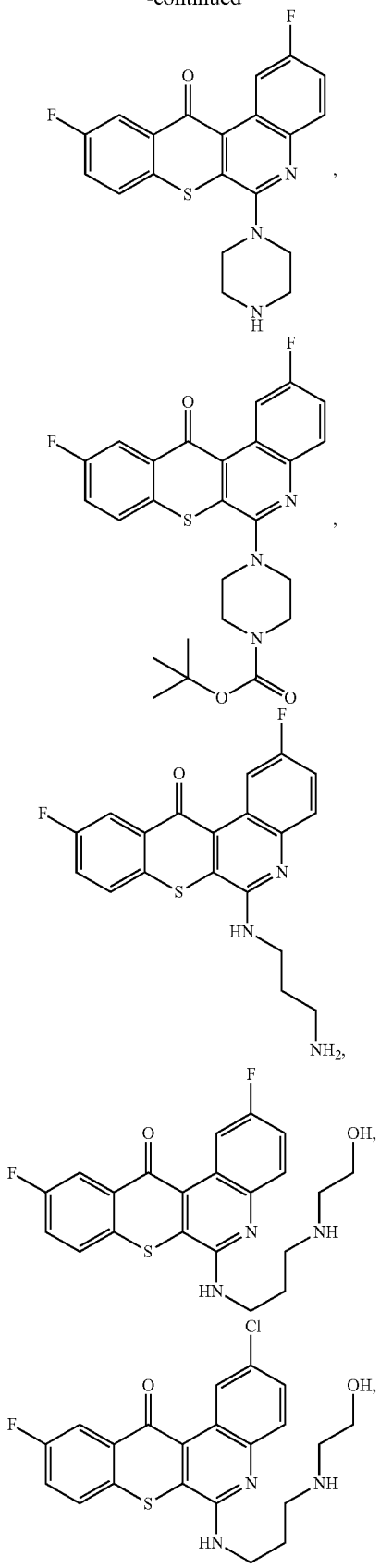

94
-continued

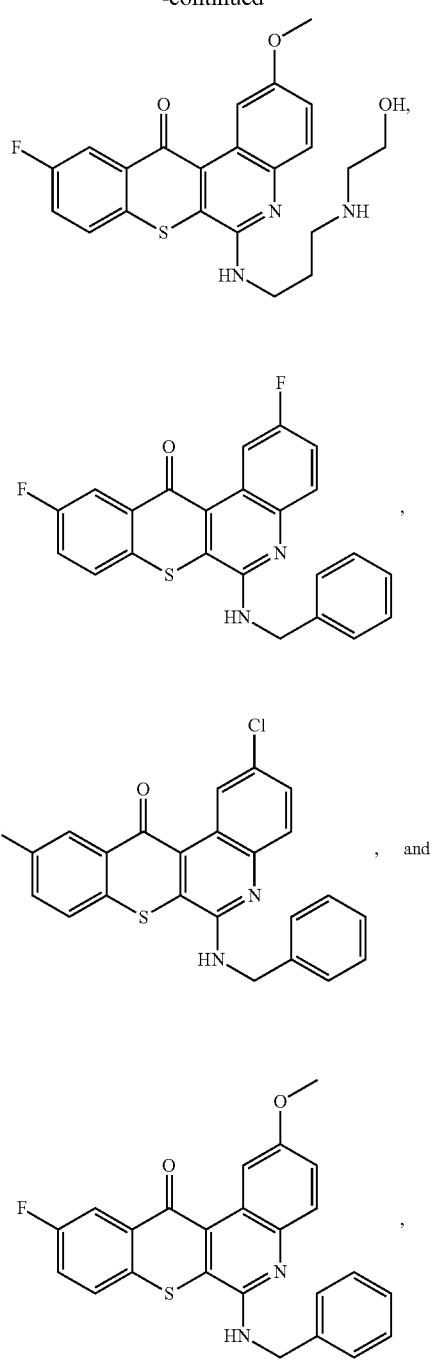

or stereoisomer, enantiomer, or pharmaceutically acceptable salt thereof.

7. A pharmaceutical composition comprising a compound of claim 1, together with a pharmaceutically acceptable carrier.

8. A method of inhibiting FLT3, comprising contacting a cell with a compound of claim 1.

9. The compound of claim 1, wherein $R_a$ is H and $R_c$ is hydroxyC$_{1-4}$alkyl.

* * * * *